US005552267A

United States Patent [19]

Stern et al.

[11] Patent Number: 5,552,267
[45] Date of Patent: Sep. 3, 1996

[54] SOLUTION FOR PROLONGED ORGAN PRESERVATION

[75] Inventors: David M. Stern, Great Neck, N.Y.; Mehmet C. Oz, Fort Lee; Roman Nowygrod, Teaneck, both of N.J.; Shin Koga, New York; David J. Pinsky, Riverdale, both of N.Y.

[73] Assignee: The Trustees of Columbia University in the City of New York, New York, N.Y.

[21] Appl. No.: 350,319

[22] Filed: Dec. 5, 1994

Related U.S. Application Data

[63] Continuation-in-part of Ser. No. 206,197, Mar. 3, 1994, Pat. No. 5,370,989, which is a continuation of Ser. No. 863,197, Apr. 3, 1992, abandoned.

[51] Int. Cl.$^6$ ........................................................ A01N 1/02
[52] U.S. Cl. ................................................ 435/1.1; 435/1.2
[58] Field of Search ......................................... 435/1, 283

[56] References Cited

U.S. PATENT DOCUMENTS

| | | | |
|---|---|---|---|
| 4,668,686 | 5/1987 | Meanwell et al. | 514/293 |
| 4,701,459 | 10/1987 | Meanwell et al. | 514/293 |
| 4,775,674 | 10/1988 | Meanwell et al. | 514/293 |
| 4,798,824 | 1/1989 | Belzer et al. | 514/60 |
| 4,927,762 | 5/1990 | Le Darfler | 435/240.31 |
| 4,943,573 | 7/1990 | Meanwell | 514/253 |
| 4,963,561 | 10/1990 | Lesher et al. | 514/303 |
| 4,983,586 | 1/1991 | Bodor | 514/58 |
| 4,999,365 | 3/1991 | Dage et al. | 514/341 |
| 5,002,965 | 3/1991 | Ramwell et al. | 514/468 |
| 5,025,001 | 6/1991 | Loscalzo et al. | 514/91 |
| 5,145,771 | 9/1992 | Lemasters et al. | 435/1 |
| 5,340,827 | 8/1994 | Beeley et al. | 514/352 |
| 5,370,989 | 12/1994 | Stern et al. | 435/1 |

OTHER PUBLICATIONS

Stelzner, T. J., et al., *Journal of Cellular Physiology* 139:157–166 (1989).
Pinsky, D., et al., *J. Clin. Invest.* 92:2994–3002 (1993).
Pinsky, D. J., et al., *J. Clin. Invest.* 93:2291–2297 (1993).
Maurer, E. J., et al., *Transplantation Proceedings* 22:548–550 (1990).
Nozaki, H., et al., *The Tohoku Journal of Experimental Medicine* 115:145–154 (1975).
Ogawa, S., et al., *American Journal of Physiology* 262:C546–C554 (1992).
Okouchi, Y., et al., *The Journal of Thoracic and Cardiovascular Surgery* 99:1104–1108 (1990).
Pasque, M. K., et al., *Annals of Surgery* 200:1–12 (1984).
Swanson, D. K., et al., *J. Heart Transplantation* 7:456–467 (1988).
Swanson, D. K., et al., *J. Heart Transplantation* 28:476–481 (1979).
W. J. Thompson, *Pharmac. Ther.* (1991) 51:13–33.
J. P. Hall, *Br. J. Clin. Pharmac.* (1993) 35:1–7.

*Primary Examiner*—Robert Warden
*Assistant Examiner*—Krisanne M. Thornton
*Attorney, Agent, or Firm*—John P. White

[57] ABSTRACT

An aqueous solution for organ preservation or maintenance, which contains: a vasodilator in an amount sufficient to maintain vascular homeostasis; D-glucose in an amount sufficient to support intracellular function and maintenance of cellular bioenergetics; magnesium ions in an amount sufficient to support intracellular function and maintenance of cellular bioenergetics; macromolecules of molecular weight greater than 20,000 daltons in an amount sufficient to maintain endothelial integrity and cellular viability; potassium ions in a concentration greater than about 110 mM; and a buffer in an amount sufficient to maintain the average pH of the organ preservation or maintenance solution during the period of organ preservation at about physiologic pH or above.

47 Claims, 33 Drawing Sheets

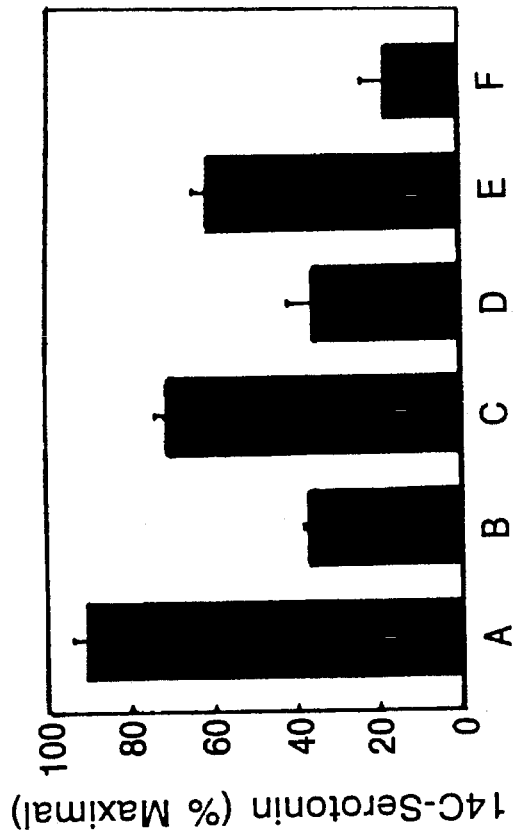

SOLUTION FOR PROLONGED ORGAN PRESERVATION

The invention described herein was made in the course of work under Grant Numbers HL-21006, HL-34625, HL-42507 HL-42833, and HL-50629 from the Public Health Service (PHS), Department of Health and Human Services. Accordingly, the United States government has certain rights in this invention.

This is a continuation-in-part of U.S. Ser. No. 08/206, 197, filed Mar. 3, 1994, now U.S. Pat. No. 5,370,989, issued Dec. 6, 1994 which is a continuation of U.S. Ser. No. 07/863,197, filed Apr. 3, 1992, abandoned, the contents of which are hereby incorporated by reference.

Throughout this application, various publications are referred to within parenthesis or by endnotes. Disclosures of these publications in their entireties are hereby incorporated by reference into this application to more fully describe the state of the art to which this invention pertains. Full bibliographic citation for these references may be found in the text or, for the second through fifth Series of Experiments, at the end of the each section.

BACKGROUND OF THE INVENTION

The present invention relates to a solution for prolonged organ preservation, and more particularly to an aqueous solution for organ preservation or maintenance. The invention also provides a method of preserving or maintaining an organ, comprising contacting the organ with the solution for organ preservation or maintenance.

Adequate preservation of organs intended for transplantation is critical to the proper functioning of the organ following implantation. This invention concerns an organ preservation or maintenance solution that can preserve organs intended for transplantation for periods of time that are longer than the currently best solution available. A longer preservation time is desired to enable cross-matching of donor and recipient to improve subsequent survival, as well as to allow for coast to coast and international transportation of organs to expand the donor and recipient pools. Experimental work for this invention has focused on the heart, but the organ preservation or maintenance solution of the subject invention may be used for other organs, and for tissues and cells, as well.

Many different organ preservation solutions have been designed, as investigators have sought to lengthen the time that an organ may remain extra-corporeally, as well as to maximize function of the organ following implantation. Several of the key solutions that have been used over the years include: 1) the Stanford University solution [see, e.g., Swanson, D. K., et al., Journal of Heart Transplantation, (1988), vol. 7, No. 6, pages 456–467 (mentions composition of the Stanford University solution)]; 2) a modified Collins solution [see, e.g., Maurer, E. J., et al., Transplantation Proceedings, (1990), vol. 22, No. 2, pages 548–550; Swanson, D. K., et al., supra (mention composition of modified Collins solution)]; and 3) the University of Wisconsin solution (Belzer, et al., U.S. Pat. No. 4,798,824, issued Jan. 17, 1989). Of those, the University of Wisconsin (UW) solution is currently regarded as the best. (See, e.g., Maurer, E. J., et al., supra).

In addition to the composition of the organ preservation or maintenance solution, the method of organ preservation also affects the success of preservation. Several methods of cardiac preservation have been studied in numerous publications: 1) warm arrest/cold ischemia; 2) cold arrest/macroperfusion; 3) cold arrest/microperfusion; and 4) cold arrest/cold ischemia. The first method involves arresting the heart with a warm cardioplegic solution prior to explantation and cold preservation, but this method fails because of the rapid depletion of myocardial energy store during the warm period. The second method, which involves arresting the heart with a cold preservation solution, is better; but continuous perfusion of the heart with preservation solution during the storage period fails because of the generation of toxic oxygen radicals. In addition, the procedure of the second method is cumbersome and does not lend itself to easy clinical use. The third method, first described in Nature in 1972 in a system called "trickle perfusion," is better but also cumbersome. The fourth method of preservation is that of a cold cardioplegic arrest followed by a period of cold immersion of the heart. The fourth method is currently the standard method of cardiac preservation. This fourth method reliably preserves hearts for periods of up to six (6) hours, but less than four (4) hours is considered ideal for this method. Since a longer preservation time is desirable, attempts have been made to improve preservation solutions in such a way as to reliably preserve hearts and other organs for longer periods of time.

Though the University of Wisconsin (UW) solution is currently the industry standard of organ preservation solutions, it is limited in the length of preservation time that it provides.

SUMMARY OF THE INVENTION

The organ preservation or maintenance solution of the present invention shows a substantial improvement over the prior art for increasing the preservation time for organs intended for transplantation. (See Experimental section). The organ preservation or maintenance solution of this subject invention shall also be referred to as the Columbia University (CU) solution.

The subject invention differs from other organ preservation solutions of the prior art in a number of respects.

The present invention includes a vasodilator. The vasodilator in the subject invention may be selected from the group consisting of phosphodiesterase inhibitors, analogues of adenosine 3',5'-cyclic monophosphate (cyclic adenosine monophosphate, cyclic-AMP, or cAMP), analogues of guanosine 3',5'-cyclic monophosphate (cyclic guanosine monophosphate, cyclic-GMP, or cGMP), nitroglycerin, adenosine, or suitable combinations thereof. Dibutyryl adenosine 3',5'-cyclic monophosphate (db cAMP) is an analogue of cAMP which is present in a preferred embodiment of the subject invention. Except for adenosine, the UW solution does not contain those vasodilators. Experimental results, to be later described, show that the subject invention improves survival of preserved rat hearts over that of the UW solution, thus demonstrating that the subject invention is more effective.

Preferred vasodilators possess other activities in addition to vasodilation. Such activities include at least one, and more preferably all of the following: regulation of endothelial permeability, inhibition of platelet aggregation, and inhibition of neutrophil accumulation. For example, as described more fully in the Experimental Details which follow, the vasodilator hydralazine caused greater vasodilation than nitroglycerin but was less effective in improving recipient survival. It has been reported that stimulants of cAMP activity in endothelium enhance the barrier to macromolecular flux. (Stelzner, et al., J. Cellular Physiology (1989) 139: 157–166.) However, it was not expected that this activity would be useful in organ preservation.

In the subject invention, the use of sodium ion, chloride ion, and calcium ion is specifically avoided. The UW solution, in contrast, contains calcium ion and chloride ion in the form of calcium chloride, and contains sodium ion in the form of sodium gluconate. (U.S. Pat. No. 4,798,824). The modified Collins solution also contains sodium ion in the form of sodium bicarbonate, and chloride ion in the form of hydrochloric acid. (Maurer, E. J., et al., supra; Swanson, et al. supra).

A preferred embodiment of subject invention also contains an agent that prevents calcium entry into cells. The UW solution, in contrast, does not contain an agent that prevents calcium entry into cells.

Both the subject invention and the UW solution contain macromolecules. However, in the subject invention dextran may be used. The patent for the UW solution, in contrast, teaches away from the use of dextran as a macromolecule. (See U.S. Pat. No. 4,798,824, col. 2, lines 15–24, which refers to the macromolecule as a colloid).

Another difference is that a preferred embodiment of the subject invention contains N-acetylcysteine, whereas the UW solution does not contain N-acetylcysteine. The present invention does not contain glutathione, while the UW solution does. During organ preservation, glutathione is lost from the organ. However, it is now known that glutathione in solution does not enter easily into the cell. N-acetylcysteine, however, can enter cells more easily, and is believed to be an agent that helps cells produce glutathione.

Another difference between the subject invention and the modified Collins organ preservation solutions is the choice of buffer. Because basal metabolism results in the generation of acid (the pH of the organ preservation solution can decline during storage), a phosphate buffering system (monopotassium phosphate ($KH_2PO_4$)) is used in a preferred embodiment of the subject invention. The subject invention specifically avoids the use of a bicarbonate buffer. The subject invention has the advantage over other organ preservation solutions that use a bicarbonate buffering system, because a bicarbonate buffering system poses the problem of carbon dioxide removal during buffering. A bicarbonate buffer is used in the modified Collins solution (Maurer, E. J., et al. supra; Swanson, et al. supra).

The initial pH of a preferred embodiment of the subject invention is to the alkaline side of normal physiologic pH so that the average pH during storage remains physiologic. Normal physiologic pH is about 7.4. In other organ preservation solutions that start at or near a physiologic pH, an organ would spend the bulk of a prolonged storage period in a state of acidosis. For instance, the University of Wisconsin solution claims a pH range of 7.4–7.5. In contrast, a preferred embodiment of the subject invention has an initial pH range of about 7.4 to about 7.6.

An investigation of the literature reveals no teaching or suggestion for the use of analogues of adenosine 3',5'-cyclic monophosphate (cyclic adenosine monophosphate, cyclic-AMP, or cAMP), or analogues of guanosine 3',5'-cyclic monophosphate (cyclic guanosine monophosphate, cyclic-GMP, or cGMP), in an organ preservation solution, although there have been studies investigating the effectiveness of various organ preservation solutions. (See, e.g., Okouchi, Yasumitsu, et al., Journal of Thoracic and Cardiovascular Surgery, (1990), vol. 99, pages 1104–1108; Maurer, E. J., et al., supra; Swanson, et al. supra). There has also been significant research into the biochemical mechanisms involved in the metabolic changes associated with myocardial ischemia and reperfusion. (See, e.g., Pasque, Michael K., and Wechsler, Andrew S., Annals of Surgery, (1984), vol. 200, pages 1–12; Nozaki, Hirofumi, and Okuaki, Akira, Tohoku Journal of Experimental Medicine, (1975), vol. 115, pages 145–154; Ogawa, S. et al., American Journal of Physiology, (1992), vol. 262, pages C546–C554).

Such research has shown that endothelial cell monolayers lose their integrity when exposed to hypoxia, which simulates a significant component of ischemia. Following a twelve hour exposure of an aortic endothelial cell monolayer to hypoxia, the monolayer is disrupted, and large gaps form between cells. The "leakiness" of the monolayer can be evaluated by the transfer of various sized radioactive compounds across it, and it is clear that this "leakiness" increases as duration of hypoxic exposure increases. (See, e.g., Ogawa, S. et al., supra). Thus the barrier function of the monolayer is lost.

This loss of endothelial cell barrier function parallels a decline in intracellular adenosine 3',5'-cyclic monophosphate (cyclic adenosine monophosphate, cyclic-AMP, or cAMP) levels. (See, e.g., Pasque, Michael K., and Wechsler, Andrew S., supra; Ogawa, S. et al., supra). Experiments have shown that this hypoxia-induced increase in endothelial cell permeability could be abrogated by maneuvers designed to increase intracellular cyclic-AMP concentration, such as the addition of pertussis toxin. (See, e.g., Ogawa, S. et al., supra). Experiments have also shown that the addition of cyclic-AMP analogues could restore the integrity of the endothelial cell monolayer to solutes of various sizes. (See, e.g., Nozaki, Hirofumi, and Okuaki, Akira, supra; Ogawa, S. et al., supra). Apparently, cyclic-AMP can not penetrate the cell membrane as easily as analogues of cyclic AMP. Dibutyryl adenosine 3',5'-cyclic monophosphate (db cAMP), is an analogue of cyclic-AMP. (See, e.g., Nozaki, Hirofumi, and Okuaki, Akira, supra).

None of that research has disclosed or suggested the use of analogues of cAMP or of cGMP for use in an organ preservation or maintenance solution. Analogues of cAMP or of cGMP that are permeable to the cell membrane can be used in the subject invention.

Analogues of cAMP are believed both to serve as a vasodilator, and to help maintain endothelial integrity. Analogues of cGMP, however, are believed to function as a vasodilator, while their role in helping to maintain endothelial integrity is presently less certain. Hence, the subject invention may use analogues of cGMP as vasodilators. But a preferred embodiment of the subject invention includes analogues of cAMP, because analogues of cAMP are believed to serve both as a vasodilator and to help maintain endothelial cell integrity. Hence, a preferred embodiment of the invention contains db cAMP, which is an analogue of cAMP. It is believed that analogues of cAMP may enhance endothelial barrier function during cold ischemia, which is a step during organ preservation, thereby improving organ function following preservation. Other chemical or physiological mechanisms may be involved.

The present invention provides an aqueous solution for organ preservation or maintenance, comprising: a vasodilator in an amount sufficient to maintain vascular homeostasis; D-glucose in an amount sufficient to support intracellular function and maintenance of cellular bioenergetics; magnesium ions in an amount sufficient to support intracellular function and maintenance of cellular bioenergetics; macromolecules of molecular weight greater than 20,000 daltons in an amount sufficient to maintain endothelial integrity and cellular viability; potassium ions in a concentration greater than about 110 mM; and a buffer in an amount sufficient to maintain the average pH of the organ preservation or maintenance solution during the period of organ preservation at about the physiologic pH value.

The invention also provides a method of preserving or maintaining an organ, comprising contacting the organ with the solution for organ preservation or maintenance.

BRIEF DESCRIPTION OF THE DRAWINGS

FIGS. 7A–G. Nitric oxide was measured by its ability to inhibit platelet aggregation and serotonin release[11]. (A) Platelets aggregate in response to thrombin challenge (arrow). (B) This response is inhibited by the presence of normoxic ECs. (C) Hemoglobin prevents the antiaggregatory effect of ECs by quenching available nitric oxide. (D) ECs exposed to 16 hours of hypoxia showed minimal reduction in antiaggregatory effect (indicating preserved NO generation), whereas (E) HUVECs exposed to 16 hours of hypoxia followed by 15 minutes of reoxygenation fail to inhibit platelet aggregation. (F) Superoxide dismutase restores the antiaggregatory effect of reoxygenated ECs, indicating the potential role of free-radicals in quenching available NO generated by the reoxygenated ECs. (G) Bar Graph: Conditions are as indicated above, with platelet aggregation quantified by $^{14}C$-serotonin release. Bar E represents ECs reoxygenated from 10–95 minutes. Peak NO quenching was noted at 10–15 minutes reoxygenation. ($p<0.01$ by ANOVA for; platelets alone vs platelets+either normoxic or hypoxic ECs; hypoxic vs reoxygenated ECs; and reoxygenated ECs with vs without SOD).

FIG. 16A) or EC supplemented with nitroglycerin (NTG; 0.1 mg/mL, FIG. 16B) after the native lung was removed from the pulmonary circulation as described. PAP=mean pulmonary arterial pressure (mm Hg); PAF= pulmonary arterial flow (mL/min); PVR= pulmonary vascular resistance ($\times 10^{-3}$ Woods unit)

DETAILED DESCRIPTION OF THE INVENTION

Figure 1A:
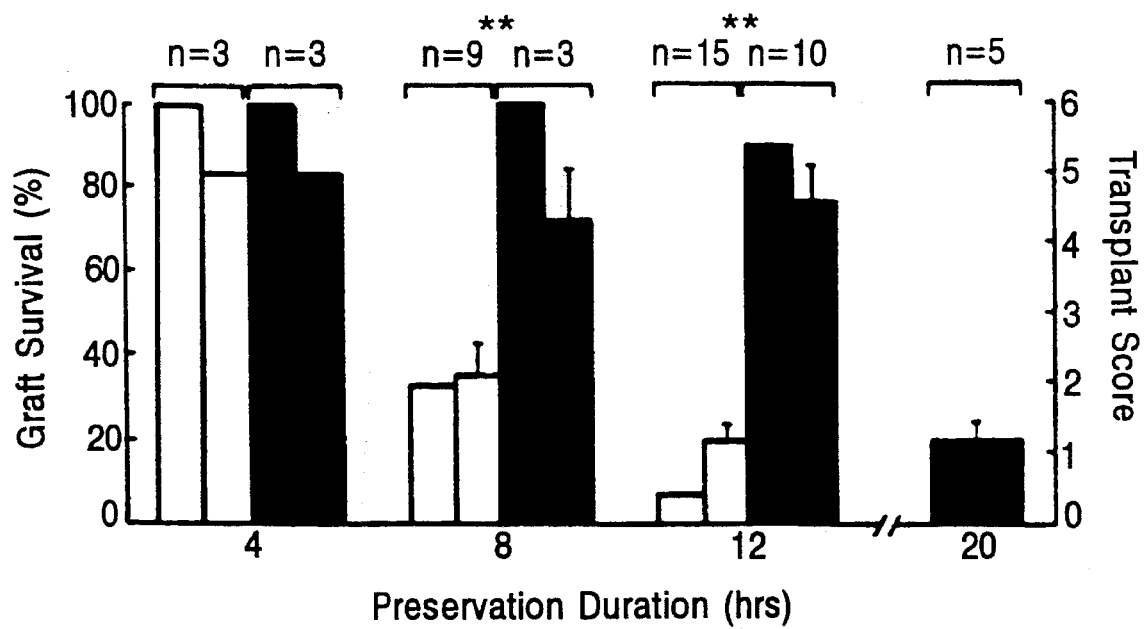
FIGS. 1A–B. Effect of db-cAMP on cardiac preservation in LR. (A) Dependence on preservation time. Hearts were explanted, flushed with cold LR alone (open bars) or LR+db-cAMP (4 mM; closed bars), and then stored in the same solution at 4° C. for the indicated times. Data are reported (as described in the text) as percent survival (left bar) or transplant score (right bar), both assessed at 10 min following release of the aortic cross-clamp. Db-cAMP prolongs the duration of preservation that is associated with subsequent successful transplantation. (B) Dependence on db-cAMP concentration in the preservation solution. Hearts were explanted and stored for 12 hrs as above in LR supplemented with the indicated concentration of db-cAMP (mM). The percent survival (left bar) and cardiac score (right bar) are shown. N is indicated for each point. Note that the 12 hour control preservation group (LR) displayed in these panels is also shown in FIG. 2 for illustrative purposes; the nonparametric analysis of variance (see methods) takes this into account in calculating significance of the data. [** denotes $p<0.01$, LR+db-cAMP vs LR alone]

The present invention provides an aqueous solution for organ preservation or maintenance, comprising: a vasodilator in an amount sufficient to maintain vascular homeostasis; D-glucose in an amount sufficient to support intracellular function and maintenance of cellular bioenergetics; magnesium ions in an amount sufficient to support intracellular function and maintenance of cellular bioenergetics; macromolecules of molecular weight greater than 20,000 daltons in an amount sufficient to maintain endothelial integrity and cellular viability; potassium ions in a concentration greater than about 110 mM; and a buffer in an amount sufficient to maintain the average pH of the organ preservation or maintenance solution during the period of organ preservation at about the physiologic pH or above.

This invention concerns an organ preservation or maintenance solution that can preserve an organ wherein the organ is an organ intended for transplantation. For example, the organ intended for transplantation may be a heart or a lung. While experimental work for this invention has focused on the heart and lung, the organ preservation or maintenance solution may be used for other organs, and for tissues and cells as well, because the same principles of organ preservation apply. Such organs include, but are not limited to, the following: brain, kidney, pancreas, intestine, skin and muscle.

The organ preservation or maintenance solution can also be used for maintaining organs during surgery, because the principles of organ preservation apply. For example, the organ preservation or maintenance solution may be used during cardiac, or open heart, surgery, as a cardioplegic solution. Other uses of the subject invention may be obvious to those skilled in the medical profession.

In general, the principles of organ preservation recognize that organ viability must be maintained at two different levels during and after preservation: at the tissue level, and at the cellular level.

At the tissue level, vascular integrity must be maintained so that tissue architecture, nutrient delivery, and toxin removal are nearly normal. As described below, a preferred embodiment of the organ preservation solution contains analogues of adenosine 3',5'-cyclic monophosphate (cyclic adenosine monophosphate, cyclic-AMP, or cAMP), such as db cAMP, which help maintain endothelial integrity in conditions of hypoxia, such as during preservation, and are also believed to be important for the reperfusion period. It is believed that analogues of cAMP may enhance endothelial barrier function during cold ischemia, which is a step during organ preservation, thereby improving organ function following preservation. The analogues of adenosine 3',5'-cyclic monophosphate probably also function as vasodilators. Dibutyryl adenosine 3',5'-cyclic monophosphate (db cAMP), which is an analogue of adenosine 3',5'-cyclic monophosphate, is present in a preferred embodiment. Analogues of cAMP are believed both to serve as a vasodilator, and to help maintain endothelial cell integrity.

Analogues of cGMP, however, are believed to function as a vasodilator, while their role in helping to maintain endothelial cell integrity is presently less certain. Hence, the subject invention may use analogues of cGMP as vasodilators. But a preferred embodiment includes analogues of cAMP, because analogues of cAMP serve both as a vasodilator and to help maintain endothelial cell integrity. Other chemical or physiological mechanisms may be involved.

Other components also help maintain vascular integrity. Macromolecules of molecular weight greater than 20,000 daltons help plug small endothelial leaks which may occur, preventing extravasation of intravascular contents into the pericellular space. An anticoagulant, which is present in a preferred embodiment, helps prevent thrombosis during or after preservation, so that nutrient delivery and toxin removal can proceed. Vasodilators, such as analogues of adenosine 3',5'-cyclic monophosphate, analogues of guanosine 3',5'-cyclic monophosphate, nitroglycerin, or adenosine are probably also important for similar reasons, so that vascular homeostasis can be re-achieved rapidly following reimplantation.

The principles of organ preservation also suggest that maintenance of cellular viability is likewise important to proper organ function following transplantation. In that regard, the organ preservation or maintenance solution contains a macromolecule of molecular weight greater than 20,000 daltons, which helps prevent cellular swelling and rupture during the preservation and recovery periods. The macromolecule of molecular weight greater than 20,000 daltons includes colloids. Also, the osmolarity of the organ preservation must be greater than the cellular osmolarity. The organ preservation or maintenance solution also contains D-glucose and magnesium ions, because basal energy metabolism (even during hypothermia) can be supported by the anaerobic metabolism of glucose, and the presence of magnesium ions allows for the proper functioning of the enzymes needed for adenosine triphosphate (ATP) synthesis. Adenosine is also present in a preferred embodiment, since adenosine may be a substrate for ATP synthesis. A preferred embodiment also contains antioxidants or reducing agents, since following reperfusion, highly toxic oxygen radicals are known to be formed, and the addition of such agents help serve to mute the lethal effects of these radicals during the vulnerable period immediately following reestablishment of blood flow. A preferred embodiment also contains an agent that helps prevent calcium entry into cells, because it is also well known that calcium accumulation within a cardiac myocyte can be injurious or lethal following reperfusion. Hence, the organ preservation or maintenance solution does not contain calcium, and a preferred embodiment contains an agent that helps prevent calcium entry into cells.

The organ preservation or maintenance solution comprises a vasodilator in an amount sufficient to maintain vascular homeostasis. The vasodilator can be selected from the group consisting of phosphodiesterase inhibitors, analogues of adenosine 3',5'-cyclic monophosphate (cyclic adenosine monophosphate, cyclic-AMP, or cAMP), analogues of guanosine 3',5'-cyclic monophosphate (cyclic guanosine monophosphate, cyclic-GMP, or cGMP), nitroglycerin, or adenosine. Suitable combinations of the vasodilators may be used. A preferred embodiment contains a vasodilator, wherein the vasodilator is dibutyryl adenosine 3',5'-cyclic monophosphate (db cAMP), alone or in combination with nitroglycerin and adenosine.

In another preferred embodiment, the vasodilator is a phosphodiesterase inhibitor. In a specific embodiment the phosphodiesterase inhibitor is selected from the group consisting of isobutylmethylxanthine, indolidan, rolipram, 2-o-propoxyphenyl-8-azapurin-6-one (M&B 22948; Zaprinast), trequensin, amrinone, milrinone, aminophylline, and dipyridamole.

In addition to their vasodilatory activity, phosphodiesterase inhibitors reduce the leakiness of endothelial cells, decrease platelet aggregation, and decrease neutrophil accumulation.

PDE inhibitors are often more desirable than nitroglycerin as a vasodilator. First, many PDE inhibitors have specificity which can be used to target specific organs or cells. For example, Zaprinast is preferred when stimulation of cGMP is desired. Indolidan or rolipram increase intracellular cAMP. Amrinone and milrinone possess specificity for heart tissue. Nitroglycerin, in contrast, targets all tissues. Second, use of PDE inhibitors avoids a number of well-known undesirable side-effects associated with nitroglycerin.

Phosphodiesterase (PDE) inhibitors are commonly categorized according to five families (See, W. J. Thompson, Pharmac. Ther. (1991) 51: 13–33; and J. P. Hall, Br. J. clin. Pharmac. (1993) 35: 1–7) (However, this classification is not universal and other classification schemes can be found in the literature.): PDE I— $Ca^{+2}$/Calmodulin-activatable; PDE II—cGMP activatable; PDE III—cGMP inhibitable; PDE IV—cAMP-specific; PDE V—cGMP-specific. These families include, but are not limited to, the following phosphodiesterase inhibitors:

Family I - calmodulin antagonists (e.g., phenothiazines, W-7, CGS 9343B), vinpocetine (TCV-3B), HA-558, 8-methoxymethyl-3-isobutyl-1-methylxanthine, KW-6 (isoquinoline derivative, 8-methylamino-3-isobutyl-1-methylxantine (MIMAX), and dibenzoquinazoline diones (Dihydroisoquinoline derivative.

Family II - Trequinsin (HL 725).

Family III - Indolidan (LY 195115), Cilostamide (OPC 3689), Lixazinone (RS 82856), Y-590, Imazodan (CI 914), SKF 94120, Quazinone, ICI 153,110, Cilostazol (OPC 13013), Bemorandan (RWJ 22867), Siguazodan (SK&F 94836), Adibendan (BM 14,478), Milrinone (WIN 47203), Enoximone (MDL 17043), Pimobendan (UD-CG 115, MCI-154), Saterinone (BDF 8634), and Sulmazole (ARL 115).

Family IV - Rolipram (ZK 62711; Pyrrolidone), RO 20-1724 (Imidazoiidinone), SQ 64442 (Etazoiate), and Denbufylline (BRL 30892).

Family V - Zaprinast (M&B 22948), and Dipyridamole (DSCG).

Recent experiments have shown that some vasodilators are more effective than others. In particular, recent experiments have shown that analogues of adenosine 3',5'-cyclic monophosphate and nitroglycerin are important; but that the organ preservation or maintenance solution will function without the presence of adenosine. A preferred embodiment, however, contains adenosine. (See Experimental section).

Further recent experiments suggest that the organ preservation and maintenance solution may function without the presence of db cAMP, so long as the solution contains nitroglycerin. (See Experimental section). It is believed, however, that the solution functions more effectively with the presence of db cAMP in addition to the nitroglycerin. Though it is difficult to access the relative importance of the individual components of the organ preservation and maintenance solution, the presence of vasodilators is clearly important.

The analogues of adenosine 3',5'-cyclic monophosphate can be selected from the group consisting of dibutyryl adenosine 3',5'-cyclic monophosphate (db cAMP), or 8-bromoadenosine 3,'5'-cyclic monophosphate. As mentioned earlier, other suitable analogues of cAMP may be used.

Experiments have shown that adenosine 3',5'-cyclic monophosphate (cyclic-AMP, or cAMP) has difficulty entering the cell membrane, but that analogues of cAMP are more permeable. Experiments also have shown that it is the cAMP portion of the molecule that exerts a beneficial effect. (See Experimental section). Hence, other analogues of cAMP or of cGMP which can enter the cell membrane can be used.

Vasodilators are important for ensuring that thrombosis does not occur during or after preservation, so that nutrient delivery and toxin removal can proceed. Vasodilators thus help vascular homeostasis to be reachieved rapidly following re-implantation. Recent evidence indicates that adenosine may act via the adenosine receptor (causing vasodilation) to minimize damage following experimental canine myocardial infarction and reperfusion. In fact, the major salutary role of db cAMP in organ preservation or maintenance may be via its actions as a vasodilator. Vasodilators are likely to be necessary if vasospasm plays any role in the post-implantation period, as it likely does.

Analogues of cAMP are believed to make hearts, and other organs, less susceptible to reperfusion injury. The addition of such analogues of cAMP help serve to maintain endothelial integrity in conditions of hypoxia (such as during preservation), as well as during reperfusion.

Db cAMP is an example of an analogue of cAMP which can be used in the organ preservation or maintenance solution. The optimal concentration of db cAMP is about 2 mM, though the solution functions with db cAMP concentrations of about 1 mM, and of about 2 to 4 mM. (See Experimental section). Experiments have shown, however, that db cAMP concentrations higher than about 4 mM become toxic to endothelial cells. Hence, 2 mM is considered to be the optimal concentration of db cAMP. In a preferred embodiment, the concentration of dibutyryl adenosine 3',5'-cyclic monophosphate (db cAMP) ranges from about 1 mM to about 4 mM.

The organ preservation or maintenance solution may also comprise nitroglycerin. In a preferred embodiment, the concentration of nitroglycerin ranges from about 0.05 g/l to about 0.2 g/l.

The organ preservation or maintenance solution may also comprise adenosine in a preferred embodiment, the concentration of adenosine ranges from about 3 mM to about 20 mM.

The organ preservation or maintenance solution also comprises D-glucose in an amount sufficient to support intracellular function and maintenance of cellular bioenergetics. In a preferred embodiment, the concentration of D-glucose ranges from about 50 mM to about 80 mM.

The organ preservation or maintenance solution also comprises magnesium ions in an amount sufficient to support intracellular function and maintenance of cellular bioenergetics. In a preferred embodiment, the concentration of magnesium ions ranges from about 2 mM to about 10 mM. The magnesium ions are derived from the group consisting of magnesium sulfate, magnesium gluconate, or magnesium phosphate, or suitable combinations thereof. The magnesium ions can be derived from some other suitable magnesium containing compound. D-Glucose, adenosine, and magnesium ions are substrates for adenosine triphosphate (ATP) synthesis. Metabolic substrates such as D-glucose and perhaps adenosine for ATP formation are probably important for maintaining the small degree of anaerobic metabolism that occurs. Basal energy metabolism (even during hypothermia) can be supported by the anaerobic metabolism of D-glucose. The presence of magnesium ion allows for the proper functioning of the enzymes needed for adenosine triphosphate (ATP) synthesis. In general, substrates for ATP synthesis are helpful to allow intracellular function and maintenance of cellular bioenergetics.

The organ preservation or maintenance solution also comprises macromolecules of molecular weight greater than 20,000 daltons in an amount sufficient to maintain endothelial integrity and cellular viability. In a preferred embodiment, the macromolecule of molecular weight greater than 20,000 daltons is selected from the group consisting of macromolecules having a molecular weight greater than about 100,000 daltons, a polysaccharide, or a polyethylene glycol. Other suitable macromolecules can be used. The macromolecule of molecular weight greater than 20,000 daltons can include colloids.

In a preferred embodiment, the polysaccharide is a dextran. Furthermore, in a preferred combination, the dextran is a dextran molecule having a molecular weight of 308,000 daltons.

It is difficult to define an upper limit to the molecular weight of the macromolecule of molecular weight greater than 20,000 daltons. For instance, the macromolecule can be dextran, having a molecular weight of 308,000 daltons.

Macromolecules of molecular weight greater than 20,000 daltons are believed to be helpful in reducing trans-endothelial leakage and subsequent intracellular and interstitial edema in the reperfusion period, by serving to plug small endothelial leaks which may occur. Macromolecules may thus also prevent the extravasation of intravascular contents into the pericellular space, thus helping to prevent cellular swelling and rupture during the preservation and recovery periods.

The osmolarity of the organ preservation or maintenance solution is also a factor in helping to prevent cellular swelling and rupture. The osmolarity of the organ preservation or maintenance solution must be greater than the cellular osmolarity. Cellular osmolarity is about 290 mOsm/l. In a preferred embodiment, the osmolarity ranges from about 315 mOsm/l to about 340 mOsm/l.

The organ preservation or maintenance solution also comprises potassium ions in a concentration greater than about 110 mM. The potassium ions are derived from the group consisting of potassium sulfate, potassium gluconate, monopotassium phosphate ($KH_2PO_4$), or suitable combinations thereof. The potassium ions may be derived from some other suitable potassium containing compound. In a preferred embodiment, the concentration of potassium ions ranges from about 110 mM to about 140 mM.

The design of the solution encompasses the need for a high potassium concentration, similar to intracellular levels, as this aids both in the cardioplegic aspects of the solution and has been shown to enhance myocardial viability following cold potassium cardioplegia.

The organ preservation or maintenance solution also comprises a buffer in an amount sufficient to maintain the average pH of the organ preservation or maintenance solution during the period of organ preservation at about the physiologic pH value. In a preferred embodiment, the buffer is monopotassium phosphate ($KH_2PO_4$). However, other suitable buffers may be used.

The buffering capacity must be adequate to buffer the organic acids that accrue during ischemia. Because basal metabolism results in the generation of acid, a buffering system is used. The pH of the organ preservation or maintenance solution declines during the prolonged storage times that can be employed with this solution. A bicarbonate buffering system, however, is not used in the subject invention because a bicarbonate buffer would release carbon dioxide, which would have to be removed.

In a preferred embodiment, the initial pH of the organ preservation or maintenance solution is adjusted to the alkaline side of normal physiologic pH because then the average pH during storage of the organ in the organ preservation or maintenance solution remains physiologic. Normal physiologic pH is about 7.4. A preferred embodiment of the organ preservation or maintenance solution has a pH range of about 7.4 to about 7.6. The pH may be adjusted to the desired value with the addition of a suitable base, such as potassium hydroxide (KOH). Hence, during the period of organ preservation, the pH of the organ preservation or maintenance solution starts on the alkaline side of physiologic pH, and may drift slowly down to the acidic side of physiologic pH. But the average pH of the organ preservation or maintenance solution during the period of organ preservation is about the physiologic value.

The organ preservation or maintenance solution may further comprise impermeant anions in an amount sufficient to help maintain endothelial integrity and cellular viability. The impermeant anion is selected from the group consisting of the gluconate anion or the lactobionate anion. Other suitable impermeant anions can be used. In a preferred embodiment, the concentration of the gluconate anion ranges from about 85 mM to about 105 mM. The gluconate anion is derived from the group consisting of potassium gluconate or magnesium gluconate. The gluconate anion may be derived from some other suitable gluconate containing compound.

Impermeant anions are large anions that cannot cross cell membranes, so that sodium is at least in part prevented from diffusing down its concentration gradient into the cell during the preservation period. Impermeant anions thus help to prevent cellular edema.

The organ preservation or maintenance solution may further comprise an anticoagulant in an amount sufficient to help prevent clotting of blood within the capillary bed of the organ. The anticoagulant is selected from the group consisting of heparin or hirudin. Other suitable anticoagulants may be used. In a preferred embodiment, the concentration of heparin ranges from about 1000 units/l to about 100,000 units/l.

Anticoagulants are believed to help in preventing clotting of blood within the capillary bed of the preserved organ. Specifically, anticoagulants are believed to help prevent a total organ no-reflow phenomenon at the level of the microcirculation, which would be undesirable following re-implantation and could result in graft failure. Anticoagulants are believed to be helpful in ensuring that thrombosis does not occur during or after preservation, so that nutrient delivery and toxin removal can proceed.

The organ preservation or maintenance solution may further comprise an antioxidant in an amount sufficient to help decrease reperfusion injury secondary to oxygen free radicals. The antioxidant is selected from the group consisting of butylated hydroxyanisole (BHA), butylated hydroxytoluene (BHT), Vitamin C, Vitamin E, or suitable combinations thereof. Other suitable antioxidants may be used. In a preferred embodiment, the antioxidant is butylated hydroxyanisole (BHA) at a concentration range from about 25 microM to about 100 microM, alone or in combination with butylated hydroxytoluene (BHT) at a concentration range from about 25 microM to about 100 microM.

The organ preservation or maintenance solution may further comprise a reducing agent in an amount sufficient to help decrease reperfusion injury secondary to oxygen free radicals. Any suitable reducing agent can be used.

The organ preservation or maintenance solution may further comprise N-acetylcysteine in an amount sufficient to help cells produce glutathione. In a preferred embodiment, the concentration of N-acetylcysteine ranges from about 0.1 mM to about 5 mM.

N-acetylcysteine is an agent which can enter cell and is believed to play a role in helping cells to produce glutathione, which is a reducing agent. During organ preservation, glutathione is lost from the organ. Simply adding glutathione to the organ preservation or maintenance solution, however, would be of little to no help, because it is now known that glutathione in solution does not enter easily into the cell.

The organ preservation or maintenance solution may further comprise an agent that helps prevent calcium entry into cells in an amount sufficient to help prevent calcium entry into cells. Agents that help prevent calcium entry into cells include so-called calcium channel blockers, as well as other agents that serve the described function. An agent that helps prevent calcium entry into cells is verapamil. Other suitable agents that help prevent calcium entry into cells may be used. In a preferred embodiment, the concentration of verapamil ranges from about 2 microM to about 25 microM.

Agents that help prevent calcium entry into cells are believed to play a role in preventing calcium overload as a cause for myocyte death during and after preservation. It is also well known that calcium accumulation within a cardiac myocyte can be injurious or lethal following reperfusion. Hence, the organ preservation or maintenance solution specifically does not contain calcium.

The absence of sodium in the organ preservation or maintenance solution is also by design, because any sodium which may enter the cells during the period of preservation (when energy currency is low and the normal trans-cellular gradient may not be well maintained) may 1) lead to cellular swelling, 2) cause calcium entry by facilitated diffusion (following re-implantation), and 3) sodium load the cell and hence depolarize it during storage, such that a high amount of energy is required following reestablishment of blood flow before a normal membrane potential can be re-established. In fact, sodium loading is well described during hypothermic storage of organs.

Electrolyte concentrations must be adjusted to reduce transmembrane flux of electrolytes. The absence of chloride in the organ preservation or maintenance solution is also by design. Sodium, chloride, and calcium are avoided.

The organ preservation or maintenance solution may further comprise a bacteriostat in an amount sufficient to help inhibit the growth of, or destroy, bacteria. The bacteriostat is selected from the group consisting of cefazolin or penicillin. Other suitable bacteriostats or antibiotics can be used. In an embodiment, the concentration of cefazolin ranges from about 0.25 g/l to about 1 g/l.

The addition of an antibiotic to the organ preservation or maintenance solution is purely a surgical consideration, due to the practical inability of sterilizing the solution completely, as the high molecular weight solutes would not pass through a 0.2 micron membrane filter which is used in the preparation of the organ preservation or maintenance solution. It is believed that gamma irradiation may be used to better sterilize the solution. The possible use of gamma irradiation for sterilization will require experimental investigation.

The invention also provides a method of preserving or maintaining an organ, comprising contacting the organ with the solution for organ preservation or maintenance. The contacting comprises immersion, infusion, flushing, or perfusion. Other suitable procedures of contacting are included. The method can be used wherein the organ is an organ intended for transplantation. The method can be used wherein the organ is a heart. For example, the method can be used wherein the heart is involved in cardiac surgery. Hence, the organ preservation or maintenance solution may be used in organ transplantation procedures. The organ preservation or maintenance solution may also be used during certain other surgical or medical procedures; for example, the solution may be used as a cardioplegic agent during cardiac surgery.

Experiments involving the organ preservation or maintenance solution have involved the heart. However, it is anticipated that similar principles of organ preservation apply to other organs as well, such that the organ preservation or maintenance solution might be used successfully to preserve livers, pancreases, kidneys, lungs, etc. For instance, a preliminary and recent experiment has been performed involving the transplantation of a single baboon lung wherein the lung was preserved in the solution for twenty-two hours. (See Experimental section). In general, the organ preservation or maintenance solution may be used for cells and tissues, as well as for organs. That is, the organ preservation or maintenance solution may be used for those situations that require cell viability.

In addition, the principles of organ preservation apply to cardioplegic agents used to arrest the heart during cardiac surgery, so that the organ preservation or maintenance solution may have a role as a cardioplegic agent independent of transplant surgery. The solution may also be used for other medical procedures. Because myocardial infarction also involves ischemic (and often reperfusion) phases, there is a potential role for the organ preservation or maintenance solution for myocardial salvage following infarction, thrombolysis, or complicated angioplasty. The organ preservation or maintenance solution thus provides a clear advantage over other organ preservation solutions designed to date, and the principles involved in its design likely apply to a host of important clinical situations.

The composition of the organ preservation or maintenance solution might have to be adjusted according to the type of organ being transplanted, or to accommodate certain other surgical, medical, or other considerations. The composition of the organ preservation or maintenance solution might also be different when the solution is being used as a cardioplegic agent in cardiac surgery, or in some other appropriate surgical procedure, than when the solution is being used for organ transplantation. The composition might also require adjustment depending upon certain other circumstances. For instance, the composition might have to be varied depending upon whether the organ is being transported or is in idle storage, the distance of the transportation, the time of transportation, the temperature during storage or transportation, and other factors. Such variations or adjustments in the composition of the organ preservation or maintenance solution which might be required would be obvious to those skilled in organ transplantation or surgical procedures.

The amount of the organ preservation or maintenance solution required in an organ transplantation or surgical procedure (such as a cardioplegic agent during cardiac surgery) would be obvious to one who is skilled in such organ transplantation or surgical procedures.

The organ preservation or maintenance solution is suitable for use at the low temperatures that may be required during an organ transplantation or other surgical procedure. For instance, temperatures of about zero to about four degrees Centigrade may be required during an organ transplantation or surgical procedure.

A preferred embodiment of the subject invention consists of the following ingredients in the amounts specified:
D-Glucose, 67.4 mM
Magnesium Sulfate ($MgSO_4$), 5 mM
Monopotassium Phosphate ($KH_2PO_4$), 25 mM
Dextran (molecular weight 308,000 daltons), 50 g/l
Potassium Gluconate (K-Gluconate), 95 mM
Butylated Hydroxyanisole (BHA), 50 microM
Butylated Hydroxytoluene (BHT), 50 microM
N-Acetylcysteine (N-AC), 0.5 mM
Adenosine, 5 mM
Nitroglycerin, 0.1 g/l
Verapamil, 10 microM
Dibutyryl Adenosine 3',5'-Cyclic Monophosphate {Dibutyryl cAMP, db cAMP), 2 mM
Heparin, 10,000 units/l
Cefazolin, 0.5 g/l
The pH is adjusted to 7.6 with Potassium Hydroxide (KOH).

The organ preservation or maintenance solution is an aqueous solution.

A method of preparing the organ preservation or maintenance solution is described in the Experimental Details section.

Certain embodiments of the invention are set forth in the Experimental Details section which follows. The Experimental Details section is provided to aid in an understanding of the invention but is not intended to, and should not be construed to, limit in any way the invention as set forth in the claims which follow thereafter.

EXPERIMENTAL DETAILS

FIRST SERIES OF EXPERIMENTS

Experiment One:

In Experiment One, a heterotopic rat heart transplant model is used [Okouchi, Yasumitsu, et al., Journal of Thoracic and Cardiovascular Surgery, vol. 99 (1990), pages 1104–1108 (heterotopic rat heart transplant model)] to examine the comparative effectiveness of the organ preservation or maintenance solution of the subject invention.

MATERIALS AND METHODS

The following reagents were obtained from the indicated commercial sources; D-glucose, magnesium sulfate, dextran (M.W. 308,000 daltons), monopotassium phosphate ($KH_2PO_4$), potassium gluconate, adenosine, butylated hydroxyanisole (BHA), butylated hydroxytoluene (BHT), N-acetylcysteine (N—AC), and heparin (porcine intestinal, 100000 u/g) were obtained from Sigma Chemical Company (St. Louis, Mo.). Dibutyryl adenosine 3',5'-cyclic monophosphate (dibutyryl cyclic AMP, or db cAMP) was obtained from Aldrich Chemical Company, Incorporated (Milwaukee, Wis.). Verapamil (2.5 mg/ml) was obtained from Knoll Pharmaceutical Co. Nitroglycerin (5 mg/ml) was obtained from DuPont (Manati, Puerto Rico). Cefazolin (400 mg/ml) was obtained from Lyphomed (Rosemont, Ill.).

Lactated Ringer's solution was obtained from Abbott (North Chicago, Ill.).

Columbia University solution is made by adding 67.4 mM D-glucose, 5 mM magnesium sulfate ($MgSO_4$), 95 mM potassium gluconate, 25 mM monopotassium phosphate ($KH_2PO_4$), and 10 units/ml of heparin to double distilled water. The pH is then adjusted to about 7.6 with 10 M potassium hydroxide (KOH). The solution is then filtered with a 0.2 micron filter. Dextran (50 g/l) (molecular weight 308,000 daltons) is added with gentle stirring for 24 hours at 4° C. to aid dissolution and to help de-bubble the mixture. On the morning of use, cefazolin (0.5 mg/ml), adenosine (5 mH), nitroglycerin (0.1 mg/ml), Verapamil (10 microM), BHA (50 μM), BHT (50 μM), N-acetylcysteine (0.5 mH), and db cAMP (2 mM) are added (the BHA and BHT were first dissolved in ethanol at 50 mM to aid solubility).

A heterotopic rat heart transplant model is used to examine the comparative effectiveness of the organ preservation or maintenance solution of the subject invention. The heterotopic rat heart transplant model involves harvesting a heart following cold cardioplegic arrest, and then flushing the aortic root with preservation solution until the coronary arteries become visibly clear. Following a period of preservation, the heart is then transplanted into a recipient rat's abdomen with the aortic root being anastomosed to the recipient's abdominal aorta, and the pulmonary artery being anastomosed to the recipient's inferior vena cava. This permits normal coronary artery perfusion of the transplanted heart following implantation.

Male Sprague-Dawley rats (350–400 gm) were prepared as follows. Each donor rat was anesthetized, shaved, given 1000 units of heparin intravenously (IV), and explanation was begun one (1) minute later. A midline longitudinal incision was made spanning the thorax and abdomen, the suprahepatic inferior vena cava was ligated, and 5 cc of cold cardioplegia (Ringers Lactate (RL) with 40 milliequivalent KCl/l) was administered into the inferior vena cava (IVC). Although Ringer's Lactate solution was used for that purpose in these experiments, the organ preservation or maintenance solution of the subject invention may also be used. A cold saline-soaked gauze was kept over the heart for the following manipulations. The superior vena cava (SVC) was ligated and transected, after which a suture was passed underneath the aortic arch and mainstem pulmonary artery, and looped back under the suprahepatic IVC. The aorta and mainstem pulmonary artery were then transected approximately 4 mm from their respective origins. The suture that had been placed was gathered in a purse-string fashion to encompass all pulmonary veins, which were then ligated. The heart was removed by transecting the IVC and the pulmonary veins, and then rapidly immersed in 4° C. preservation solution. For the purposes of this portion of the experiment, the "preservation solution" here is one of five test solutions: 1) Ringer's Lactate (RL); 2) Ringer's Lactate to which 4 mM of db cAMP is added; 3) University of Wisconsin (UW) solution; 4) University of Wisconsin solution to which 4 mM of db cAMP is added; or 5) the subject invention (Columbia University solution). The aortic root was flushed with preservation solution until the coronaries were clear (approximately 15 ml per heart), and the IVC was again ligated closer to its insertion into the right atrium, and excess tissue trimmed away. The explanted heart was kept immersed in the preservation solution (kept on crushed ice) for the indicated duration of time.

The recipient rat was anesthetized in a similar fashion as the donor, but was not heparinized. A longitudinal midline abdominal incision was performed, and the abdominal aorta and IVC were gathered in a cross-clamp. 8-0 nylon material was used to suture the donor aorta to the recipient aorta, after which the donor pulmonary artery was anastomosed to the recipient IVC in a similar fashion. The donor heart was kept moist with a cold saline-soaked gauze throughout this period of reanastomosis. The duration of preservation was considered to be that from the time of harvest to the time of release of the aortic cross-clamp. The period of warm ischemia, that is, the time from initiation of implantation until release of cross claim was always kept at one (1) hour.

Following release of the aortic cross-clamp, the transplanted hearts are scored from zero to five (worst to best) based on the criteria of turgor [hard (0), average (1), and soft (2)]; color [not-pink (0) and pink (1)]; and contraction [poor (0), average (1), and good (2)]. The worst appearance is when the transplanted hear is not beating, hard, and black. In fact, often the failed transplant can be seen to go from pale immediately out of cold preservation, to pink as the blood perfuses the heart, to black, as the graft becomes non-viable, and this occurs over a period of a few minutes. For this reason, hearts were scored at ten minutes following release of the nortic cross-clamp, to obtain the "Heart Transplant Index." Electrocardiograms (EKG) were also taken at this time to obtain the "Heart Survival Rate." A regular EKG rhythm was necessary for the overall transplant to have been considered a success.

Also examined was a comparison of db cAMP (4 mM) with other agents for cardiac preservation, where those other agents consisted of Na Butyrate (4 mM); 8-Bromoadenosine 3',5'-cyclic monophosphate (4 mM); and 8-Bromoadenosine (4 mM).

Also examined was the effect of the concentration of db cAMP on both Ringer's Lactate and University of Wisconsin solutions.

Finally, Ringer's Lactate solution, University of Wisconsin solution, and University of Wisconsin solution to which db cAMP was added, were compared to the organ preservation or maintenance solution of the subject invention (Columbia University solution) at a preservation time of twenty-eight (28) hours.

DATA

TABLE I

| Comparison of Five Preservation Solutions |||||
|---|---|---|---|---|
| TABLE IA: Effect of db cAMP on Cardiac Preservation in Ringer's Lactate Solution |||||
| Time | RL (A) | RL + dbcAMP (A) | RL (B) | RL + dbcAMP (B) |
| 4 hr | 3/3 | 6/6 | 5 | 5 |
| 8 hr | 1/6 | 3/3 | aprx. 1.5 | 5 |
| 12 hr | 0/9 | 9/9* | 0.8 ± 0.4 | 4.6 ± 1.3* |
| TABLE ID: Effect of db cAMP on Cardiac Preservation in University of Wisconsin Solution |||||
| Time | UW (A) | UW + dbcAMP (A) | UW (B) | UW + dbcAMP (B) |
| 16 hr | 4/6 | 5/5 | aprx. 3.8 | aprx. 4.8 |
| 20 hr | 1/3 | 5/5 | aprx. 2.0 | aprx. 4.7 |
| 24 hr | 3/9* | 9/9 | 1.9 ± 1.4* | 4.7 ± 0.7 |
| 28 hr | 4/9 | 6/10 | 2.4 ± 1.6 | 3.2 ± 1.8 |

TABLE I-continued

Comparison of Five Preservation Solutions

TABLE IC:
Effect of Columbia University Solution on Cardiac Preservation

| Time  | CU (A) | CU (B)    |
|-------|--------|-----------|
| 24 hr | 6/6    | 4.8 ± 0.4 |
| 28 hr | 12/13* | 4.6 ± 0.9 |
| 36 hr | 33.3%  | aprx. 4.6 |

TABLE ID:
Comparison of Ringer's Lactate Solution, University of Wisconsin Solution, and University of Wisconsin Solution to Which db cAMP is Added, With Columbia University Solution (Subject Invention), at Preservation Times of 28 and 36 Hours

| Time  | RL (A) | UW (A) | UW + dbcAMP (A) | CU (A) |
|-------|--------|--------|-----------------|--------|
| 28 hr | zero   | 4/9    | 6/10            | 12/13  |
| 36 hr | —      | —      | —               | 33.3%  |

| Time  | RL (B) | UW (B)    | UW + dbcAMP (B) | CU (B)    |
|-------|--------|-----------|-----------------|-----------|
| 28 hr | zero   | 2.3 ± 1.2 | 3.2 ± 1.2       | 4.6 ± 1   |
| 36 hr | —      | —         | —               | aprx. 4.6 |

In Table I above, the symbols and abbreviations have the following meanings: A is heart survival rate, or function (rhythm on EKG), (# viable/# attempted); B is transplant index, or appearance, based on turgor, color, and contractility, ranging from zero to five (worst to best); hr is time in hours; aprx. is approximately; CU is Columbia University solution (the subject invention); RL is Ringer's Lactate solution; RL+db cAMP is Ringer's Lactate solution to which 4 mM of db cAMP is added; UW is University of Wisconsin solution; UW+db cAMP is University of Wisconsin solution to which 4 mM of db cAMP is added; (*) denotes p is less than 0.05 from other values at same time value ( - - - ) denotes that there is no experimental data.

TABLE II

Comparison of db cAMP with Other Agents For Cardiac Preservation, at Preservation Time of 24 Hours

| Time  | CU (A) | XX (A) | YY (A) | ZZ (A) |
|-------|--------|--------|--------|--------|
| 24 hr | 9/9    | 0/3    | 6/7    | 1/6    |

| Time  | CU (B)  | XX (B)  | YY (B)    | ZZ (B)  |
|-------|---------|---------|-----------|---------|
| 24 hr | aprx. 5 | aprx. 1 | aprx. 4.6 | aprx. 2 |

In Table II, the symbols have the following meanings: A is heart survival rate, or function (rhythm on EKG), (# viable/# attempted); B is transplant index, or appearance, based on turgor, color, and contractility, ranging from 0–5 (worst to best); hr is time in hours; aprx. is approximately; CU is Columbia University solution with a db cAMP concentration value of 4 mM; XX is a solution containing components of the Columbia University solution, but replacing the db cAMP with Na Butyrate (4 mM); YY is a solution containing components of the Columbia University solution, but replacing the db cAMP with 8-Bromoadenosine 3',5' cyclic monophosphate (4 mM); ZZ is a solution containing components of the Columbia University solution, but replacing the db cAMP with 8-Bromoadenosine (4 mM).

TABLE III

Effect of Concentration of db cAMP in Ringer's Lactate Solution and University of Wisconsin Solution

| Time  | RL (A)    | RL + 0.1 mM db cAMP (A) | RL + 1.0 mM db cAMP (A) | RL + 4.0 mM db cAMP (A) |
|-------|-----------|-------------------------|-------------------------|-------------------------|
| 12 hr | 0/9       | 0/3                     | 3/3                     | 9/9                     |

| Time  | RL (B)    | RL + 0.1 mM db cAMP (B) | RL + 1.0 mM db cAMP (B) | RL + 4.0 mM db cAMP (B) |
|-------|-----------|-------------------------|-------------------------|-------------------------|
| 12 hr | aprx. 0.8 | aprx. 0.7               | 5                       | 5                       |

| Time  | UW (A)    | UW + 0.1 mM db cAMP (A) | UW + 1.0 mM db cAMP (A) | UW + 4.0 mM db cAMP (A) |
|-------|-----------|-------------------------|-------------------------|-------------------------|
| 12 hr | aprx. 33% | aprx. 33%               | 100%                    | 100%                    |

| Time  | UW (B)    | UW + 0.1 mM db cAMP (B) | UW + 1.0 mM db cAMP (B) | UW + 4.0 mM db cAMP (B) |
|-------|-----------|-------------------------|-------------------------|-------------------------|
| 12 hr | aprx. 1.8 | aprx. 3.4               | aprx. 5                 | aprx. 4.7               |

In Table III, the symbols have the following meanings: A is heart survival rate, or function (rhythm on EKG), (# viable/# attempted); B is transplant index, or appearance, based on turgor, color, and contractility, ranging from 0–5 (worst to best); hr is time in hours; aprx. is approximately; RL is Ringer's Lactate solution; UW is University of Wisconsin solution; RL+db cAMP is Ringer's Lactate solution to which db cAMP is added, with the concentration values of the added db cAMP indicated, in (mM); UW+db cAMP is University of Wisconsin solution to which db cAMP is added, with the concentration values of the added db cAMP indicated in (mM).

DISCUSSION

The data in this heterotopic rat model demonstrate the benefit of the organ preservation or maintenance solution of the subject invention in cardiac preservation, and show that the subject invention is superior to Ringer's Lactate solution and the University of Wisconsin solution. The data in this heterotopic rat model also demonstrate the benefit of db cAMP when this chemical is added to the Ringer's Lactate and the University of Wisconsin solutions, thereby demonstrating that db cAMP is an important, as well as a distinguishing, component of the organ preservation or maintenance solution of the subject invention. However, the data also show that the other ingredients of the subject invention contribute to its effectiveness, since the subject invention is shown to be more effective at preservation times that are substantially longer than the other solutions, whether or not the other solutions contain db cAMP.

In particular, Data in Table I A demonstrate that the organ preservation time of the Ringer's Lactate solution can be extended by adding db cAMP. Data in Table I A show that at four hours of preservation, all grafted hearts remain viable, and both the survival of the graft at ten minutes as well as the transplant index remain high. At eight hours, however, data in Table I A show that only those hearts which were preserved in the Ringer's Lactate solution containing db cAMP have a significant rate of survival, and have high transplant index scores. By twelve hours, data in Table I A show that all of the hearts preserved with the Ringer's Lactate solution are dead and have low transplant index scores; but the hearts preserved in the Ringer's Lactate solution containing db cAMP remain viable.

Data in Table I B likewise demonstrate the beneficial effect of db cAMP in prolonging organ preservation. Data in Table I B demonstrate that organ preservation time of the University of Wisconsin solution can be extended by adding db cAMP. The University of Wisconsin solution is currently thought of as the best preservation solution. Note that experiments involving the UW solution in Table I B use longer preservation times than for those experiments involving the Ringer's Lactate solution in Table I A, because UW solution is a better preservation solution than the Ringer's Lactate solution. Here again, db cAMP enhances cardiac preservation, though by 28 hours, graft survival using the University of Wisconsin solution is decreased, even with db cAMP present in the solution. While the effectiveness of the Columbia University solution is decreased at a preservation time of 36 hours, the Columbia University solution can still be effective.

Data in Table I C demonstrates the effectiveness of the organ preservation or maintenance solution of the subject invention (Columbia University solution) at the longer times of 24, 28, and 36 hours.

Data in Table I D demonstrates the effectiveness of the organ preservation or maintenance solution of the subject invention (Columbia University solution) by comparing it to other test solutions at preservation times of 28 and 36 hours. As mentioned above, the University of Wisconsin solution is currently regarded as the best preservation solution. However, Table I D directly demonstrates that the subject invention is not only superior to the University of Wisconsin solution, but superior even to the University of Wisconsin solution to which db cAMP is added. In other words, it is not the mere presence of db cAMP in the Columbia University solution that explains the superiority of the Columbia University solution over the other organ preservation solutions; the other components of the Columbia University solution also play a role in prolonging organ preservation. Although the relative importance of each component of the Columbia University solution remains to be determined, it can clearly be seen that the organ preservation or maintenance solution of the subject invention is superior to any known preservation solution with respect to prolonged storage of hearts.

Data in Table II show results of transplant experiments using other agents in place of the db cAMP. Db cAMP was chosen because it is an analogue of cAMP which is permeable to the cell membrane. As mentioned above, cyclic AMP (cAMP) is less permeable to the cell membrane than the analogues of cAMP, of which db cAMP is one. The experiment yielding the data in Table II was performed to show that the cyclic AMP portion of the molecule was responsible for its beneficial effects in this transplant model. Data in Table II show results of transplant experiments using another cAMP analogue, 8-bromoadenosine 3-5 cyclic monophosphate, for which similar beneficial results are obtained. However, addition of butyrate alone or bromoadenosine alone had no such beneficial effect. Data in Table II therefore demonstrate that it is the cAMP portion of the db cAMP molecule which is responsible for the beneficial effects with respect to cardiac preservation. Therefore, other suitable analogues of cAMP may be used in the subject invention.

Data in Table III demonstrates the effect of the concentration of db cAMP in Ringer's Lactate and University of Wisconsin solutions. Table III shows that the optimal concentration of db cAMP is at least 2 mM. Not shown are data from additional in vitro experiments which show that concentrations of db cAMP exceeding 4 mM are toxic to endothelial cells. Thus it is not fair to assume that if a little db cAMP is good, a lot is better. These considerations led to the choice of 2 mM db cAMP as the optimal concentration to be added to the Columbia University solution.

Experiment One therefore demonstrates that preservation of hearts in a heterotopic rat heart transplant model is improved when db cAMP is added to a simple electrolyte solution (Ringer's Lactate) or to a standard preservation solution (UW solution). Preservation is enhanced still further when the Columbia University organ preservation or maintenance solution is used.

Experiment Two:

A preliminary experiment employing materials and methods of Experiment One was performed to evaluate the relative importance of vasodilators.

In this experiment a base solution has the following composition: 67.4 mM D-glucose; 5 mM magnesium sulfate; 25 mM monopotassium phosphate; 95 mM potassium gluconate; and 50 g/l Dextran (molecular weight 308,000 daltons).

The relative importance of nitroglycerin, dibutyryl adenosine 3',5'-cyclic monophosphate (db cAMP), and of adenosine were tested by adding these components individually to the above base solution. Hence, one test solution had 5 mM added to the base solution; the second test solution had 0.1 g/l nitroglycerin added to the base solution; and the third test solution had 2 mM added to the base solution.

RESULTS AND CONCLUSIONS

This is only a preliminary experiment, and the results are recent. However, this experiment has shown that db cAMP and nitroglycerin are important; but that the organ preservation or maintenance solution will function without the presence of adenosine, so long as either db cAMP or nitroglycerin is present. A preferred embodiment, however, contains adenosine.

Further recent experiments suggest that the organ preservation and maintenance solution may function without the presence of db cAMP, so long as the solution contains nitroglycerin. It is believed, however, that the solution may function more effectively with the presence of db cAMP in addition to the nitroglycerin. In particular, in an experiment involving rat hearts which were preserved for twenty four hours, three of three hearts survived in a base solution containing nitroglycerin but not containing db cAMP or adenosine. Hence, the presence of nitroglycerin may be equally important, or perhaps more important, than db cAMP; and the presence of either db cAMP or nitroglycerin is more important than adenosine. It is believed that perhaps nitroglycerin may somehow enter the cell and somehow initiate or influence the making of cAMP by the cells, though the mechanistic or physiological role of nitroglycerin is open to further study.

While it is difficult to measure the relative importance of each individual ingredient in the organ preservation and maintenance solution of the present invention, the presence of vasodilators are very important.

Experiment Three:

In Experiment Three, an orthotopic primate heart transplant model is used to demonstrate the effectiveness of the organ preservation or maintenance solution of the subject invention (Columbia University solution).

A (7.4 kg male) baboon was prepared and treated in identical fashion to that done during a human cardiac transplantation, but rather than keeping the heart in an ice bucket for the maximum five (5) hours as is done in human heart transplant procedures, the baboon heart was preserved in the Columbia University solution for about twenty-four (24) hours.

Following a sterile preparation of the chest, the sternum is draped and a median sternotomy performed. The IVC, SVC, and aorta are encircled prior to placing a 16 gauge angiocatheter into the ascending aorta. The SVC is doubly ligated above the sinoatrial node and divided. As the aortic cross-clamp is applied, the IVC is clamped inferiorly and incised as is the left inferior pulmonary vein. These provide a vent for the cardioplegia solution (CU) (about 20 ml/kg) which is now infused at a pressure of about 200 mm Hg (although probably less pressure was seen at the aortic root because of the double length of tubing and the high viscosity of the solution). Following immersion in 700 mL of CU solution lat 0.5 degrees for 23 hours), the heart was again flushed with about 200 mL of freshly prepared CU solution (with the same pressure head) prior to implantation. The recipient baboon was a 9.4 kg female. This animal was also prepped and draped in a sterile fashion and through a median sternotomy, the heart was exposed. A cannulation site was selected in the ascending aorta through which an aortic cannula is inserted. Separate venous cannulae were placed in the SVC and IVC. Once full cardiopulmonary bypass was initiated, the lungs were fixed and the recipient's heart was excised. The donor heart was brought onto the field and anastomoses performed in the following order: left atrial, right atrial, pulmonary artery, and aorta. Air was vented from the heart using a cardioplegia needle and the pulmonary artery. The animal was removed from bypass without difficulty on dopamine, 0.5 mcg/kg/minute. Closure was with a single chest tube and heavy vicryl interrupted sutures. By two (2) hours post-operatively, the chest tube had been removed, the dopamine discontinued, and the animal was awake and moving in its cage. Total preservation time was 23 hours, 45 minutes.

The first baboon received a standard immunosuppressive regimen, including steroids, cyclosporine, and azathioprine. The animal survived and acted normally for four weeks following transplantation, at which time the animal was euthanized and sacrificed to examine the heart, as per experimental protocol.

RESULTS AND DISCUSSION

The recipient baboon survived the surgical heart transplantation procedure in which the heart was preserved for 23 hours, 45 minutes using the organ preservation or maintenance solution of the subject invention (Columbia University solution). This is the first time such extended preservation has ever succeeded in a primate. In contrast, results with UW solution in baboon heart transplant experiments showed that UW solution can not preserve hearts successfully for even eighteen (18) hours; at 18 hours the hearts appear to have decreased function. Attempts at preserving baboon hearts for longer than 18 hours using the University of Wisconsin solution have completely failed with only one of three (3) animals surviving the bypass period of the surgery; however, that animal had severe myocardial damage and died shortly after the operation. With the University of Wisconsin solution, these long term preserved hearts were noted to turn a dark maroon color and become rigid. At 24 hours of attempted preservation with UW solution, hearts showed no evidence of function, and were literally stone dead. We have recently completed our second baboon orthotopic transplantation, and were able to successfully preserve the heart for 24 hours and 15 minutes using the Columbia University solution. These results show that a heart could be preserved for about 24 hours using the Columbia University solution, and function normally following reimplantation. This result is not possible using the University of Wisconsin solution, which is currently considered the best organ preservation solution. This result has never before been achieved in a primate with a simple hypothermic storage of the explanted heart. In a second baboon experiment, a heart was preserved for 24 hours and 15 minutes. The animal was successfully weaned off bypass, that is, the artificial heart-lung machine that is standard for use in heart surgery. The transplanted heart was able to support the animal's circulation by itself, that is, without mechanical support. The animal lived for fourteen hours, and died of a heart attack. It is believed that the heart preservation procedure was successful, but that the animal died of medical complications that are difficult to manage in an animal intensive care unit.

Experiment Four:

Experiment Four is a preliminary and recent experiment involving a baboon lung transplant.

The composition of the organ preservation and maintenance solution is the same as that used for Experiments One and Three. In this experiment, the transplanted lung was preserved for twenty-two (22) hours. The surgery procedure is similar to that used in other lung transplant procedures. This experiment involved a single lung transplant.

RESULTS AND DISCUSSION

The results show that the organ preservation and maintenance solution of the subject invention was able to preserve the lung for twenty-two hours, following which the baboon had excellent blood oxygenation. The blood oxygenation following the lung transplantation on one hundred percent inspired oxygen was 570 mm Hg, reflecting excellent oxygenation.

This preservation time (twenty-two hours) is far longer than is clinically achievable to date. This result is also impressive because it is generally more difficult to preserve lungs than hearts. This experiment also demonstrates that the organ preservation and maintenance solution can successfully prolong preservation times of other organs besides hearts.

SECOND SERIES OF EXPERIMENTS: RESTORATION OF THE cAMP SECOND MESSENGER PATHWAY ENHANCES CARDIAC PRESERVATION FOR TRANSPLANTATION IN A HETEROTOPIC RAT MODEL

Abbreviations: EC=endothelial cell; SMC= smooth muscle cell; cAMP=adenosine 3'5'monophosphate, db-cAMP=$N^6$, $O^{2'}$-dibutyryl adenosine 3',5'monophosphate; 8-Br-cAMP=8-bromoadenosine 3'5'monophosphate, $S_p$cAMPS=$S_p$ isomer of adenosine 3'5'monophosphorothioate; $R_p$-cAMPS=$R_p$ isomer of adenosine 3'5'monophosphorothioate; PMN=polymorphonuclear leukocyte, LR=lactated Ringer's solution, UW=University of Wisconsin solution, PKA=cyclic AMP dependent protein kinase; mb-cAMP=$N^6$-monobutyryladenosine 3'5'monophosphate. cytokines (20–24).

SUMMARY:

Current organ preservation strategies subject graft vasculature to severe hypoxia ($pO_2$ about 20 Torr), potentially compromising vascular function and limiting successful transplantation. Previous work has shown that cAMP modulates endothelial cell (EC) antithrombogenicity, barrier function, and leukocyte/EC interactions, and that hypoxia suppresses EC cAMP levels. To explore the possible benefits of cAMP analogs/agonists in organ preservation, a rat heterotopic cardiac transplant model was employed; dibutyryl cAMP (db-cAMP) added to preservation solutions was associated with a time- and dose-dependent increase in the duration of cold storage associated with successful graft function. Preservation was also enhanced by 8-bromo-cAMP, $S_p$-cAMPS, and types III (indolidan) and IV (rolipram) phosphodiesterase inhibitors. Neither butyrate alone nor 8-bromoadenosine were effective, and the cAMP-dependent protein kinase antagonist $R_p$-cAMPS prevented preservation enhancement induced by 8-bromo-cAMP. Grafts stored with db-cAMP demonstrated a 5.5-fold increase in blood flow and a 3.2-fold decreased neutrophil infiltration after transplantation. To explore the role of cAMP in another cell type critical for vascular homeostasis, vascular smooth muscle cells were subjected to hypoxia, causing a time-dependent decline in cAMP levels. Although adenylate cyclase activity was unchanged, diminished oxygen tensions were associated with enhanced phosphodiesterase activity (59% and 30% increase in soluble types III and IV activity, respectively). These data suggest that hypoxia or graft ischemia disrupt vascular homeostasis, at least in part, by perturbing the cAMP second messenger pathway. Supplementation of this pathway provides a new approach for enhancing cardiac preservation, promoting myocardial function, and maintaining vascular homeostatic properties.

INTRODUCTION:

Preservation of hearts following explantation is a major limitation in clinical heart transplantation. Current approaches to cardiac preservation include attention to electrolyte balance, and the addition of impermeant anions, colloids, antioxidants, agents to limit entry of calcium, and metabolic substrates to promote the generation of high energy phosphate compounds on reperfusion (1–15). In view of the importance of vascular homeostatic properties such as permeability/barrier function, thrombogenicity/antithrombogenicity, expression of leukocyte-adherence molecules, and vasomotor tone, another important consideration in the design of cardiac preservation strategies is the maintenance of vascular integrity and function. These vascular homeostatic properties are modulated by the major cellular components of the vessel wall, including endothelial and smooth muscle cells. Although endothelial cells (ECs)* were once thought of as a passive, nonwettable conduit for blood flow, it has become clear that they play a dynamic role in the control of vascular properties (16–19). An important intracellular second messenger associated with EC regulation of vascular homeostatic properties is cAMP, which maintains EC function and prevents the induction of procoagulant activity in response to certain cytokines (20–24). When ECs are exposed to hypoxia, barrier function is diminished in parallel with a fall in levels of intracellular cAMP. This barrier function is almost completely normalized by the addition of cAMP analogs (25). Furthermore, ischemia-reperfusion induced increased microvascular permeability is prevented by agents which elevate cAMP in a perfused lung model (26).

In view of the ischemia/hypoxia which accompanies harvest and storage of an explanted heart, it was hypothesized that addition of cAMP analogs to preservation solutions would exert a beneficial effect on vascular function and organ preservation. The results of these studies indicate that agents which raise intracellular cAMP (such as rolipram or indolidan) or cAMP analogs/agonists (including $N^6,O^{2'}$-dibutyryl cAMP [db-cAMP], 8bromoadenosine3', 5'monophosphate [8-Br-cAMP], and $S_p$-cAMPS) promote cardiac preservation in a rat heterotopic transplant model. cAMP analogs appear to exert their effects via a pathway that involves, at least in part, stimulation of cAMP-dependent protein kinase, which results in enhanced blood flow and decreased leukocyte infiltration of the graft. To further explore the role of the vasculature in cAMP-induced enhancement of graft preservation, vascular smooth muscle cells (SMCs) were subjected to hypoxia, to determine whether a similar decline in intracellular cAMP would occur in vascular SMCs exposed to hypoxia as has been reported for ECs (25). In this series of experiments, it is demonstrated that vascular SMCs exposed to hypoxia show a time-dependent decline in cAMP levels, associated with an increase in phosphodiesterase activity, notably types III and IV. These findings are important because SMCs, as the cellular end-regulators of blood flow, are critical to vascular homeostasis, and because cAMP is known to play an important role in the regulation of vasomotor tone (27). Taken together, these studies indicate that a new level of intervention, addition of cAMP analogs to preservation solutions for maintenance of vascular function, improves cardiac preservation after prolonged hypothermic storage.

MATERIALS AND METHODS:

Heterotopic Rat Cardiac Transplant Model (28) Preparation of Preservation Solution.

Preservation solutions included lactated Ringer's (LR) solution Baxter, Edison, N.J.), or LR supplemented with rolipram ZK 62 711, Schering AG, Berlin, Germany), indolidan LY195115, Lilly Research Laboratories, Indianapolis, Ind.), sodium butyrate, 8-bromoadenosine, 8-bromoadenosine 3',5'monophosphate (8-Br-cAMP; Sigma Chemical Co., St. Louis, Mo.), the $R_p$-isomer of adenosine 3',5'monophosphorothioate ($R_p$-cAMPS; Biolog, La Jolla, Calif.), the $S_p$ isomer of adenosine 3',5'monophosphorothioate ($S_p$-cAMPS; Biolog), and $N^6,O^{2'}$-dibutyryl adenosine 3',5'monophosphate sodium (db-cAMP; Aldrich, Milwaukee, Wis.). Components were combined within 4 hrs of donor cardiectomy, and preservation solutions were kept at 4° C. University of Wisconsin solution (UW)(2–4 was purchased from Dupont (Wilmington, Del.).

Donor Cardiectomy. Male Sprague-Dawley rats (350–450 grams, Camm Research, Wayne, N.J.) were anesthetized, heparinized (1000 units of heparin given intravenously), and the donor heart removed in the following manner; a midline incision was performed, followed by rapid cardioplegic arrest with 5 ml of cold (4° C.), high potassium solution (NACl, 0.9%, and KCl, 40 mEq/L). The heart was maintained at 4° C. throughout the harvest procedure by the application of a cold saline soaked gauze over its surface. The inferior and superior vena cavae were ligated, the nortic and pulmonary artery roots were transected, the pulmonary veins were ligated, and the entire heart was excised and immersed in the cold preservation solution. The aortic root was flushed with ≈15 ml of the cold preservation solution until the coronary arteries became visibly clear, and the heart remained in the cold storage solution for the indicated duration until the time of transplantation.

Heterotopic Transplant. The same breed/size of rat was used, and similarly anesthetized, but not given heparin. A midline abdominal incision was made, and the infrarenal aorta and vena cava were occluded with a side-biting vascular clamp and longitudinal incisions were made in each vessel. The donor heart was removed from the preservation solution and kept moist with saline-soaked gauze. The donor heart's ascending aorta was anastomosed to the recipient's abdominal aorta, and the donor's pulmonary artery was anastomosed to the recipient's inferior vena cava using 8-0 monofilament suture material. Blood flow was restored to the graft (by removal of the clamp) exactly one hour after removal from the cold preservation solution. Pulsation of the donor aortic stump was observed to assure patency of the anastomosis. Ten minutes after removal of the cross-clamp, an electrocardiogram was taken (Grass Polygraph, Quincy, Mass.) and the heart was judged by the same blinded investigators throughout based on the presence/absence of regular contractions and a transplant score (0–5, worst-best, respectively) employing the following criteria: contraction (poor= 0, average=1, vigorous= 2), tissue turgor (hard= 0, average= 1, soft= 2), and color (dusky=0, pink=1). Overall, a graft was considered to have survived if regular contractions were observed with confirmation of corresponding depolarizations by ECG, with a transplant score $\geq 2$. The heterotopic cardiac transplant experiments performed in these studies were done by a single surgeon after establishment of this model and acquisition of surgical expertise, with control and experimental groups interspersed throughout the study period to prevent a time-dependent bias pertaining to surgical skills.

Perfusion of Donor Graft. Ten minutes after restoration of blood flow, a suspension of latex microspheres (0.5 ml of 10 μm diameter microspheres at a final concentration in $10^6$/ml in phosphate-buffered saline containing Tween 80, 0.05%) (E-Z Trac, Los Angeles, Calif.) was injected over 30 seconds into the donor aortic root. After one minute, the heart was rapidly excised, rinsed free of intracavitary and surface blood, and the atria and great vessels were removed. The ventricles were cut into pieces, each piece weighed, and then digested by alkaline hydrolysis, centrifuged and washed according to the manufacturer's instructions. Beads in each piece were then counted in an Improved Neubauer hemocytometer VWR Scientific, Piscataway, N.J.). Results are expressed as number of spheres per (40X) field per gram of ventricle. A minimum of ten fields were counted and the mean ± SEM is reported.

Myeloperoxidase assay/histology. Ten minutes following restoration of blood flow, transplanted hearts were excised and the aortic root was flushed for 5 minutes (rate of 2 ml/minute controlled by roller pump) with normal saline (Baxter, Edison, N.J.), the atria and great vessels were removed, and intracavitary blood was evacuated. Remaining ventricular pieces were weighed, and homogenized in phosphate buffer (50 mM; pH 7.4, 5 ml/gm of tissue) containing hexadecyltrimethylammonium bromide (0.5%; HTAB, [Sigma]) and frozen at −80° C. The myeloperoxidase assay was performed, as described (29), by thawing the sample, centrifuging at 40,000 g for 10 minutes at 4° C., and decanting the supernatant, which was assayed for myeloperoxidase activity using standard chromogenic spectrophotometric technique: test sample (0.1 ml) was added to phosphate buffer (50 mM; pH 6.0) containing O-dianisidine dihydrochloride (Sigma), hydrogen peroxide (0.0005%), and change in absorbance at 460 nm was measured over 5 min (increase in OD was linear over this time interval). For histologic study, cardiac graft samples were fixed in an ascending series of aldehydes, embedded, sectioned, and stained with hematoxylin and eosin.

Vascular smooth muscle cell culture, assays for cAMP, phosphodiesterase, and adenylate cyclase. Primary vascular smooth muscle cell cultures were obtained from bovine adrenal vessels by collagenase digestion and a series of differential adhesion steps. Cultures were characterized morphologically (30) and by the presence of smooth muscle cell actin (31). Cells were grown in modified Eagle's Medium (Gibco, Gaithersburg, Md.) supplemented with 10% fetal calf serum (Gemini, Calabasas, Calif.) and antibiotics as described (30,32). Cultures used were from passages 4–8. When smooth muscle cells achieved confluence in 24-well plates, the medium was aspirated and fresh growth medium was added just prior to exposing cultures to normoxia (ambient air) or normobaric hypoxia in a specially designed hypoxia chamber (Coy Laboratory Products, Ann Arbor, Mich.). Use of this chamber has been described in detail previously (21,32), and the $pO_2$ of the medium was ≈15–20 torr, assessed using a Model ABL-2 dissolved gas analyzer (Radiometer, Copenhagen, Denmark). Cells were exposed to hypoxia or normoxia for the indicated times, aliquots of conditioned medium were harvested, cells were washed twice with phosphate-buffered saline, and a third time in the same buffer containing 3-isobutyl-1-methylxanthine (Sigma). Cultures were then lysed by the addition of ice-cold trichloroacetic acid (6%). The trichloroacetic acid-soluble supernatant was removed from the well, extracted five times with water-saturated ether, dried, and the pellet resuspended in sodium acetate buffer (pH 6.2). A radioimmunoassay was then performed for cAMP according to the manufacturer's instructions (New England Nuclear, Boston, Mass.), as has been reported previously (25). Protein content of smooth muscle cell cultures was determined by the method of Lowry (33) after solubilizing protein precipitated in trichloroacetic acid in the 24-well plates with sodium dodecyl sulfate (2%). The protein content of hypoxic smooth muscle cell cultures was within 10% of the value for their normoxic counterparts. Cell viability was determined throughout the exposure to hypoxia by trypan blue exclusion, morphologic criteria, and release of lactate dehydrogenase into the cultured medium (the latter using a kit obtained from Sigma).

Adenylate cyclase activity was determined using SMCs grown to confluence in 10 cm² culture dishes exposed to either normoxia (standard cell incubator under ambient conditions) or hypoxia for 12 hours at 37° C. Cells were washed three times with ice cold 0.9% saline, and scraped into 30 ml of buffer containing 0.25 M sucrose, 50 mM tris (hydroxymethyl)aminomethane (Tris):HCl (50 mM, pH, 7.4), 5 mM $MgCl_2$, 5 mMEDTA, 2 mM dithiothreitol (DTT) and 100 μM phenylmethylsulfonyl fluoride (PMSF). Cell suspensions were homogenized using a Polytron homogenizer at half maximal speed for 30 seconds, and used immediately in an adenylate cyclase assay as previously described (34). Briefly, 25 μl aliquots of the homogenate were added to 40 μl of a reaction mixture containing 50 mM tris-HCl (pH 7.4), 2.5 mM $Mg^{2+}$, 0.143 mM ATP, an ATP regenerating system (creatine phosphate/creatine phosphokinase), ATP ([α-$^{32}$P]ATP, 1–2×10$^6$ cpm/assay tube [New England Nuclear]), and 6 mM theophylline [Sigma], incubated in a shaking water bath at 37° C. for 15 minutes. The adenylate cyclase reaction was terminated by the addition of an ATP-cAMP "stopping solution" as described (35). Isolation of [$^{32}$P]cAMP was accomplished by sequential Dowex and alumina chromatography with [$^3$H]cAMP as a recovery marker (36). Protein was determined as described above, and activity was expressed as pmol cAMP/15 min/mg protein.

Phosphodiesterase activity was measured by preparing cell homogenates as described for adenylate cyclase, centrifuging at 40,000×g for 20 minutes, and then analyzing the supernatant for phosphodiesterase activity using the two step method as previously described (37). Subtypes of phosphodiesterase were calculated as the difference between total and inhibited phosphodiesterase activities using specific inhibitors (37). Initial studies (not shown) confirmed that the reaction conditions employed were linear within the time period of the assay.

Statistics. Graft survival data and transplant scores were analyzed using the Kruskal-Wallis non-parametric analysis of variance (38). Comparisons of individual treatments were performed using the procedure described by Dunn (39). In addition, the effect of db-cAMP on the time-course of graft failure was quantified by multivariate logistic regression. Graft myeloperoxidase data, microsphere data, and cAMP/adenylate cyclase/phosphodiesterase data from experiments with cultured vascular smooth muscle cells were analyzed by t-tests when 2 treatments were performed or by analysis of variance when 3 or more treatments were performed. In the latter case, post-hoc comparison of treatment groups were tested using Tukey's procedure. Values are expressed as means ± SEM, with a $p < 0.05$ considered statistically significant.

RESULTS:

Enhanced cardiac preservation in the presence of cAMP analogs/agonists in a heterotopic rat transplant model.

Hearts preserved in Lactated Ringer's solution (LR) alone showed a decline in graft survival and scores that were dependent on the preservation time, with two thirds of grafts non-functional when preserved longer than 4 hrs, and 93% failing when preservation duration was 12 hrs (FIG. 1A). Addition of the cyclic AMP analog db-cAMP to LR solution prolonged graft survival and improved graft scores, resulting in 90% survival at 12 hours compared with 7% survival with LR alone. The beneficial effect of db-cAMP was dose-dependent, with optimal preservation occurring at 1–2 mM (FIG. 1B) (heart transplant survival closely paralleled transplant score in these and subsequent experiments, so that only the graft survival is shown in subsequent figures).

Figure 2A:
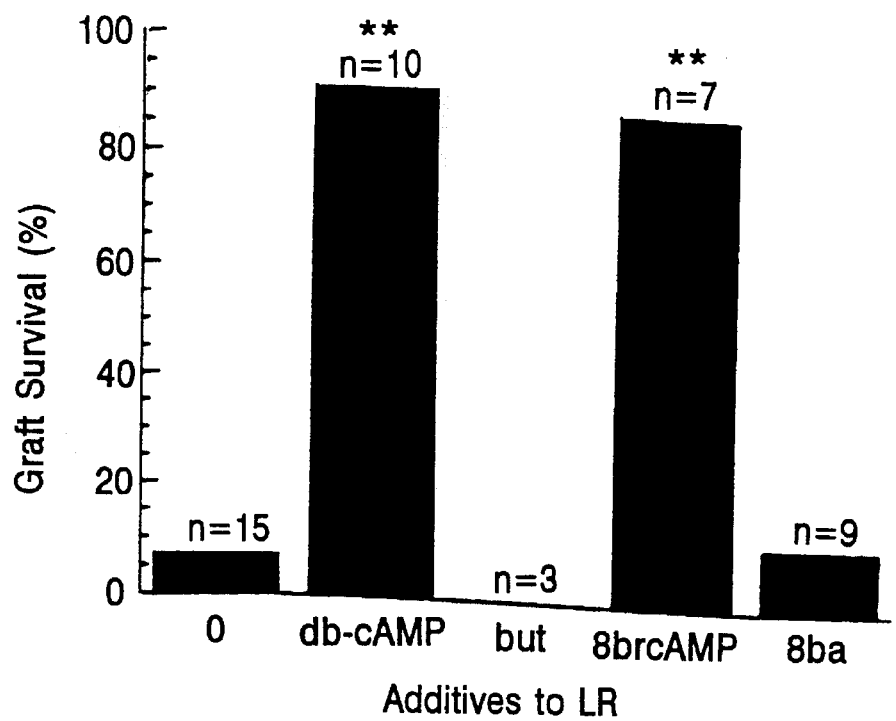
FIGS. 2A–D. Augmentation of the cAMP second messenger pathway enhances cardiac preservation. (A) Use of cAMP analogs and related controls. Rat hearts were explanted and preserved (as above) for 12 hours using solutions containing LR supplemented with either cAMP analogs, db-cAMP (4 mM) or 8-Br-cAMP (8 brcAMP, 4 mM), sodium butyrate (but, 4 mM), or 8-bromoadenosine (8ba, 4 mM). The percentage of surviving grafts after reimplantation is shown. (B) 8-Br-cAMP dose response experiment at 12 hours preservation demonstrates maximal benefit is achieved at a concentration of 0.1 mM. (C) Effect of phosphodiesterase inhibitors on cardiac preservation. Hearts were explanted and preserved for 12 hours as described above. Preservation solutions include LR alone, and LR supplemented with indolidan (ind; 10 µM) or rolipram (rol; 10 µM). (D) The effects of cAMP-dependent protein kinase agonists and inhibitors on cardiac preservation. Hearts were explanted and preserved for 12 hours as above in either LR, LR+8-Br-cAMP 11 mM), or LR+8-Br-cAMP (0.1 mM) + the cAMP-dependent protein kinase inhibitor $R_p$-cAMPS (0.5 mM). In other experiments, the cyclic AMP-dependent protein kinase agonist $S_p$-cAMPS (0.5 mM) was added to LR. Bars represent the percentage of surviving grafts, and demonstrate the importance of the cAMP-dependent protein kinase with respect to preservation. [** denotes $p< 0.01$ compared with LR alone; preservation scores parallelled survival data in all instances and are not shown].
Figure 2B:
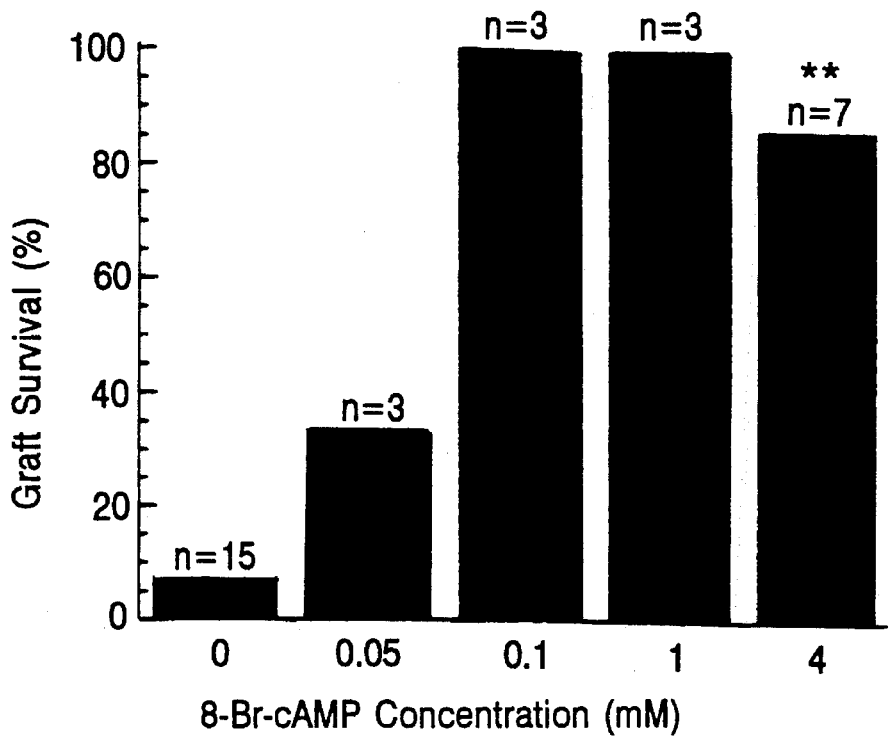
Figure 2C:
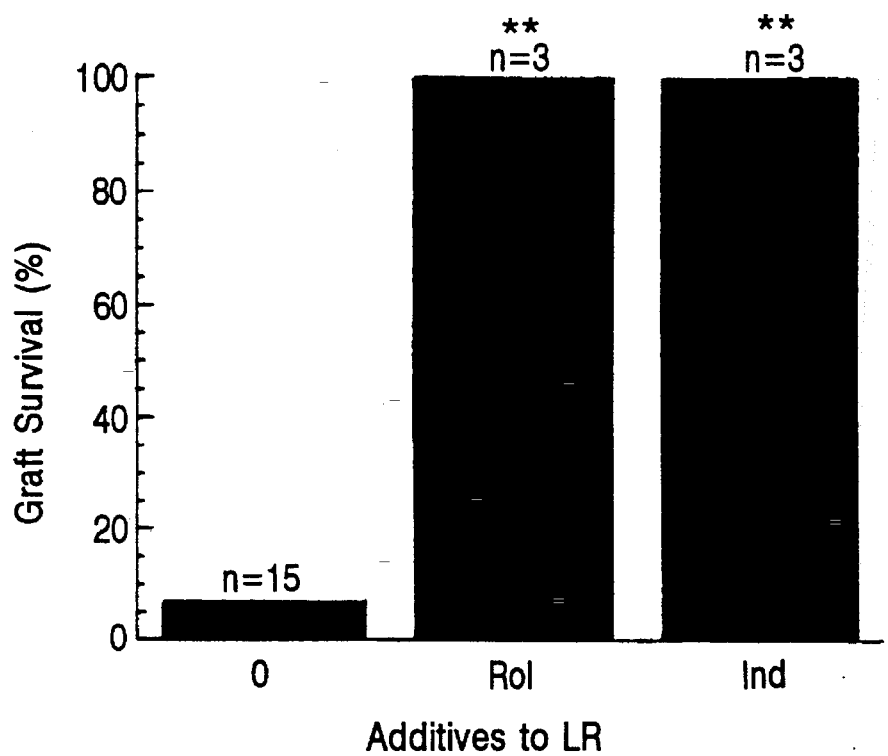

In order to establish that the cAMP was responsible for improving graft survival, and knowing that when db-cAMP enters the cell it is converted to N$^6$-monobutyryladenosine 3'5'monophosphate(mb-cAMP) and butyrate (40), the effect of sodium butyrate alone was assessed (FIG. 2A). Hearts preserved with butyrate in place of db-cAMP consistently failed after a 12 hr preservation period. Another cAMP analog, 8-Br-cAMP prolonged graft survival, whereas 8-bromoadenosine was ineffective. When 8-Br-cAMP was tested over a broad range of concentrations during a 12 hr preservation period, it was effective at concentrations ≈10-times lower than db-cAMP (FIG. 2B): 100% of grafts survived when preserved in LR solution containing 8-Br-cAMP at 0.1 mM. Further evidence in support of cyclic AMP's role in successfully prolonging the preservation period come from the results of experiments in which the phosphodiesterase inhibitors rolipram (10 μM) or indolidan (10 μM) (41) uniformly enhanced preservation of hearts stored for 12 hrs in LR solution (FIG. 2C). These data suggest that elevation of endogenous cAMP levels has a similar beneficial effect to exogenously administered cyclic AMP analogs.

Figure 2D:
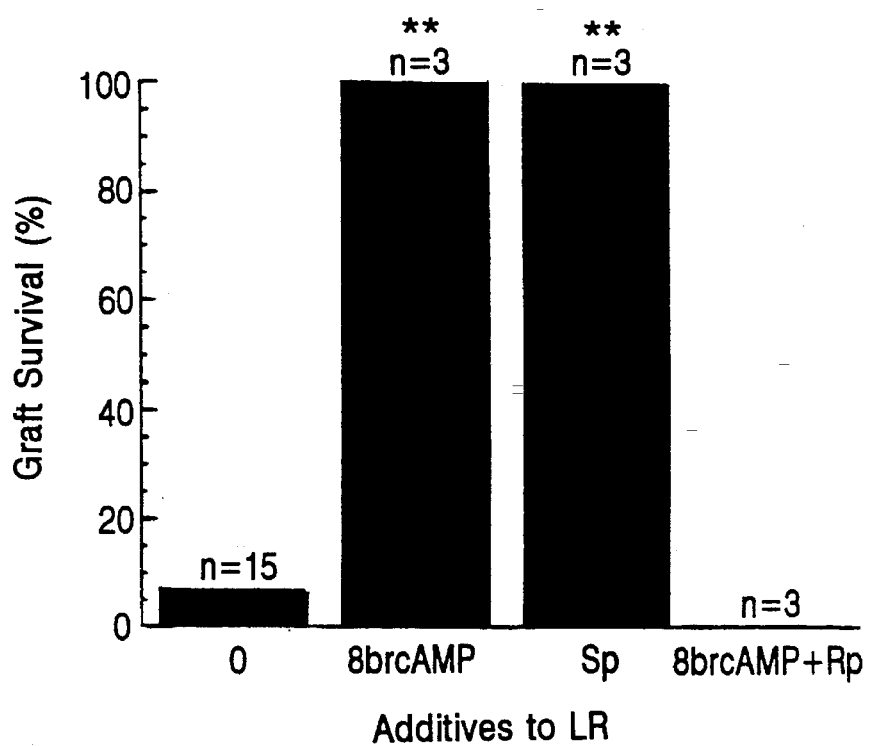

An important means through which cAMP exerts its effects intracellularly is via stimulation of the cAMP-dependent protein kinase (PKA). To explore the potential relevance of this mechanism to enhanced cardiac preservation, two stereoisomers of adenosine 3'5'monophosphorothioate were used (42). The $S_p$-isomer ($S_p$-cAMPS) is a PKA agonist that is not hydrolyzable by cellular enzymes, whereas the $R_p$-isomer ($R_p$-cAMPS) is a nonhydrolyzable competitive PKA antagonist, which binds to the PKA without causing activation. $S_p$-cAMPS enhanced preservation, whereas $R_p$-cAMPS abolished the salutory effect of 8-Br-cAMP on preservation, consistent with the important role of the PKA pathway in preservation enhancement (FIG. 2D). Although the cyclic GMP-dependent protein kinase may have a role in cardiac preservation, its direct activation by cyclic AMP analogs is unlikely since mb-cAMP and 8-Br-cAMP are respectively 313-fold and 53-fold less potent than cGMP in activating the cGMP-dependent protein kinase (43), and Sp-cAMPS is an antagonist of the cGMP-dependent protein kinase (44).

Figure 3A:
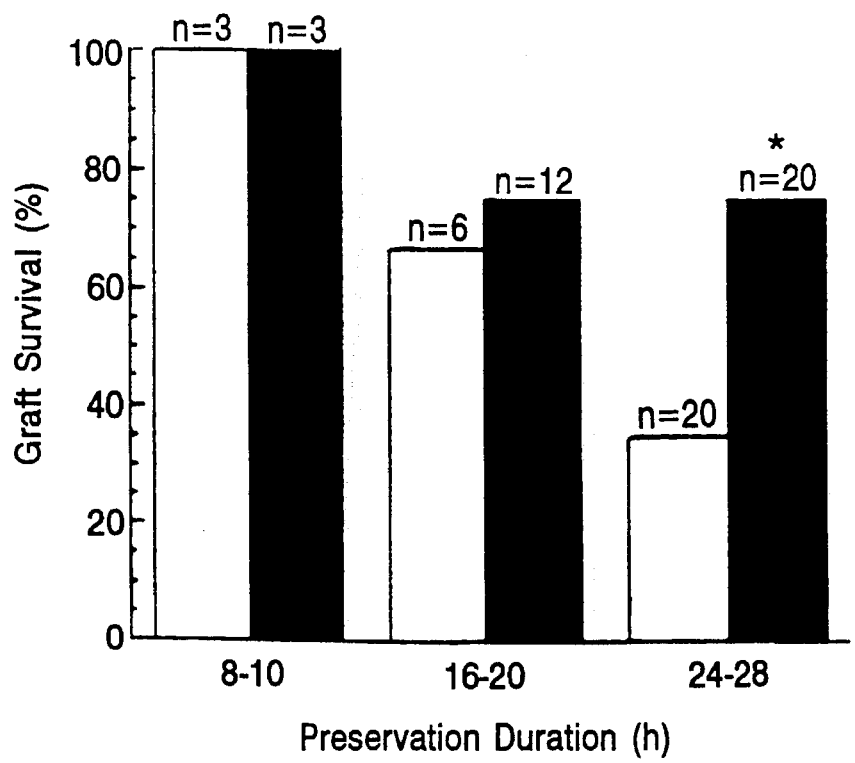
FIGS. 3A–B. Db-cAMP enhances cardiac preservation in UW solution. (A) Dependence on preservation time. Hearts were explanted and preserved (as described above) with UW (open bars) or UW+ db-cAMP (4 mM, closed bars) for the indicated times. The percentage of grafts surviving was evaluated 10 minutes following release of the aortic cross-clamp as described in the text. (B) Dependence on db-cAMP concentration. Hearts were explanted and preserved for 12 hours with UW supplemented with the indicated concentrations of db-cAMP. Graft survival is plotted versus the concentration of db-cAMP added to the preservation solution. [* denotes $p<0.05$, UW+db-cAMP vs UW alone].
Figure 3B:
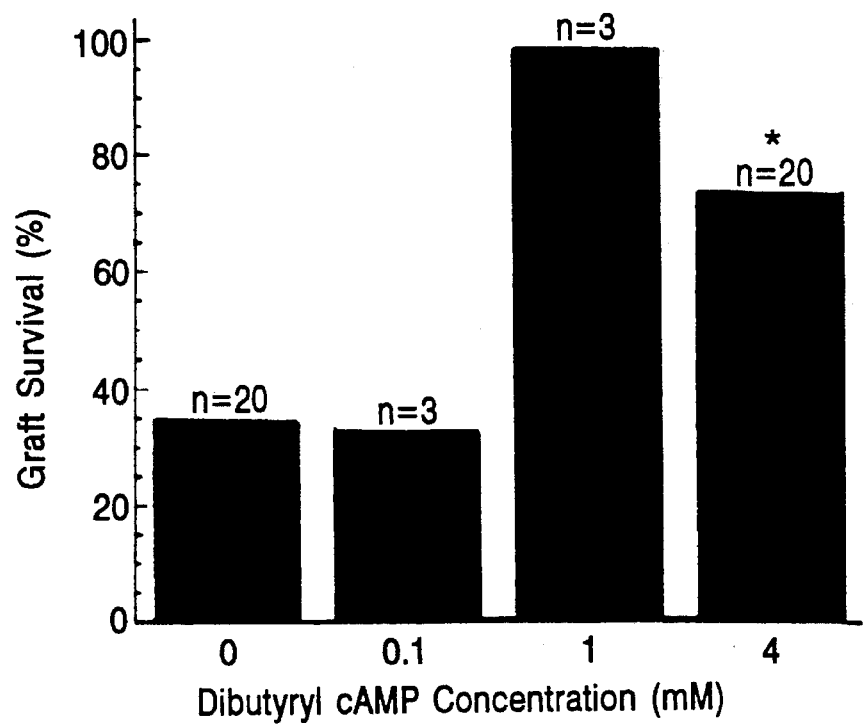

Because the simple balanced salt solution (LR) that was used for these initial experiments is not employed clinically for cardiac preservation, it was important to determine whether cAMP analogs enhanced preservation using the clinical standard, UW solution (4,45). Addition of db-cAMP to UW solution increased the time for effective preservation (FIG. 3A), with 75% of hearts surviving after 24 hrs of storage in UW+ db-cAMP versus only 35% in UW alone (p< 0.05). As with LR, the beneficial effects of db-cAMP on cardiac preservation in UW occurred in a dose-dependent fashion (FIG. 3B).

Effect of cAMP analogs added to cardiac preservation solution on graft perfusion and leukocyte infiltration.

Figure 4:
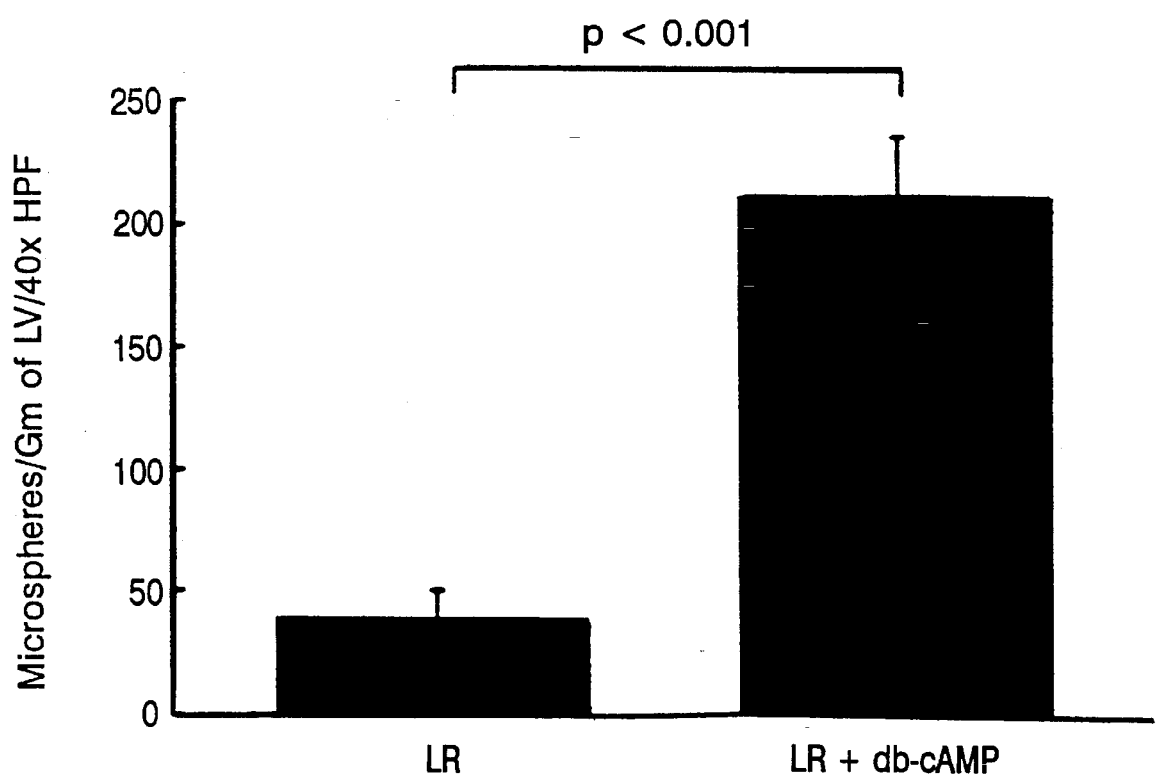
FIG. 4. Blood flow as measured by accumulation of colored latex microspheres in graft vasculature. Hearts were preserved for 12 hrs and transplanted; 10 minutes following the release of the aortic cross-clamp, a suspension of latex microspheres (0.5 ml, $10^6$/ml) was injected into the donor aortic root, and the heart was excised after one minute. Microspheres were recovered from ventricular tissue following alkaline hydrolysis, counted, and expressed as microspheres/gram/40X high power field (mean of 10 observations ± SEM is shown. Preservation solutions included LR alone (n=5) or LR+db-cAMP (2 mM, n=10). Addition of db-cAMP to the preservation solution is associated with increased graft blood flow.

Because the hypothesis that cAMP analogs enhanced cardiac preservation was borne out by the experiments described above, and knowing that elevated intracellular cAMP levels in vascular smooth muscle cells is associated with vasorelaxation (27), the effects of cAMP analogs on graft blood flow following transplantation were evaluated. Relative blood flow was assessed by the injection of colored latex microspheres into the aortic root of the transplanted heart, and quantitating deposition of microspheres (10 μm) in the vasculature (46). Histologic studies demonstrated increased numbers of beads trapped in the microvasculature of hearts which were successfully transplanted, indicative of increased perfusion, versus fewer beads in grafts which failed. When hearts preserved in LR alone were compared with those preserved with LR + db-cAMP (2 mM) at 12 hours, a significant increase in blood flow was observed in those hearts preserved with supplemental db-cAMP (FIG. 4).

Figure 5:
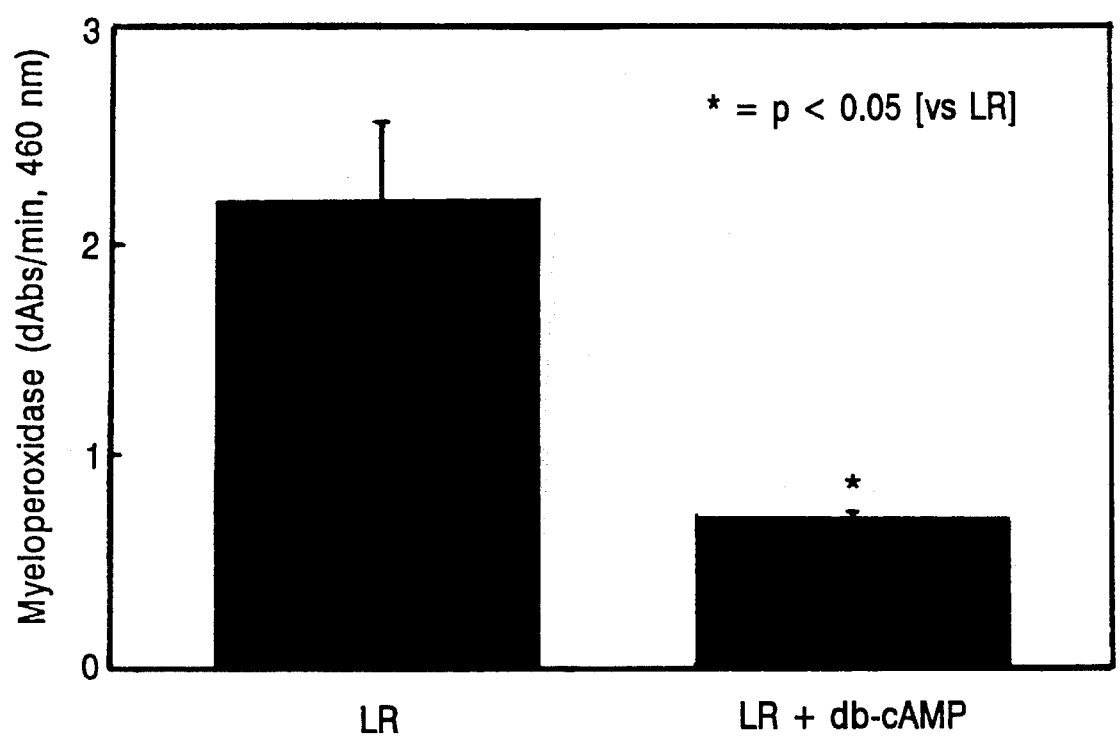
FIG. 5. Leukocytic infiltration following preservation/transplantation. Myeloperoxidase (MPO) activity was measured in tissue homogenates from cardiac grafts harvested 10 mins after the reestablishment of blood flow. Grafts preserved for 12 hrs in LR+ db-cAMP (2 mM, n=3) had lower levels of MPO activity compared with grafts stored in LR alone (n=6), which had 3.2-times more MPO activity per gram of protein.

Infiltration of the heart by polymorphonuclear leukocytes (PMNs) is an important cause of myocardial damage in the setting of ischemia/reperfusion (47–53). Consistent with this view, histologic examination of the vasculature from a heart preserved in LR which subsequently failed showed a ring of PMNs adherent to the vessel surface which was not seen in a successfully transplanted cardiac graft preserved in LR + db-cAMP. Leukostasis in the transplanted heart ten minutes after restoration of blood flow. Hearts preserved successfully for 12 hours with db-cAMP (2 mM) in LR show no PMNs in a blood vessel (V), whereas many adherent PMNs are seen forming a ring about the luminal surface of vessels from a failed graft preserved for 12 hours with LR alone. Sections were stained with hematoxylin and eosin. (not shown). This was quantified by measuring myeloperoxidase activity in grafts as an index of the presence of PMNs. Hearts preserved for 12 hours in LR+ db-cAMP (2 mM) showed a 3.2-fold decrease in myeloperoxidase activity compared with controls preserved for 12 hours in LR alone ($p<0.05$) (FIG. 5).

Effect of hypoxia on vascular smooth muscle cell cAMP.

The effect of db-cAMP to increase perfusion in the cardiac graft suggested the possibility that it was acting at the level of the vascular smooth muscle cell to induce vasorelaxation. One mechanism underlying this observation would be if harvest and storage of the heart resulted in hypoxia and an associated fall in smooth muscle cell cAMP, as occurs in hypoxic ECs (25), thereby preventing normal vasorelaxation in the graft. Supporting this hypothesis is the fact that the measured $pO_2$ of the storage solution remaining in the vasculature of a preserved heart for 18 hr was extremely hypoxic (19.9 torr). Exposure of cultured smooth muscle cells to hypoxia resulted in a fall in intracellular cAMP levels (closed bars, FIG. 6A). This occurred in a time-dependent manner when cultures were exposed to an atmosphere with $pO_2 \approx 15$–20 torr, with cAMP levels falling from $8.4\pm0.9$ pg/ml/mg cell protein during normoxia to $3.0\pm0.6$ pg/ml/mg cell protein following 12 hours of hypoxic conditions. This decline could not be attributed to extrusion of cAMP into the growth medium (open bars, FIG. 6A), or to cell death, as smooth muscle cells remained firmly attached to the growth surface (there was no increase in floating cells), there was no increase in trypan blue uptake, and lactate dehydrogenase levels in the medium were not elevated (data not shown).

Figure 6A:
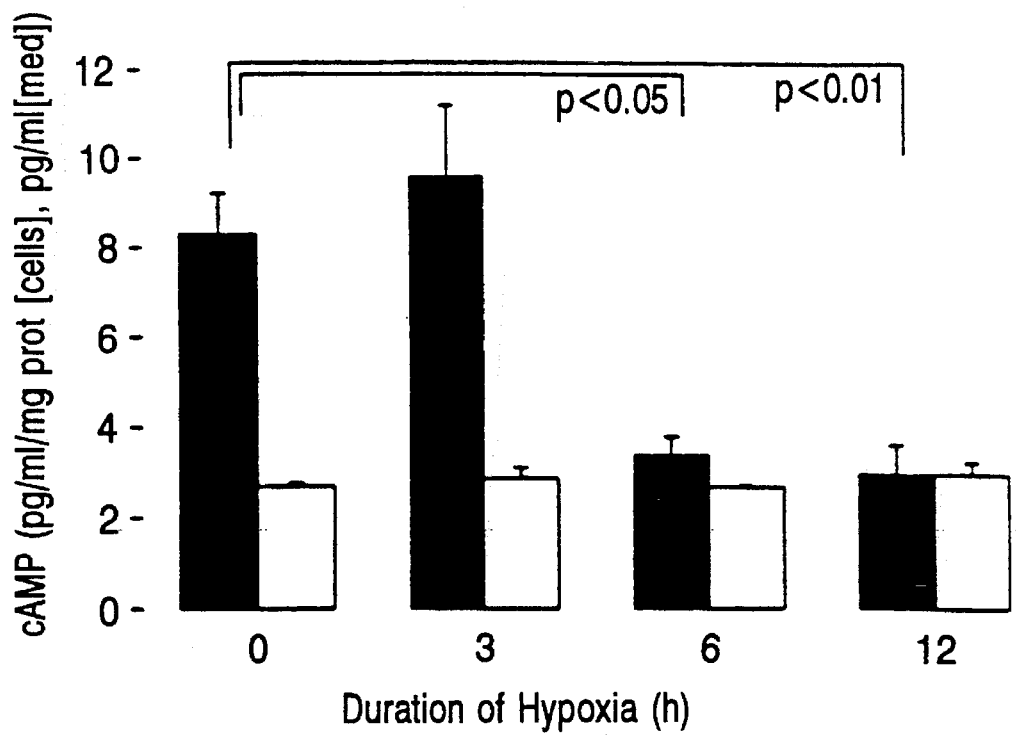
FIGS. 6A–C. Effects of hypoxia on cultured vascular smooth muscle cell cAMP levels, generation, and degradation. (A) Time-course of cAMP decline in vascular smooth muscle cells exposed to a hypoxic environment ($pO_2$ 15–20 Torr). Confluent smooth muscle cells were exposed to a hypoxic environment for the indicated durations, and cell lysates (closed bars) and conditioned medium (open bars) were analyzed for cAMP content by radioimmunoassay. cAMP levels decline in parallel to the duration of exposure to the hypoxic environment, without evidence of enhanced extrusion into the culture medium. (B) Adenylate cyclase activity of homogenates vascular smooth muscle cells exposed to 12 hours of hypoxia (closed bars) or normoxia (open bars) at baseline (Basal), or with added isoproterenol (10 µM; ISO); Gpp (NH)$_p$ (10 µM; GPP); the combination of isoproterenol and Gpp (NH) p (I+G); or forskolin (10 µM; FOS). Basal and stimulated adenyl cyclase activities are similar for both normoxic and hypoxic vascular SMCs. (C) Phosphodiesterase activity of homogenates of normoxic and hypoxic vascular smooth muscle cells. Total phosphodiesterase activity normalized to protein concentration) in the soluble cytosolic fraction) of vascular SMCs exposed to 12 hours of normoxia or hypoxia was determined in the absence of inhibitors of PDE, as well as in the presence of indolidan (1 µM; Type III PDE inhibitor) or rolipram (10 µM; Type IV PDE inhibitor). Types III and IV PDE activities were calculated as the difference between total and inhibited PDE activities, measured in the presence of indolidan or rolipram, respectively. The graph represents the means of three determinations each for normoxic and hypoxic samples, and demonstrates an increase in both types III and IV PDE activity in the hypoxic SMCs.
Figure 6B:
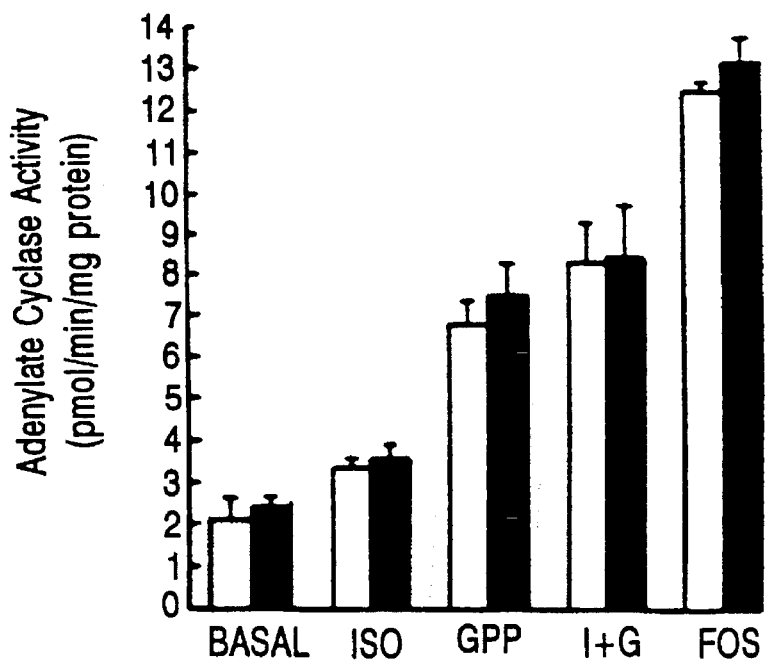
Figure 6C:
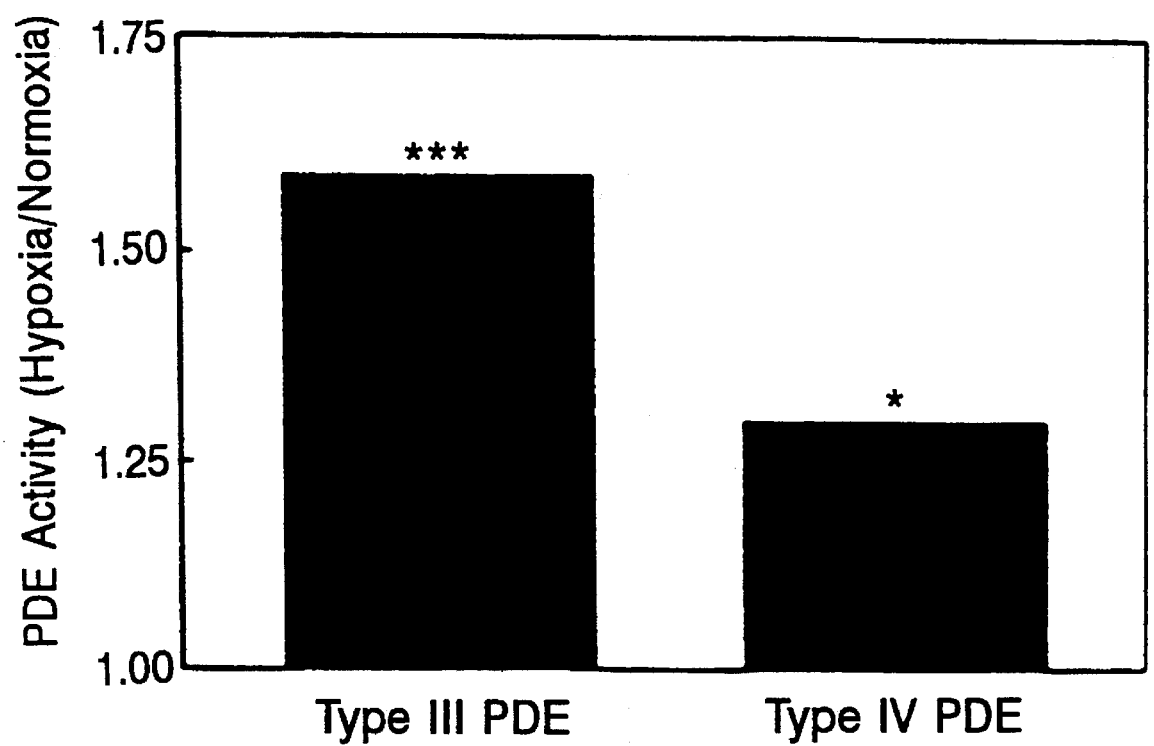
Figure 8A:
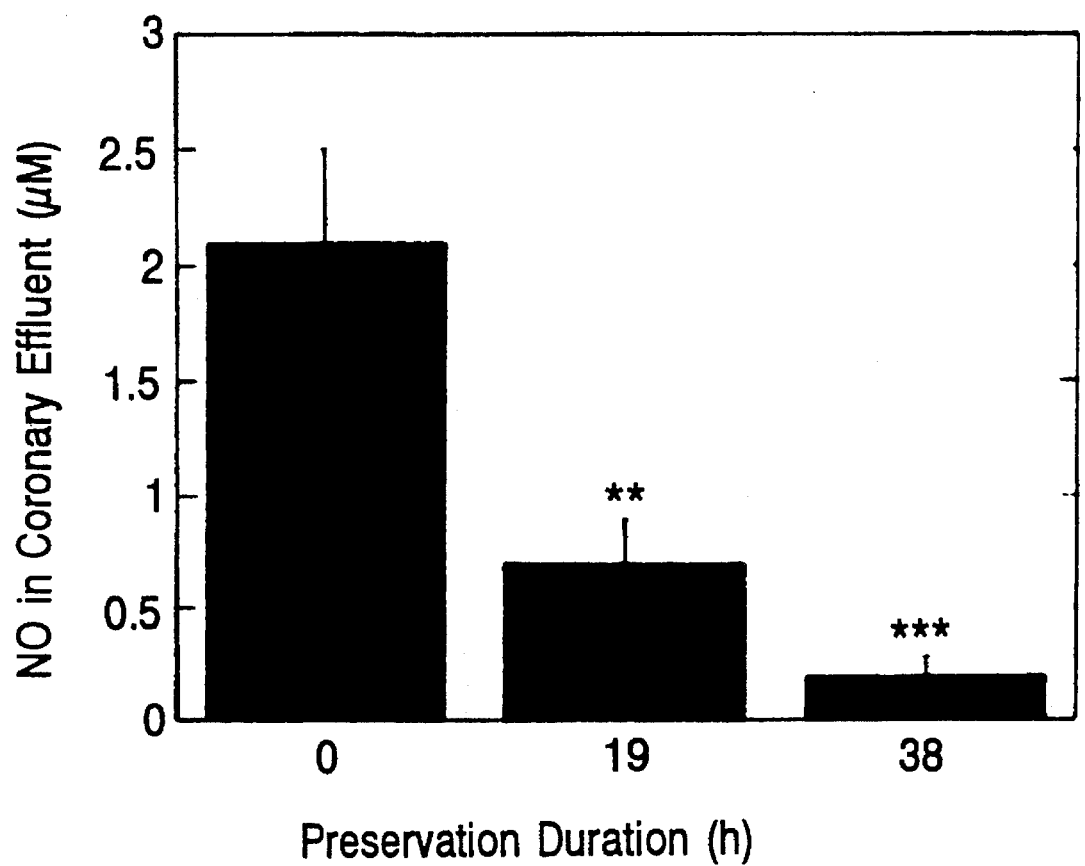
FIGS. 8A–C. Direct measurement of coronary vascular and endocardial nitric oxide synthesis by differential pulse voltammetry or amperometry[13]. (A) NO was measured by differential pulse voltammetry (sensor-working electrode, saturated calomel electrode (SCE) reference, and platinum wire-auxiliary electrode, pulse amplitude 40 mV) from aliquots of perfusate demonstrating the difference in production of NO by the coronary vasculature of freshly explanted (n=5) and preserved hearts (19 and 38 hours, n=4 for each) [ = $p<0.01$, * $p<0.001$ vs 0 hrs preservation]; (B) Representative differential pulse voltammograms from these experiments; (C) NO concentration measured in the flushing solution at different time intervals (fresh heart— open circles, preserved heart (38 hrs) - solid circles). Although NO is seen in the flush of a transplanted/reperfused heart, the levels are markedly diminished; Augmentation is seen following the addition of SOD, suggesting the role of oxygen free-radicals in the destruction of available NO.
Figure 8B:
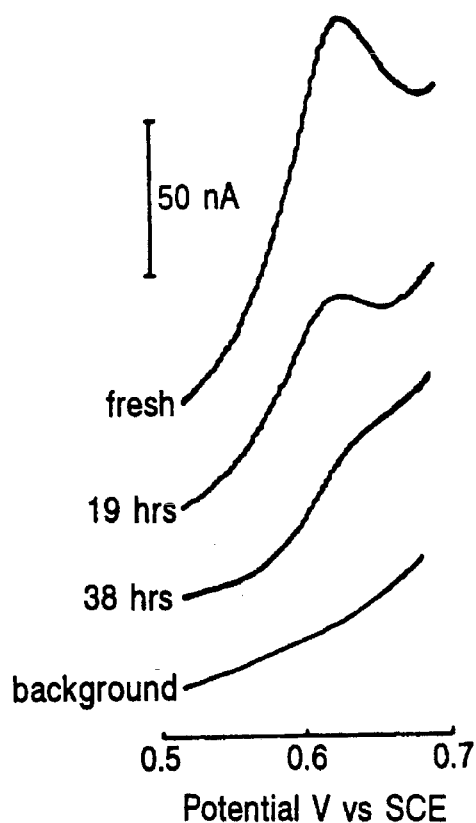
Figure 8C:
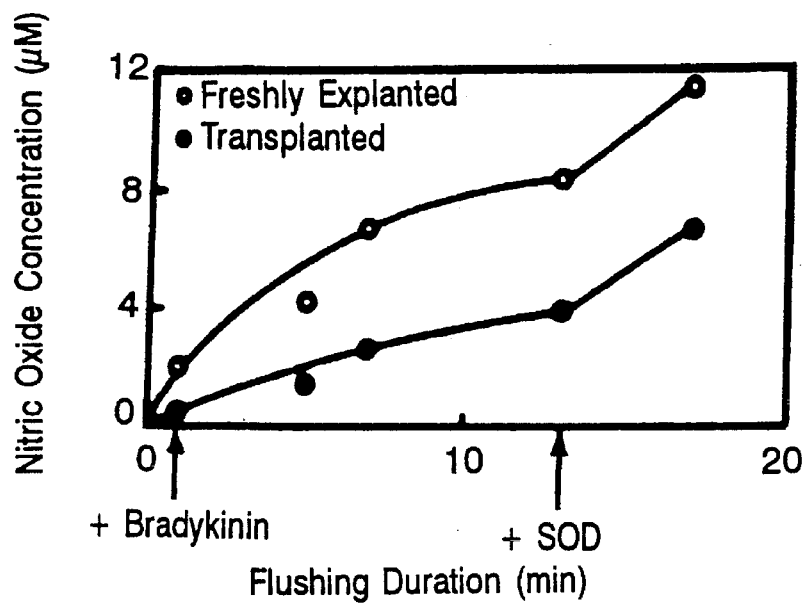
Figure 9A:
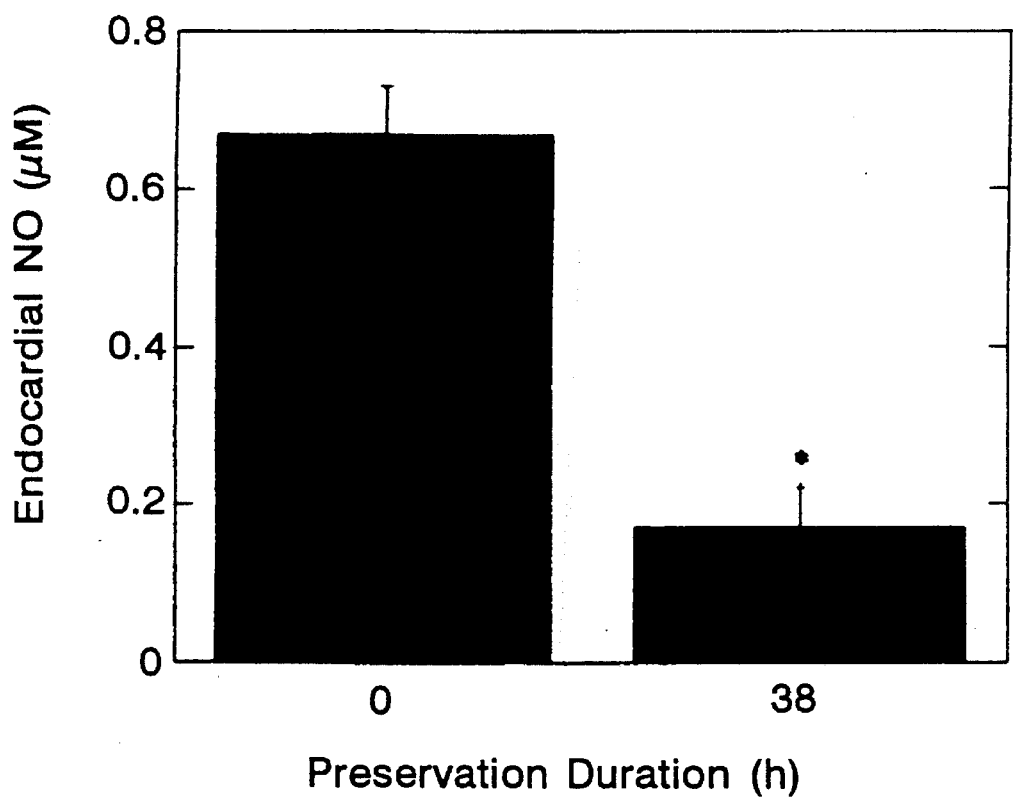
FIGS. 9A–B. Measurement of endocardial NO. (A) The porphyrinic sensor was implanted in the septal endocardium of freshly explanted (n=3) or preserved/transplanted hearts (n=3), and after baseline stabilization, $6\times10^{-6}$ M bradykinin was applied and NO release continuously monitored by amperometry at constant potential of 0.63 V. Peak NO levels are shown. [* =$p<0.05$ vs 0 hrs preservation]; (B) Representative amperometric tracing demonstrating NO levels following bradykinin challenge. Although the endocardium of a preserved/transplanted heart generates an analytic signal following bradykinin challenge, it is significantly less than that of a freshly explanted heart.
Figure 9B:
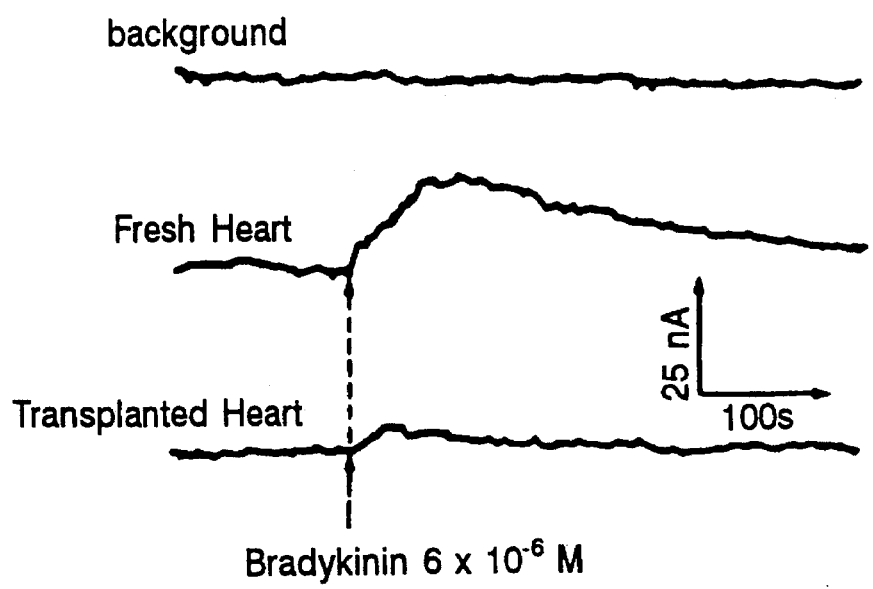
Figure 10:
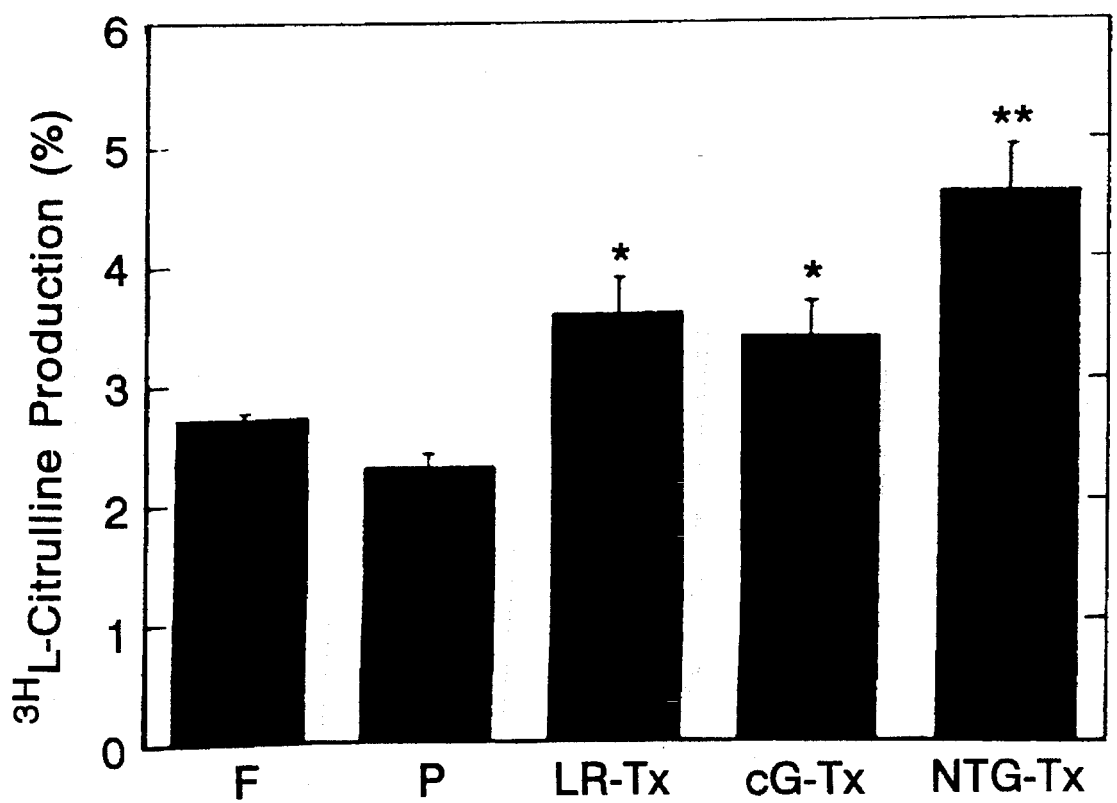
FIG. 10. Cardiac nitric oxide synthase (NOS) activity. NOS activity was measured in cardiac extracts by measuring the conversion of $^3H$-L-arginine to $^3H$-L-citrulline, as described in the text. Hearts were either freshly explanted (F; n=3), preserved for 12 hours in LR (P; n=3), or preserved for 12 hours in LR alone and transplanted (LR-Tx; n=3) or LR supplemented with 0.5 mM 8-Br-cGMP(cG-Tx; n=3) or 0.1 mg/ml nitroglycerin (NTG-Tx; n=3). [* = $p<0.05$, **= $p<0.01$ vs preserved but non-transplanted hearts].
Figure 11A:
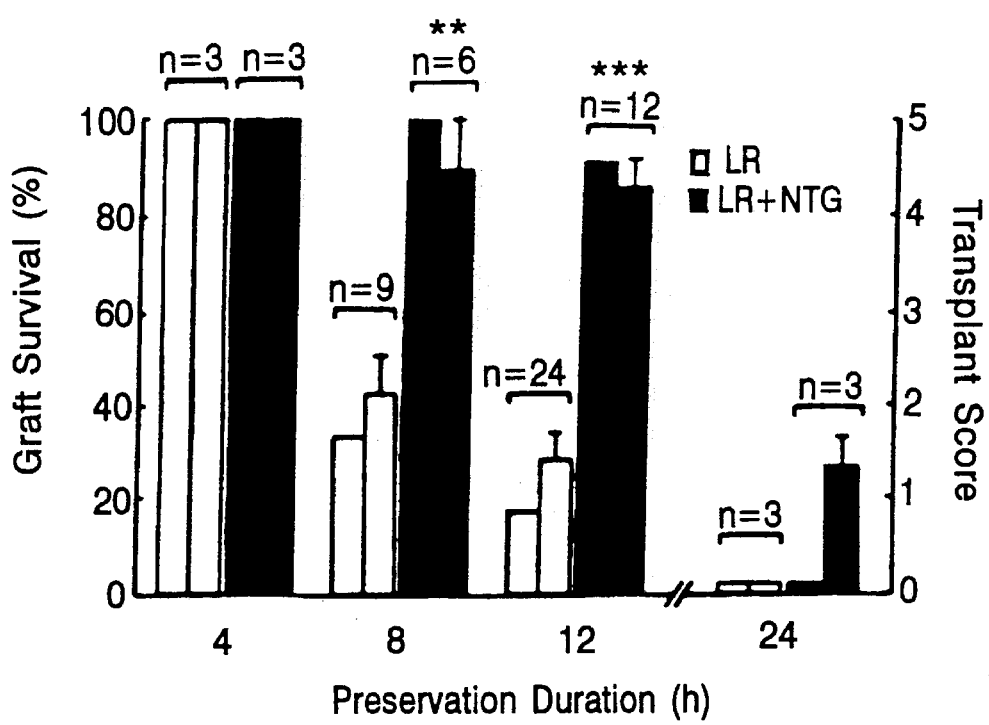
FIGS. 11A–D. The role of the nitric oxide pathway in cardiac preservation and transplantation. A heterotopic rat cardiac transplant model was used[8], with harvest, preservation, transplantation, and assessment performed as described in the methods section. (A) Time course of NTG effect. NTG (0.1 mg/ml, closed bars) added to LR enhanced survival (left-most bars at each condition/time point)) and scores (rightmost bars at each condition/time point) compared to LR alone (open bars). (B) NTG dose-response at 12 hrs preservation followed by transplantation. Maximal effect is seen at 0.1 mg/ml. (C) Role of the NO pathway in enhancing graft preservation. At 12 hours of preservation with LR, endothelium independent vasodilators (NTG 0.1 mg/ml, nitroprusside [SNP, 0.01 mg/ml], 8-Br-cGMP [cGMP, 0.5 mM]) and L-arginine (Arg, 2 mM) all enhanced preservation, whereas a five-fold molar excess of $N^G$-monomethyl-L-arginine [N] antagonized the beneficial action of 2 mM L-arginine. There was no survival of cardiac grafts preserved for 12 hrs with N alone. (D) Dose-response of 8-Br-cGMP at 12 hours preservation in LR demonstrated maximal benefit by 0.5 mM. Control experiments at 12 hours preservation were performed throughout the experimental period (n=24 transplants total), and are shown in panels A–D for illustrative purposes. (*= $p<0.05$, = $p<0.01$, and *= $p<0.001$, experimental group vs. LR alone at the identical preservation duration).
Figure 11B:
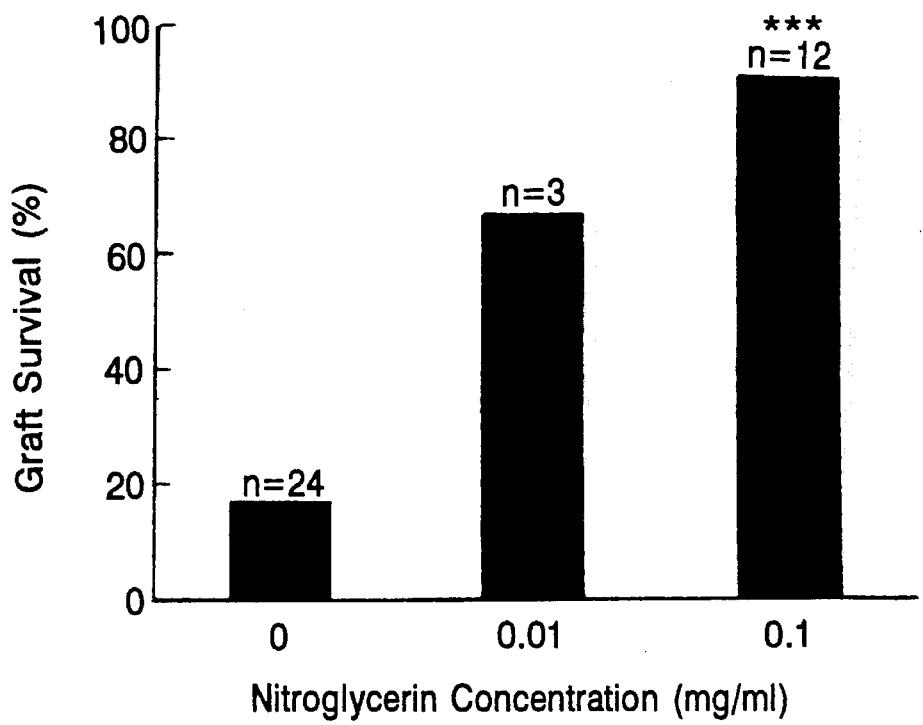
Figure 11C:
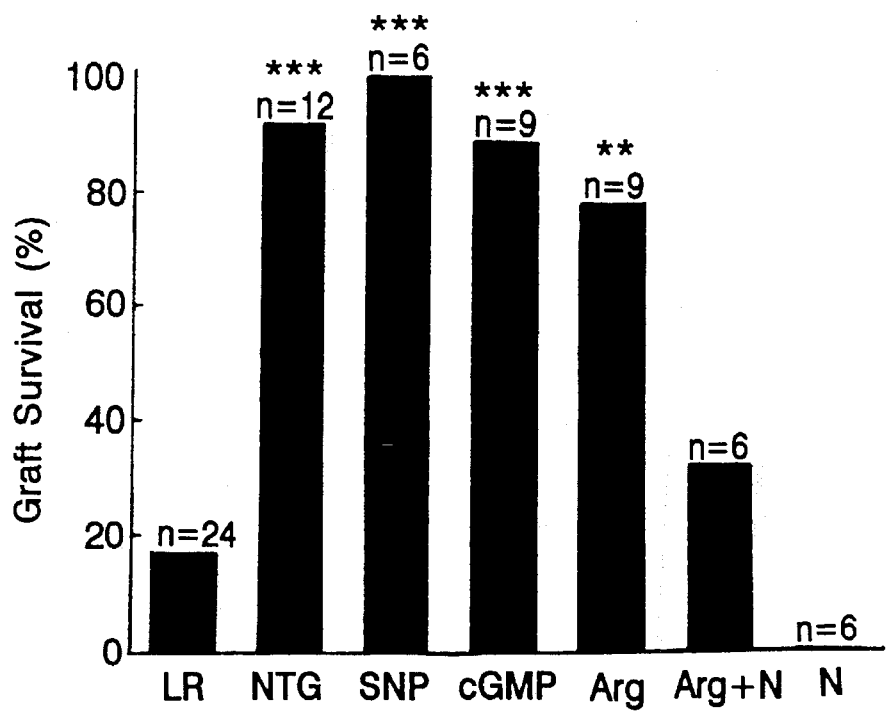
Figure 11D:
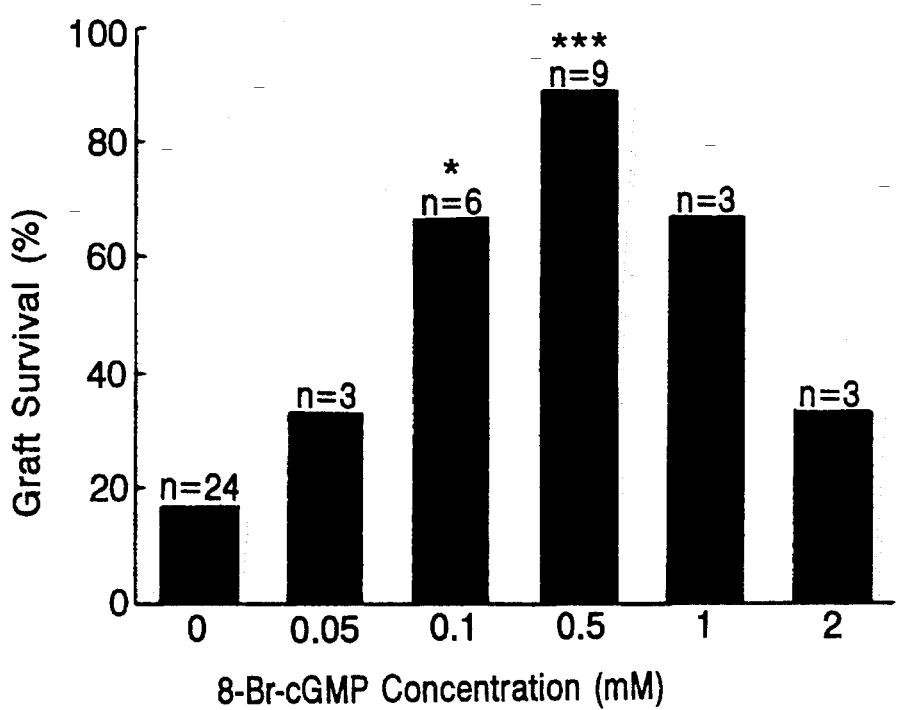

In order to determine whether decreased production or increased degradation of cAMP was responsible for the hypoxia-induced decline in intracellular cAMP in vascular smooth muscle cells, adenylate cyclase and phosphodiesterase (PDE) activities were measured. There was no measurable difference in baseline (or stimulated) adenylate cyclase activity between normoxic and hypoxic smooth muscle cells (FIG. 6B). In contrast, hypoxia augmented the metabolism of cAMP. Although total PDE activity was not significantly increased in hypoxia ($82\pm4.7$ nmol adenosine/min/mg protein vs $77.1\pm4.4$ for hypoxia vs normoxia, respectively), there were significant increases in both types III and IV PDE activity (59.2% and 30.0% increase, respectively, $p<0.001$ and $p<0.05$ for types III and IV PDE, respectively) (FIG. 6C). These results suggest that the decline in vascular smooth muscle cell cAMP is not due to a decreased production, but rather to an increased activity of the enzyme responsible for its degradation.

DISCUSSION:

These studies show that addition of agents which elevate intracellular cAMP to cardiac preservation solutions increases the maximal duration of cold ischemia associated with restoration of cardiac graft function after transplantation in a rat heterotopic cardiac transplant model. The cAMP analogs utilized in these studies appear to exert their effect(s) via stimulation of cyclic AMP-dependent protein kinase, presumably followed by recruitment of effector mechanisms, although the possible involvement of the cyclic GMP-dependent protein kinase cannot be ruled out. Furthermore, cAMP analogs enhanced preservation when added to UW solution, the clinically accepted standard for cardiac preservation (4,45). Second messenger cyclic nucleotides such as cAMP have diverse biologic effects, and it is likely that many cell types within the heart are effected by cAMP analogs in the preservation solution. In preliminary studies, it was determined that the resting membrane potential of individual myocytes is more negative when a heart has been preserved with a preservation solution containing db-cAMP and nitroglycerin, compared to a preservation solution without these agents (54). Although this effect on non-vascular cells within the heart may contribute to the beneficial effects of cAMP analogs on graft survival, the analysis of hearts in the current study focuses on markers of graft vascular function. These studies indicate that agents which stimulate the cAMP second messenger pathway maintain blood flow, diminish leukostasis, and preserve tissue turgor and color following reperfusion. These observations underscore the role of the cAMP pathway and the importance of maintaining vascular homeostasis within the graft for the success of organ transplantation.

The period of reperfusion is an especially vulnerable period for the graft with respect to maintenance of vascular function, because restoration of blood flow initiates the host response through the interaction of leukocytes, the coagulation and complement systems, with the hypoxic/reoxygenated endothelium. In these experiments, grafts were evaluated at 10 minutes of reperfusion for several reasons. First, pilot studies demonstrated that transplanted hearts started with a pale color immediately out of preservation solution, but turned pink after release of the aortic cross-clamp as blood could be visibly observed to distend the epicardial coronary arteries. Hearts which failed always followed this initial sequence, but 2–3 minutes after the start of reperfusion, would darken and become palpably turgid, and fail to contract. Failed grafts never regained function regardless of the observation duration, whereas surviving grafts continued to function for several hours of observation. A blinded analysis of graft function at 10 minutes was never altered by a subsequent evaluation of the same graft as late as 8 hours later. These results are consonant with experiments using coronary artery rings from feline hearts subjected to ischemia/reperfusion in vivo, which demonstrate impaired vasorelaxation within minutes of reperfusion (19). In addition, toxic oxidants formed within minutes of reoxygenation/reperfusion in endothelial cells (55,56) and hearts (57,58) may contribute to the pathogenesis of vascular dysfunction in the reperfused graft. Because these oxidants form early following reperfusion and can alter vascular permeability and lower cAMP levels (59), grafts were evaluated ! 0 minutes after the start of reperfusion.

Although morphologic evidence of parenchymal and vascular damage is subtle during the period of organ storage/hypoxia (data not shown), in contrast to the pathologic changes observed during reperfusion, the period of hypoxia is emerging as an important priming factor for subsequent vascular dysfunction. Hypoxic ECs display enhanced thrombogenicity (21, 60–62), leukocyte adhesivity (63,64), monolayer permeability (25), diminished nitric oxide production, and are primed for the production of oxygen free radicals (55,58). In this context of vascular homeostasis, the cAMP second messenger system has multiple roles. In ECs, decreased cAMP levels result in perturbation of cell shape and decreased barrier function of the monolayer (22, 24, 25), whereas increased levels of cAMP block induction of EC procoagulant activity (23), cause induction of the anticoagulant cofactor thrombomodulin (23), and block induction of transcription of certain leukocyte adherence molecules in response to the cytokine tumor necrosis factor (65). In vascular smooth muscle, increased cAMP levels are associated with vasorelaxation (27). In PMNs, elevated levels of cAMP are associated with decreased EC-leukocyte interactions (66) as well as diminished production of superoxide (67). Thus, addition of agents such as cAMP analogs to organ preservation solutions in order to preserve vascular homeostasis may prove to be important for prolonging preservation and minimizing post-transplantation organ dysfunction.

To explore the role of cAMP, hypoxia was used to simulate a significant component of ischemia, and cardiac transplantation was used as a model of global ischemia and reperfusion. The observations in this study emphasize the potential importance of suppression of endogenous cAMP levels in the pathogenesis of functional abnormalities associated with ischemia/reperfusion. Hypoxia-induced suppression of intracellular cAMP in cultured ECs and smooth muscle cells underscores the relevance of this intracellular messenger when the vasculature is exposed to hypoxia, as occurs during prolonged hypothermic organ storage in the absence of continuous perfusion with oxygenated buffer. Although the decline in cAMP levels in hypoxic ECs results from suppression of adenylate cyclase activity, hypoxia does not substantially alter either basal or stimulated adenylate cyclase activity in vascular smooth muscle cells. The data indicate that this decrease in cellular cAMP levels is associated with a specific increase in soluble PDE activity, notably types III (cGMP inhibited) and IV (cAMP-stimulatable) PDE activity (41). Both types III and IV PDE are found in cultured smooth muscle cells (68); indeed, the presence of soluble type III appears to be relatively specific for smooth muscle cells (68,69). These studies indicate the close link between the cellular response to an environment with low oxygen concentrations and cAMP metabolism. The beneficial role of PDE inhibition during transplantation is underscored by its importance in other models of ischemia and reperfusion. A recent study (67) in a canine model of ischemia/reperfusion has shown that although rolipram administration does not limit myocardial infarct size, it significantly reduces neutrophil production of superoxide in vitro, and limits the "no-reflow" phenomenon wherein coronary blood flow progressively declines following infarction/reperfusion, possibly due to the accumulation of neutrophil aggregates (70–72). Consistent with these observations, a rabbit model of global myocardial ischemia and reperfusion demonstrates that indices of left ventricular performance are improved and histologic evidence of edema and myocardial capillary injury are lessened by either depleting blood of leukocytes or administering a PDE inhibitor prior to the onset of reperfusion (73), and a feline model of stroke demonstrates that inhibition of PDE in vascular smooth muscle is associated with enhanced restoration of blood flow after release of occlusion of the middle cerebral artery (74).

Although the interplay of cAMP and cGMP in smooth muscle cells has yet to be determined, it was recently proposed (75) that a decrease in smooth muscle cGMP content may mediate the observed hypoxic contraction of isolated rat pulmonary arteries. In addition, ischemia/reperfusion induced declines in nitric oxide levels secondary to the quenching effect of oxygen free-radicals (58, 76, 77) would lower the intracellular cGMP content of vascular SHCs, which might in turn cause less inhibition of the type III PDE. Thus, increased levels as well as disinhibition of smooth muscle (type III) PDE would amplify the destruction of intracellular cAMP, accounting for the observed decrease in cAMP levels. Because of these interactions between the cAMP and the cGMP second messenger systems, as well as recent studies which have demonstrated diminished production of nitric oxide by hypoxic/reoxygenated ECs and reduced agonist induced nitric oxide generation by UW preserved hearts (78), it is likely that supplementation of the intra/inter-cellular second messenger pathway involving nitric oxide/cGMP will also enhance vascular homeostasis in the setting of organ transplantation. Recent pilot studies have provided support for this hypothesis in a rat heterotopic transplant model (79). Because the cAMP and nitric oxide/cGMP pathways share many similar features with respect to vascular homeostasis (77), they may provide synergistic benefit during the preservation and reimplantation periods. Consistent with this hypothesis, supplementation of both the cyclic AMP and nitric oxide/cGMP messenger pathways results in unprecedented enhancement of cardiac preservation (up to 24 hours with simple hypothermic storage) in a primate orthotopic model involving cardiopulmonary bypass (80), indicating the relevance of this approach with respect to human heart transplantation, as well as other situations involving ischemia and reperfusion. Based on these considerations, it is proposed that intervention at the level of intra/inter-cellular second messenger pathways during cardiac preservation and reimplantation provides a new approach to the problem of organ preservation. The clinical benefits that should accrue from successfully prolonging the preservation period include more time for better immunologic cross-matching (with attendant reduction in immunologic complications), as well as expanding the donor and recipient pools by reducing geographic constraints, thereby making transplantation more widely available as a therapeutic option.

REFERENCES FOR SECOND SERIES OF EXPERIMENTS:

1. Roberts, A. 1985. Myocardial Protection in Cardiac Surgery. Marcel Dekker, Inc., New York.
2. Wahlberg, J., J. Sourhard, and F. Belzer. 1986. Development of a cold storage solution for pancreas preservation. Cryobiology 23:477–482.
3. Makowka, J., T. Zerbe, and F. Chapman. 1989. Prolonged rat cardiac preservation with UW lactobionate solution. Transplant Proc. 21:1350–1352.
4. Swanson, D., I. Pasaoglu, H. Berkoff, J. Southard, and J. Hegge. 1988. Improved heart preservation with UW preservation solution. J. Heart Transplant 7:456–467.
5. Malhotra, D., A. Zhou, Y. Kong, J. Shapiro, and L. Chan. 1991. Improvement in experimental cardiac preservation based on metabolic considerations. Transplantation 52:1004–1008.
6. Wickens, D., M. Li, G. Arkins, B. Fuller, K. Hobbs, and T. Dormandy. 1987. Free radicals in hypothermic rat heart preservation- prevention of damage by mannitol and desferrioxamine. Free Rad. Res. Comm. 4:189–195.
7. Belzer, F., and J. Southard. 1988. Principles of solid-organ preservation by cold storage. Transplantation 45:673–676.
8. Warnick, C. and H. Lazarus. 1977. Adenine nucleotides during organ storage. Transpl. Proc. IX:1575–1577.
9. Stewart, J., W. Frist, and W. Merrill. 1990. Oxygen scavengers in myocardial preservation during transplantation. Methods in Enzym. 186:742–748.

10. Das, D., J. Russell, and R. Jones. 1991.Reduction of cold injury by superoxide dismutase and catalase. Free Rad. Res. Comm. 12–13 (Pt. 2):653–662.

11. Zimmer, S., K. Ugurbil, S. Michurski, P. Mohanakrishnan, V. Ulstad, J. Foker, and A. From. 1989. Alterations in oxidative function and respiratory regulation in the post-ischemic myocardium. J. Biol. Chem. 12402–12411.

12. Oksendal, A., and P. Jynge. 1986. Protection by verapamil in the calcium paradox: dependence on micromolar calcium. Cardiovasc. Res. 20:845–852.

13. Boggs, B., D. Torchiana, G. Geffin, J. Titus, B. Redonnett, D. O'Keefe, J. Newell, and W. Daggett. 1987. Optimal myocardial preservation with an acalcemic crystalloid cardioplegic solution. J. Thoracic. Cardiovasc. Surg. 93:838–846.

14. Iyengar, J., A. George, J. Russell, and D. Das. 1990. The effects of an iron chelator on cellular injury induced by vascular stasis caused by hypothermia. J. Vasc. Surg. 12:545–551.

15. Liu, X., Engelman, R., J. Iyengar, G. Cordis, and D. Das. 1991. Amiloride enhances postischemic ventricular recovery during cardioplegic arrest. Annals NY Acad. Sci. 639:471–474.

16. Simionescu, N., and M. Simionescu. 1988. *Endothelial Cell Biology*, Plenum Publishing Corp., New York.

17. Simionescu, N., and M. Simionescu. 1991. *Endothelial Cell Dysfunction*, Plenum Publishing Corp., New York.

18. Shreeniwas, R., S. Ogawa, F. Cozzolino, G. Torcia, N. Braunstein, C. Butura, J. Brett, H. Lieberman, M. Furie, and D. Stern. 1991. Macrovascular and microvascular endothelium during long-term hypoxia: alterations in cell growth, monolayer permeability, and cell surface coagulant properties. J. Cell Physiol. 146:8–17.

19. Lefer, A., P. Tsao, D. Lefer, and X. Ma. 1991. Role of endothelial dysfunction in the pathogenesis of reperfusion injury after myocardial ischemia. FASEB J. 5:2029–2034.

20. Minnear, F., A. Johnson, and A. Malik. 1986. β-adrenergic modulation of pulmonary transvascular fluid and protein exchange. J. Appl. Physiol. 60:266–274.

21. Ogawa, S., H. Gerlach, C. Esposito, A. Pasagian-Macaulay, J. Brett, and D. Stern. 1990. Hypoxia modulates the barrier and coagulant function of cultured bovine endothelium: increased monolayer permeability and induction of procoagulant properties. J. Clin. Invest. 85:1090–1098.

22. Hoek, J. 1992. Intracellular signal transduction and the control of endothelial permeability. Lab. Invest. 67:1–4.

23. Archipoff, G., A. Beretz, C. Froger-Leon, C. de la Salle, C. Klein-Soyer, and H. Cazenave. 1991. Opposite regulation by cAMP of thrombomodulin and tissue factor activities on the surface of human saphenous vein endothelial cells in culture. Thromb. and Haemost. 65: 349.

24. Stelzner, T., J. Weil, and R. O'Brien. 1989. Role of cyclic adenosine monophosphate in the induction of endothelial barrier properties. J. Cell Physiol. 139:157–166.

25. Ogawa, S., S. Koga, K. Kuwabara, B. Morrow, S. Morris, J. Bilezikian, S. Silverstein, and D. Stern. 1992. Hypoxia-induced increased permeability of cultured bovine pulmonary and aortic endothelial monolayers occurs through lowering of cellular cAMP levels and is modulated by glucocorticoids. Am. J. Physiol. 262:C546–554.

26. Seibert, A., W. Thompson, A. Taylor, W. Wilborn, J. Barnard, and J. Haynes. 1992. Reversal of increased microvascular permeability associated with ischemia-reperfusion: role of cAMP. J. Appl. Physiol. 72(1):389–395.

27. Haynes, J., J. Robinson, L. Saunders, A. Taylor, and S. Strada. 1992. Role of cAMP-dependent protein kinase in cAMP-mediated vasodilation. Am. J. Physiol. 262:H511–516.

28. Ono, K., and Lindsey, E. Improved technique of heart transplantation in rats. 1969. J. Thoracic and Cardiovasc. Surg. 57 (2): 225–229.

29. Goldblum, S., K. Wu, and M. Jay. 1985. Lung myeloperoxidase as a measure of pulmonary leukostasis in rabbits. J. Appl. Physiol. 59:1978–1985.

30. Colucci, W., T. Brock, M. Gimbrone, and R. Alexander. 1985. Non-linear relationship between $\alpha_1$-adrenergic receptor occupancy and norepinephrine-stimulated calcium flux in cultured vascular smooth muscle cells. Mol. Pharmacol. 27:517–524.

31. Gown, A., A. Vogel, D. Gordon, and P. Lu. 1985. A smooth muscle-specific monoclonal antibody recognizes smooth muscle actin isozymes. J. Cell. Biol. 100:807–813.

32. Koga, S., S. Ogawa, K. Kuwabara, J. Brett, J. Leavy, J. Ryan, Y. Koga, J. Plocinski, W. Benjamin, D. Burns, and D. Stern. 1992. Synthesis and release of Interleukin 1 by reoxygenated human mononuclear phagocytes. J. Clin. Invest. 90:1007–1015.

33. Lowry, O., N. Rosebrough, A. Farr, and R. Randall. Protein measurement with the Folin reagent. 1951. J. Biol. Chem. 193:265–275.

34. Morris, S., H. Tanowitz, S. Factor, J. Bilezikian, and M. Wittner. 1988. Myocardial Adenylate cyclase activity in acute Murine Chagas' disease. Circ. Res. 62:800–810.

35. Bilezikian, J., A. Dornfeld, and D. Gammon. 1978. Structure activity binding analysis of beta adrenergic amines. Biochem. Pharmacol. 27:1445–1454.

36. Salomon, Y., C. Londos, and M. Rodbell. A highly sensitive adenylate cyclase assay. 1974. Anal. Biochem. 58:541–548.

37. Keravis, T., J. Wells, and J. Hardman. 1980. Cyclic nucleotide phosphodiesterase activities from pig coronary arteries: lack of interconvertibility of major forms. Biochem. Biophys. Acta. 613:116–29.

38. Kruskal, W. H. and W. A. Wallis. 1952. Use of ranks in one-criterion analysis of variance. J. Amer. Statist. Assoc. 52:356–360.

39. Dunn, O. J. Multiple contrasts using rank sums. 1964. Technometrics 6:241–252.

40. Kaukel, E., K. Mundhenk, and H. Hilz. 1972. $N^6$-monobutyryladenosine 3':5'-monophosphate as the biologically active derivative of dibutyryladenosine3':5'-monophosphate in HeLa S3 cells. Eur. J. Biochem. 27:197–200.

41. Thompson, W. 1991. Cyclic nucleotide phosphodiesterases: pharmacology, biochemistry, and function. Pharmacol. Ther. 51: 13–33.

42. Rothermel, J., L. Botelho, and H. Parker. 1988. A mechanistic and kinetic analysis of the interactions of the diastereoisomers of adenosine 3',5'-(cyclic) phosphorothioate. Biochem. J. 251:7575–762.

43. Corbin, J., D. Ogreid, J. Miller, R. Suva, B. Jastorff, and S. Doskeland, Studies of cGMP analog specificity and function of the two intrasubunit binding sites of cGMP-dependent protein kinase. J. Biol. Chem. 261:1208–1214, 1986.

44. Hoffman, F., H. Gensheimer, W. Landgraf, R. Hullin, and B. Jastorff. 1985. Diastereomers of adenosine 3',5'-monothiophosphonate (cAMP[S]) antagonize the activation of the cGMP-dependent protein kinase. Eur. J. Biochem. 150:85–88.

45. Jeevanandam, V., M. Barr, J. Auteri, J. Sanchez, G. Ott, F. Schenkel, C. Marboe, C. Smith, and E. Rose. 1991. University of Wisconsin solution for human donor heart preservation: initial clinical experience. Ann. Thorac. Surg. 52:1213–1216.

46. Hale, S., K. Alker, and R. Kloner. 1988. Evaluation of nonradioactive, colored microspheres for measurement of regional myocardial blood flow in dogs. Circ. 78:428–434.

47. Mullane, K., and C. Smith. The role of leukocytes in ischemic damage, reperfusion injury and repair of the myocardium. In *Pathophysiology of Severe Ischemic Myocardial Injury*. H. Piper, editor. Kluwer Academic Publishers/Dordecht, Netherlands. 239–267.

48. Crawford, M., F. Grover, W. Kolb, C. McMahan, R. O'Rourke, L. McManus, and R. Pinckard. 1988. Complement and neutrophil activation in the pathogenesis of ischemic myocardial injury. Circ. 78:1449–1458.

49. Mullane, K., N. Read, J. Salmon, and S. Moncada. 1984. Role of leukocytes in acute myocardial infarction in anesthetized dogs. J. Pharmacol. Exp. Ther. 228:510–522.

50. Lucchesi, B., and K. Mullane. 1986. Leukocytes and ischemia induced myocardial injury. Annu. Rev. Pharmacol. Toxicol. 26:201–224.

51. Schmid-Schoenbein, G., and R. Engler. 1987. Granulocytes as active participants in acute myocardial ischemia and infarction. Am. J. Cardiovasc. Pathol. 1:15–30.

52. Entman, M., L. Michael, R. Rossen, W. Dreyer, D. Anderson, A. Taylor, and C. Smith. 1991. Inflammation in the course of early myocardial ischemia. FASEB J. 5:2529–2537.

53. Ma, X., P. Tsao, and A. Lefer. 1991. Antibody to CD18 exerts endothelial and cardiac protective effects in myocardial ischemia and reperfusion. J. Clin. Invest. 88:1237–1243.

54. Koga, S., D. Han, R. P. Kline, M. C. Oz, R. Nowygrod, D. M. Stern, and D. J. Pinsky. 1992. Electrical Evaluation of Myocardial Viability Following Prolonged Storage of Explanted Hearts, Circulation 86 (4): I-770 (abstr).

55. Zweier, J., P. Kuppusamy, and G. Lutty. 1988. Measurement of endothelial cell free radical generation: evidence for a central mechanism of free radical injury in postischemic tissues. PNAS(USA) 85:4046–4050.

56. Britigan, B. E., T. L. Roeder, and D. M. Shasby. Insight into the nature and site of oxygen-centered free radical generation by endothelial cell monolayers using a novel spin trapping technique. 1992. Blood 79 (3): 699–707.

57. J. L. Zweier. Measurement of superoxide-derived free radicals in the reperfused heart. 1988. J. Biol. Chem. 263(3):1353–1357.

58. Babbs, C., M. Cregor, J. Turek, and S. Badylak. 1991. Endothelial superoxide production in the isolated rat heart during early reperfusion after ischemia. Am. J. Path. 139:1069–1080.

59. Suttorp, N. U. Weber, T. Welsch, and C. Schudt. 1993. Role of phosphodiesterases in the regulation of endothelial permeability in vitro. J. Clin. Invest. 91:1421–1428.

60. Shatos, M., J. Doherty, D. Stump, E. Thompson, and D. Collen. 1990. Oxygen radicals generated using anoxia followed by reoxygenation reduce the synthesis of tissue-type plasminogen activator and plasminogen activator inhibitor-1 in human endothelial cell culture. J. Biol. Chem. 265:20443–20448.

61. Shatos, M., J. Doherty, and J. Hoak. 1991. Role of active oxygen species in the alteration of human vascular endothelial cell function: platelet adherence and prostacyclin release. Arteriosclerosis and Thrombosis 11:594–601.

62. Shatos, M., J. Doherty, T. Orfeo, J. Hoak, D. Collen, and D. Stump. 1992. Modulation of the fibrinolytic response by extracellularly generated oxygen radicals of cultured human vascular endothelium. J. Biol. Chem. 1:597–601.

63. Yoshida, N., D. Granger, D. Anderson, R. Rothlein, C. Lane, and P. Kvietys. 1992. Anoxia/reoxygenation-induce neutrophil adherence to cultured endothelial cells. Am. J. Physiol. 262:H1891–1898.

64. Shreeniwas, R., S. Koga, M. Karakurum, D. Pinsky, E. Kaiser, J. Brett, B. Wolitzky, C. Norton, J. Plocinski, W. Benjamin, D. Burns, A. Goldstein, and D. Stern. 1992. Hypoxia-mediated induction of endothelial cell interleukin $1\alpha$: an autocrine mechanism promoting expression of leukocyte adhesion molecules on the vessel surface. J. Clin. Invest. 90:2333–2339.

65. Pober, J., M. Slowik, L. DeLuca, and A. Ritchie. 1992. Elevated cAMP inhibits endothelial expression of ELAM-1 and VCAM-1 but not ICAM-1. FASEB J. 6:3795.

66. Boxer, L., J. Allen, R. Baehner, and V. Amick. 1980. Diminished polymorphonuclear adherence. J. Clin. Invest. 66:268–274.

67. Simpson, P., J. Schelm, J. Smallwood, M. Clay, and T. Lindstrom. 1992. Inhibition of granulocyte cAMP-phosphodiesterase in vivo is not sufficient to protect the canine myocardium from reperfusion injury. J. Cardiovasc. Pharmacol. 19: 987–955.

68. Rascon, A., S. Lindgren, L. Stavenow, P. Belfrage, K. Andersson, V. Manganiello, and E. Oegerman. 1992. Purification and properties of the cGMP inhibited phosphodiesterase from bovine aortic smooth muscle. Biochim. Biophys. Acta. 1134:149–156.

69. Marivet, M., J. Bourguignon, C. Lugnier, A. Mann, J. Stoclet, and W. Camille-Georges. 1989. Inhibition of adenosine-3',5'-monophosphatephosphodiesterase from vascular smooth muscle by rolipram analogues. J. Med. Chem. 32: 1450–1457.

70. Engler, R., G. Schmid-Schonbein, and R. Pavalec. 1983. Leukocyte capillary plugging in myocardial ischemia and reperfusion in the dog. Am. J. Pathol. 111: 98–111.

71. Engler, R., M. Dahlgren, D. Morris, M. Peterson, and G. Schmid-Schonbein. 1986. Role of leukocytes in response to acute myocardial ischemia and reflow in dogs. Am. J. Physiol. 251: H314–322.

72. Kloner, R. No reflow revisited. 1989. J. Am. Coll. Card. 14:1814–1815.

73. Chen, C., H. Matsuda, Y. Sawa, M. Kaneko, N. Sakagoshi, N. Motonobu, T. Kuratani, A. Amemiya, and Y. Kawashima. 1991. Effect of a cyclic adenosine monophoshate phosphodiesterase inhibitor, DN-9693, on myocardial reperfusion injury. Ann. Thorac. Surg. 52: 495–499.

74. Tanaka, K., F. Gotoh, Y. Fukuuchi, T. Amano, D. Uematsu, J. Kawamura, Y. Takemori, N. Itoh, K. Obara, and K. Muramatsu. 1989. Effects of a selective inhibitor of cyclic AMP phosphodiesterase on the pial microcirculation in feline cerebral ischemia. Stroke 20: 668–673.

75. Mathew, R., H. Omar, P. Cherry, M. Gewitz, and M. Wolin. 1992. Role of cGMP mechanisms in response of rat pulmonary arteries to hypoxia. Am. J. Physiol. 263:H141–146.

76. Lowenstein, C., and S. Snyder. Nitric oxide, a novel biologic messenger. 1992. Cell 70:705–707.

77. Ignarro, L., G. Ross, and J. Tillisch. 1991. Pharmacology of endothelium-derived nitric oxide and nitrovasodilators. West J. Med. 154:51–62.

78. Pearl, J., H. Laks, D. Drinkwater, R. Byrns, L. Ignarro, and P. Chang. 1992. Loss of endothelial-dependent vasodilation and EDRF release following myocardial protection with University of Wisconsion (UW) solution. Circ. 86 (4):I-763 (abstr.)
79. Pinsky, D., S. Koga, M. Oz, A. Morales, R. Nowygrod, P. Cannon, and D. Stern. 1992. Failure of endogenous vasodilation contributes to cardiac graft failure following prolonged storage. Circ. 86(4): I-763 (abstr.)
80. Oz, M., D. Pinsky, S. Koga, V. Jeevanandam, M. Williams, S. Popilskis, C. Marboe, R. Nowygrod, D. Hsu, D. Stern, E. Rose, and R. Michler. 1992. Enhanced donor heart preservation with a novel cAMP based solution. Circ. 86(4): I-840 (abstr.)

THIRD SERIES OF EXPERIMENTS: CARDIAC PRESERVATION IS ENHANCED IN A HETEROTOPIC RAT TRANSPLANT MODEL BY SUPPLEMENTING THE NITRIC OXIDE PATHWAY

Abbreviations

NO= nitric oxide, L-NMMA=$N^G$-monomethyl-L-arginine, 8-Br-cGMP=8-bromoguanosine3',5'monophosphate, NTG= nitroglycerin, L-arg=L-arginine, EC=endothelial cell, HUVEC=human umbilical vein endothelial cell, SOD=superoxide dismutase, LR=lactated Ringer's solution, UW=University of Wisconsin solution.

SUMMARY

Nitric oxide (NO) is a novel biologic messenger with diverse effects, but its role in organ transplantation remains poorly understood. Using a porphyrinic microsensor, the first direct measurements of coronary vascular and endocardial NO production were made. NO was measured directly in the effluent of preserved/heterotopically transplanted rat hearts stimulated with L-arginine and bradykinin; NO concentrations fell from 2.1±0.4 µM for freshly explanted hearts, to 0.7±0.2 µM and 0.2±0.08 µM for hearts preserved for 19 and 38 hrs, respectively. NO levels were increased by superoxide dismutase (SOD), suggesting a role for superoxide-mediated destruction of NO. Consistent with these data, addition of the NO donor nitroglycerin (NTG) to a balanced salt preservation solution enhanced graft survival in a time- and dose-dependent manner, with 92% of hearts supplemented with NTG surviving 12 hrs preservation versus only 17% in its absence. NTG similarly enhanced preservation of hearts stored in University of Wisconsin solution, the clinical standard for preservation. Other stimulators of the NO pathway, including nitroprusside, L-arginine, or 8-bromo-cGMP, also enhanced graft survival, whereas the competitive NO synthase antagonist $N^G$-monomethyl-L-arginine was associated with poor preservation. Likely mechanisms whereby supplementation of the NO pathway enhanced preservation included increased blood flow to the reperfused graft and decreased graft leukostasis. NO was also measured in ECs subjected to hypoxia/reoxygenation, detected based on its ability to inhibit thrombin-mediated platelet aggregation and serotonin release. NO became undetectable in ECs exposed to hypoxia followed by reoxygenation, and was restored to normoxic levels on addition of SOD. These studies suggest that the NO pathway fails during preservation/transplantation due to formation of oxygen free-radicals during reperfusion, which quench available NO. Augmentation of NO/cGMP-dependent mechanisms enhances vascular function following ischemia and reperfusion, and provides a new strategy for transplantation of vascular organs.

Introduction

Nitric oxide (NO) has been ascribed a central role in processes as diverse as neurotransmission and destruction of invading bacteria[1,2]. First identified as an endothelium-derived relaxing factor[3], NO plays a critical role in the maintenance of vascular homeostasis through its interaction with neutrophils, platelets, and cellular components of the vessel wall[4-7]. Because vascular dysfunction leading to organ failure is an important limitation to successful transplantation, the role of the NO pathway in this setting is explored. This series of experiments demonstrates direct measurements of NO production by the coronary vasculature and endocardium, and shows that NO levels are diminished in the cardiac vasculature and endocardium following preservation and transplantation, as well as in endothelial cells subjected to hypoxia and reoxygenation. Augmentation of the nitric oxide pathway significantly enhances preservation in a heterotopic rat model of cardiac transplantation. Application of these principles could have a major impact on the current strategy and success of human organ transplantation.

Materials and Methods

Heterotopic Rat Cardiac Transplant Model
Donor Cardiectomy, Preservation, and Heterotopic Transplant.

Male Sprague-Dawley rats (350 grams, Camm Research, Wayne, N.J.) were used, and harvest, preservation, and transplantation procedures performed as described[8]. Preservation solutions included lactated Ringer's (LR) solution (Baxter, Edison, N.J.), or LR supplemented with nitroglycerin (DuPont, Wilmington, Del.), sodium nitroprusside (Roche Laboratories, Nutley, N.J.), $N^G$-monomethyl-L-arginine (L-NMMA; Chembiochem, Salt Lake City, Utah), L-arginine (Sigma Chemical Co., St. Louis, Mo.), or 8-bromoguanosine3',5'monophosphate (8-Br-cGMP; Sigma). Components were combined within 4 hrs of donor cardiectomy, and preservation solutions were kept at 4° C. All of these solutions were at the pH of LR (6.6). University of Wisconsin solution (UW) was purchased from Dupont. Blood flow was restored to the graft exactly one hour after removal from the cold preservation solution, and pulsation of the donor aortic stump was observed to assure patency of the anastomosis. Ten minutes after removal of the cross-clamp, an electrocardiogram was taken (Grass Polygraph, Quincy, Mass.) and the heart was judged by the same blinded investigators throughout based on the presence/absence of regular contractions and a transplant score (0–5, worst-best, respectively) employing the following criteria: contraction (poor=0, average=1, vigorous=2), tissue turgor (hard=0, average=1, soft=2), and color (dusky=0, pink=1). Overall, a graft was considered to have survived if regular contractions were observed with confirmation of corresponding depolarizations by ECG, with a transplant score≧2.

Perfusion of Donor Grafts[9]

Ten minutes after restoration of blood flow, 0.5 ml of 10 µm diameter microspheres ($10^6$/ml) (E-Z Trac, Los Angeles, Calif.) was injected into the donor aortic root. Deposition of microspheres in ventricular tissue was assessed following alkaline hydrolysis, washing, and counting of microspheres as described[8], with results expressed as number of spheres per (40×) field per gram of ventricle. A minimum of ten fields were counted and the mean ±SEM is reported.

Myeloperoxidase Assay/Histology

Ten minutes following restoration of blood flow, transplanted hearts were excised and the aortic root was flushed for 5 minutes (rate of 2 ml/minute controlled by roller pump) with normal saline (Baxter, Edison, N.J.), the atria and great vessels were removed, and intracavitary blood was evacuated. Remaining ventricular pieces were weighed, homogenized, and myeloperoxidase activity measured as described[10]. For histologic study, cardiac graft samples were fixed in an ascending series of aldehydes, embedded, sectioned, and stained with hematoxylin and eosin.

Nitric Oxide Measurements

Preparation of platelets.

Platelets were obtained from a volunteer who had ingested 650 mg of aspirin 12 hours prior to the experiment, collected and prepared as previously described[11]. Radiolabelled serotonin ($^{14}C$-5-hydroxytryptamine, Amersham, Arlington Heights, Ill.) was incorporated into the platelets by adding 0.5 µCi during the blood collection process. Inhibition of cyclooxygenase was confirmed by the absence of aggregation to 1 mM sodium arachidonate.

Preparation of HUVECS.

HUVECs from fresh human umbilical veins were isolated and grown according to previously published methods[12], and used between the 3rd and 4th passages. HUVEC cyclooxygenase was inhibited with acetylsalicylic acid (1 mmol/L in M199 medium, incubated for 30 minutes at 37° C., and then washed twice with M199 to remove residual acetylsalicylic acid) immediately prior to collagenase digestion. Collagenase type I (4 ml, 200 U/ml, Worthington, Freehold, N.J.) and EDTA mix (2% EDTA in HEPES buffered saline (HBS) pH 7.4, with 1% bovine serum albumin, Sigma) was added to digest ECs from the monolayer, followed by washing twice in an electrolyte buffer (KCl 4.2 mM, $MgSO_4$ 0.5 mM, NaCl 135.5 mM, $Na_2HPO_4$ 6.5 mM, $NaH_2PO_4$ 1.5 mM, and glucose 5.6 mM). An hypoxic environment was administered by placing cells in a specially designed airtight chamber (Coy Laboratory Products, Ann Arbor, Mich.) with a normobaric environment comprised of 90% $N_2$, 5% $H_2$, 5% $CO_2$, and 0% $O_2$. $pO_2$s of 15 Torr in the culture medium were achieved by the use of a palladium catalyst in the chamber to reduce any residual $O_2$. All manipulations, including centrifugation and washing of cells (up to the final aggregometry, or reoxygenation phases as described), were performed within the hypoxia chamber. Reoxygenation was accomplished by removing an aliquot of washed and counted HUVECs in suspension to room air for the indicated duration.

Aggregometry/Serotonin Release.

A Lumiaggregometer (Chronolog, Havertown, Pa.) was used employing a continuously warmed (37°) siliconized glass cuvette containing 58×10[6] platelets, 3 mM calcium chloride, and 2.5 µM imipramine to prevent the reuptake of released serotonin. Platelets were challenged with graded doses of α-thrombin (Sigma) to determine the concentration that caused maximal platelet aggregation (0.3 u/mL in all cases), and this dose was used for all further studies. Hypoxic HUVEC aliquots (66 µL of 1×10[6]/mL) were removed from the chamber and immediately added to the aggregometry cuvette, or exposed to room air for the indicated duration of reoxygenation. Normoxic HUVEC aliquots were prepared identically except that they were maintained in a standard cell culture incubator under ambient conditions. Cell viability between these ECs was comparable by trypan blue exclusion. HUVECs were added just prior to thrombin in the indicated experiments. Interference with light absorption was measured for 3 minutes to obtain platelet aggregation curves, after which the cuvette contents were placed on ice, centrifuged at 5,000 rpm for 5 minutes at 4° C., and 200 µL of supernatant was recovered and counted in a liquid scintillation counter to quantify $^{14}C$-serotonin release. To determine the effects of oxygen free-radicals, bovine erythrocyte superoxide dismutase (SOD, final concentration 32 U/ml; Sigma), was added to the aggregometry cuvette in the indicated experiments just prior to the addition of the HUVEC aliquot. Results are expressed as both aggregometry curves and as % maximal serotonin release as defined by thrombin challenge in the absence of ECs.

Direct Measurement with NO Electrode.

Direct measurement of coronary vascular and endocardial nitric oxide synthesis were made with a porphyrinic microsensor[13] using differential pulse voltammetry or amperometry. Rat hearts were explanted and preserved as described above, and studied fresh (no preservation/transplantation) or after hypothermic preservation in lactated Ringer's (LR) solution, heterotopic transplantation, and 10 minutes of reperfusion. The coronary vasculature was flushed free of blood with LR followed by 4 ml of LR supplemented with L-Arg (2 mM) and bradykinin (6×10[6] M, Sigma), which was recycled (1 ml/min) through the coronary vasculature by flushing down the cross-clamped aortic root. Aliquots of perfusate were immediately transferred to an anaerobic environment for measurements and compared to an aqueous nitric oxide reference. Differential pulse voltammograms were obtained using a sensor (working electrode), saturated calomel electrode reference, and platinum wire-auxiliary electrode, with a pulse amplitude of 40 mV. Endocardial NO was measured by implanting the sensor in the septal endocardium of a freshly explanted or preserved/transplanted heart, and after the baseline stabilization, 6×10[6] M bradykinin was applied and NO release continuously monitored by amperometry at constant potential of 0.63 V.

Measurement of nitric oxide synthase activity[14].

Hearts were either freshly explanted, preserved, or preserved/transplanted (with 10 min. of reperfusion), after which they were excised. The coronary arteries were flushed with physiologic saline, the atria and great vessels excised, and the ventricular cavities rinsed free of residual intracavitary blood. Samples were flash-frozen in liquid nitrogen and stored at −80° C. until the time of assay. Extracts were prepared by homogenizing tissue at 4° C. in the presence of protease inhibitors (aprotinin, epsilon amino caproic acid, PMSF, pepstatin A, and chymostatin), and centrifuging (20,000 rpm×20 min) to remove cellular debris. The extract (20 µg of protein by the method of Lowry[15]) was incubated for 60 min. in the presence of $CaCl_2$ (10 µM), FAD (8 µM), dithiothreitol (60 µM)(Sigma), tetrahydrobiopterin (8 µM; B. Schirks, Switzerland), and $^3H$-L-arginine (0.072 µM, 5 µCi;, Amersham, Arlington Heights, Ill.). Thin layer chromatography (TLC) was performed with 5 µl of the reaction mix, using methanol:chloroform:water:ammonium hydroxide (9:2:8:3) as the running solvent. Silica gel TLC plates (Sigma) were stained with ninhydrin (1 g/500 ml ethanol) and the spots corresponding to L-arginine, L-ornithine, and L-citrulline cut out and counted. The % conversion was defined as the number of counts in the L-citrulline spot divided by the total number of counts (L-arginine+L-ornithine+L-citrulline). Results are expressed as the mean ±SEM of 3 determinations.

Statistics

Graft survival data was analyzed by contingency analysis (chi-square). Transplant scores, microsphere perfusion, myeloperoxidase, NO synthase, and platelet serotonin release data were analyzed using ANOVA for unpaired variables with the Tukey test used to discriminate significant differences between group means. Values are expressed as means ±SEM, with a $p<0.05$ considered statistically significant.

Results and Discussion

Experiments with endothelial cells (ECs) have demonstrated that hypoxia/reoxygenation causes increased leukocyte adhesion and activation, suppression of the cell surface anticoagulant cofactor thrombomodulin along with induction of prothrombotic activity, and increased permeability of the EC monolayer[12,16,17]. Since nitric oxide (NO) prevents neutrophil and platelet adherence[5,6], and enhances endothelial barrier function[18], this EC model of hypoxia/reoxygenation was used to simulate a significant component of ischemia/reperfusion to study the role of NO. Cultured ECs were exposed to a level of hypoxia comparable to that measured within the cardiac vasculature of an explanted heart after overnight storage ($pO_2$~18–20 torr), and NO production was evaluated by the ability of ECs to inhibit thrombin-induced platelet aggregation and serotonin release[11] (FIG. 1A, aggregometry curves and bar graph). Inhibition of platelet aggregation by normoxic ECs (FIG. 1B) was blocked by hemoglobin (FIG. 1C), validating that NO was the antiaggregatory agent. Exposure of ECs to hypoxia for 16 hrs did not significantly alter their capacity to block platelet aggregation (FIG. 1D), indicating NO production was maintained. However, exposure of ECs to hypoxia followed by reoxygenation in room air was associated with undetectable levels of NO (FIG. 1E). Since reoxygenated ECs produce oxygen free-radicals which can destroy NO[19,20], the free-radical scavengers superoxide dismutase (SOD) (FIG. 1F) or butylated hydroxytoluene (BHT, data not shown) were added and found to restore NO levels. This suggested that oxygen free-radicals quenched NO during reoxygenation, a process which was maximal by 10–15 minutes after reoxygenation in the assay system. These results are consistent with observations from experiments with coronary artery rings from feline hearts subjected to ischemia/reperfusion in vivo, which demonstrate impaired vasorelaxation only after reperfusion (within minutes)[21]. This rapid time course for generation of oxygen free-radicals is also consistent with that shown in experiments using an electron paramagnetic resonance spin trap[22,23].

In order to further evaluate the role of NO, direct measurements of NO were made in rat hearts subjected to preservation/heterotopic transplantation using a highly sensitive and specific NO sensing electrode[13]. The coronary vasculature of freshly explanted or preserved/transplanted hearts was flushed free of blood, perfused with both bradykinin and L-arginine (L-Arg), and NO was measured by differential pulse voltammetry. NO concentration decreased from 2.1±0.4 µM (n=5) for freshly explanted to 0.7±0.2 µM (n=4) and 0.20±0.08 µM (n=4) for hearts preserved for 19 and 38 hours, respectively (FIG. 2A, B). The perfusate from transplanted hearts consistently demonstrated lower NO levels than freshly explanted hearts, with levels augmented by the addition of superoxide dismutase (FIG. 2C). Addition of the competitive NO synthase inhibitor $N^G$-monomethyl-L-arginine (L-NMMA) blocked further NO production, but the addition of the cGMP analog (8-Br-cGMP) to the preservation solution did not alter NO levels following transplantation (data not shown). In situ endocardial measurements of NO using an implanted microsensor demonstrated a steady increase of NO concentration to a plateau of 0.67±0.06 µM (n=3) and 0.17±0.05 µM (n=3) following bradykinin challenge of freshly explanted and preserved (38 hrs) hearts, respectively (FIGS. 3A, B). These data indicate that NO levels are markedly suppressed following preservation/transplantation.

Because SOD in the flush solution increased NO levels of transplanted hearts (FIG. 2C), this suggested that NO was being quenched, but its synthesis remained unimpaired following reperfusion. To establish this further, nitric oxide synthase activity was assayed in extracts of freshly explanted, preserved, and preserved/transplanted hearts, as well as in preserved/transplanted hearts whose preservation solutions were supplemented with nitroglycerin or 8-Br-cGMP. Because the conversion of L-arginine to L-citrulline is stoichiometric and reflects the production of nitric oxide[1], this conversion was measured using a modification of the thin layer chromatographic method described by Stuehr, et. al.[14]. These results (FIG. 4) showed that the activity of nitric oxide synthase following transplantation is similar regardless of whether or not the LR has been supplemented with nitroglycerin or 8-Br-cGMP. There was, however, an increase in nitric oxide synthase activity when any group of transplanted hearts was compared with preserved hearts. The significance of this finding is unclear, but may reflect an increased level of nitric oxide synthase in the cells present in the transplanted organ or recruited during the reperfusion period. This increase in graft capacity to generate NO after transplantation was not translated into increased NO availability (as measured with the NO electrode). These data, together with the hypoxic/reoxygenated endothelial cell data described previously, support the hypothesis that NO synthesis continues following reimplantation, but NO availability during reperfusion is reduced due to its rapid destruction.

Based on these observations, it was hypothesized that supplementation of the NO pathway by addition of NO/cGMP agonists during preservation would extend preservation and enhance vascular function. Cardiac grafts were assessed by both ECG and a scoring system based on blinded evaluation of color, turgor, and contractility. The duration of reperfusion after transplantation was chosen as 10 minutes because pilot studies demonstrated that hearts which did not survive became dark, hard, and failed to contract (by visual inspection with absent depolarizations by ECG) within 1–2 minutes following reperfusion. Failed grafts never regained function, and surviving grafts continued to function for several hours of observation. Because of these observations, as well as those of others[23] suggesting that oxygen free-radicals are generated within minutes by reperfused hearts, evaluation was made grafts at 10 minutes of reperfusion. Only 17% of hearts survived a 12 hour storage period when preserved in lactated Ringer's alone (FIG. 5A). In sharp contrast, addition of the endothelium-independent vasodilator nitroglycerin (NTG; 0.1 mg/ml) resulted in 92% survival, with scores closely parallelling survival (FIG. 5A) in all experiments. This beneficial effect of NTG on cardiac preservation was dose-dependent (FIG.

5B), and was also evident when NTG was added to the clinical standard University of Wisconsin (UW) solutions[24-26]; only 35% of hearts preserved with UW alone survived a preservation period of 24–28 hours, whereas addition of NTG (0.1 mg/ml) increased survival to 100% (n=20 and 6 respectively, p<0.025). These data are consistent with the observation that there is impaired endothelium-dependent vasodilation following the use of UW for cardiac preservation[27]. Another EC-independent vasodilator (nitroprusside) also enhanced preservation, as did L-Arg, an endogenous substrate for NO synthase (FIG. 5C). The competitive nitric oxide synthase antagonists $N^\omega$-nitro-L-arginine or L-NMMA blocked the beneficial effects of L-Arg, and grafts preserved in the presence of L-NMMA alone had the poorest survival of any group (0%, n=6; FIG. 5C). Consistent with an integral role of the NO pathway in cardiac preservation, 8-bromoguanosine 3':5'-cyclic monophosphate (8-Br-cGMP), a membrane permeable cGMP analog which has its site of action distal to NO (i.e., cGMP-dependent protein kinase)[28], enhanced cardiac preservation in a dose-dependent manner (FIG. 5D).

In order to elucidate the mechanism(s) underlying NO/cGMP enhancement of cardiac preservation, blood flow after transplantation was quantified in a series of both successful and failed grafts by infusion of latex microspheres[9], with histologic confirmation of their deposition in the microvasculature. Grafts which failed after implantation had 4 times less flow than those which were successful (FIG. 6A). Stimulation of the NO/cGMP pathway with either NTG, nitroprusside, L-Arg, or 8-Br-cGMP was associated with enhanced blood flow, whereas antagonism of L-Arg with L-NMMA was associated with decreased blood flow (FIG. 6B). Because infiltration of neutrophils into ischemic and reperfused myocardium contributes significantly to tissue damage[29-31], the role of the NO pathway was also explored. NTG in the preservation solution was associated with a marked decrease in neutrophil infiltration following cardiac transplantation, as determined by histology (FIG. 6C) and by quantification of the neutrophil enzyme myleoperoxidase (FIG. 6D).

These data emphasize the importance of the NO/cGMP pathway in vascular homeostasis. Because hypoxia also suppresses $EC^{32}$ and smooth muscle cell[8] cAMP levels, thus impairing another endogenous vasodilator system which also modulates vascular permeability and leukocyte-EC interactions[33,34], designed an organ storage solution containing agonists of both pathways (dibutyryl-cAMP, 2 mM and NTG, 0.1 mg/ml) has been designed. This is a highly effective preservation solution in both heterotopic rat and orthotopic baboon cardiac transplant models[35], the latter involving cardiopulmonary bypass (identical to human heart transplantation). Since baboon hearts were successfully preserved for an unprecedented 24 hours with simple hypothermic storage in the supplemented solution, this suggests the potential significance of maintaining the integrity of intra/intercellular second messenger pathways in ischemic and reperfused tissue. These data are consonant with that of other cardiac models, which infer by indirect measurements that the coronary vasculature produces $NO^{36}$ and that the NO pathway is depressed in the setting of ischemia and reperfusion[37,38]. This study represents the first application of these principles to the setting of organ preservation for transplantation, with direct measurements demonstrating that coronary vascular and endocardial NO levels are diminished following transplantation, and that supplementation of the NO pathway significantly enhances graft survival following prolonged preservation. These results are likely to apply to all vascular organs, and suggest novel ways to improve organ preservation for transplantation as a strategy to treat human disease.

FOURTH SERIES OF EXPERIMENTS: THE NITRIC OXIDE/CYCLIC GMP PATHWAY IN ORGAN TRANSPLANTATION: CRITICAL ROLE IN SUCCESSFUL LUNG PRESERVATION

Abbreviations

NO=Nitric oxide; cGMP=guanosine 3'5' cyclic monophosphate; 8-Br-cGMP=8-bromoguanosine-3'5' cyclic monophosphate; Rp-8-pCPT-cGMPS=R isomer of 8-(4-chlorophenylthio)guanosine-3'5'-cyclic monophosphorothioate; M&B 22948=2-o-propoxyphenyl-8-azapurin-6-one; PVR=pulmonary vascular resistance; PAF=pulmonary arterial flow; PAP=pulmonary arterial pressure; PMN=polymorphonuclear leukocyte.

Summary

Reestablishment of vascular homeostasis following ex vivo preservation is a critical determinant of successful organ transplantation. Because the nitric oxide (NO) pathway modulates pulmonary vascular tone and leukocyte/endothelial interactions, and reactive oxygen intermediates are formed in abundance during reperfusion of the lungs, it was hypothesized that NO (and hence cGMP) levels would be depressed following pulmonary reperfusion, leading to increases in pulmonary vascular resistance and leukostasis following transplantation. These experiments were designed to ascertain NO and cGMP levels in lungs following reperfusion, and to determine whether supplementation of the NO pathway at the level of cGMP might enhance lung preservation for transplantation. Using an orthotopic rat model of lung transplantation, a porphyrinic microsensor was used to make the first direct in vivo measurements of pulmonary NO. NO levels plummeted immediately upon reperfusion of the transplanted lung, with levels increased by superoxide dismutase. Because there was a significant decline in cGMP levels (by radioimmunoassay) in preserved lungs following reperfusion, this led us to implement a strategy to improve lung preservation for transplantation by buttressing the NO pathway at the level of cGMP by adding the membrane permeant cGMP analog 8-Br-cGMP to the preservation solution. Compared with grafts stored in its absence, grafts stored with supplemental 8-Br-cGMP and evaluated 30 minutes following reperfusion demonstrated lower pulmonary vascular resistances with increased graft blood flow, improved arterial oxygenation, decreased neutrophil infiltration, and improved recipient survival. These beneficial effects were dose-dependent, mimicked by the type V phosphodiesterase inhibitor M&B 22948, and inhibited by the cyclic GMP-dependent protein kinase antagonist Rp-8pCPT-cGMPS. These data show that NO and cGMP levels are decreased following pulmonary reperfusion, and that augmenting the NO pathway at the level of cGMP improves graft perfusion, reduces graft leukostasis, improves arterial oxygenation, and significantly enhances recipient survival following lung transplantation.

Introduction

One of the major limitations in the transplantation of solid organs has been the short interval which the organ can survive outside of the body in transit from donor to recipient[1]. This is especially problematic during clinical lung transplantation, where the inability to preserve lungs beyond 4–6 hours is insufficient for immunologic cross-matching, and impedes efforts at multiple or distant organ procurement, and the perioperative morbidity and mortality remain high[2–6]. Current lung preservation strategies have focussed on preventing oxygen free radical damage to the pulmonary parenchyma[7–12], as well as optimizing electrolyte and solute concentrations of the preservation solution[1], but lungs still fail following transplantation with elevated pulmonary vascular resistance, neutrophil infiltration, and poor gas exchange as cardinal features[12].

Recent studies have indicated that nitric oxide (NO) has multiple roles in maintaining the homeostatic properties of the vasculature[13–18]. NO released from endothelial cells results in vascular smooth muscle relaxation[13], reduced neutrophil adhesivity to endothelium[19], reduced platelet aggregation[20], and maintenance of endothelial barrier function[21]. Experiments in which nitric oxide synthase antagonists have been given to sheep[22], pigs[23], lambs[24], cats[25], rabbits[26], and rats[27] have shown that endogenously produced NO is important in stimulating basal cGMP production in the lungs and in regulating pulmonary vascular tone. Because the NO pathway is perturbed following cardiac ischemia and reperfusion[28], it was hypothesized that diminished NO availability during the immediate reperfusion period, likely due to the formation of reactive oxygen intermediates, would be an important contributor to the elevated pulmonary vascular resistance and neutrophil recruitment which occurs following lung transplantation. These experiments were designed to measure pulmonary NO and cGMP levels following reperfusion, and to determine whether augmentation of the NO pathway at the level of cGMP would enhance lung preservation for transplantation.

Methods

Donor Lung Harvest:

Orthotopic rat left lung transplantation was accomplished using inbred male Lewis rats (250–300 gms), using a modification of a previously described technique[29]. The donor rat was anesthetized and heparinized (500 U intravenously), and endotracheal intubation was performed by inserting a 16 gauge angiocatheter into the trachea using blunt cervical dissection, after which the rat was ventilated with room air at a constant rate (100 breaths/minute) and tidal volume (2.5 ml), using a Harvard rodent ventilator. The donor left lung and hilum were exposed, the superior vena cavae ligated, the inferior vena cava was cannulated, and cold (4° C.) preservation solution infused at a constant pressure (<20 mm Hg) so as to avoid variation in endothelial shear by arbitrary infusion pressure. The pulmonary artery (PA) and pulmonary vein (PV) were divided, the bronchus ligated with the lung partially inflated and then divided, and the lung removed. The vascular stumps were each pulled through a small plastic cylinder, and a lip of vessel was turned back around the edge and secured in place with a suture to form a "cuff." A small plastic cylinder was inserted into the bronchial stump and secured, and the lung was then wrapped in gauze and submerged in cold preservation solution for the desired interval.

Orthotopic Transplantation:

The recipient rat (gender/size/strain-matched) was similarly anesthetized and intubated (ventilated with 100% oxygen), but not heparinized. A left thoracotomy was performed, the hilum was dissected, and the left bronchus, PA, and PV were isolated, cross-clamped, divided and the native lung was removed from the field. The PA and PV stumps were rinsed with heparinized saline to remove any clot. The donor lung was brought onto the surgical field, and the cylinder (bronchus) and cuffs (PA and PV) were connected rapidly to their respective structures with a simple staying suture. This cuff technique permitted rapid approximation of donor and recipient tissues with no contact of a foreign substance with the luminal vascular surface. The hilar cross-clamp was released, re-establishing blood flow, and the bronchus tie was removed, enabling gas exchange. A snare was then passed around the right PA, and a Millar catheter (2F; Millar Instruments, Houston, Tex.) was introduced through a small hole (surrounded by a pursestring) into the main PA; similarly, a Millar catheter was introduced into the left atrium (LA). A flow probe (Transonics, Ithaca, N.Y.) was then placed around the main PA. Arterial blood gas sampling performed via the left femoral artery.

Measurement of lung graft function:

Online hemodynamic monitoring was accomplished using MacLab and a Macintosh IIci computer. The hemodynamic parameters that were measured included PA pressure (mm Hg), blood flow (ml/min), LA pressure (mm Hg), as well as arterial oxygen tension (mm Hg) during inspiration of 100% oxygen; $pO_2$ was analyzed with a model ABL-2 dissolved gas analyzer (Radiometer, Copenhagen, Denmark). Pulmonary vascular resistances (PVRs) were calculated as [mean PA pressure-LA pressure]/PA flow. The native lung supported the recipient during the period of warm ischemia (the period during which the donor lung was removed from cold preservation until the time of reperfusion, <10 min. in all instances), but immediately following rapid hemodynamic instrumentation and acquisition of baseline measurements, the native (right) PA was then ligated, and serial measurements (representative solely of the transplanted lung) were taken every five minutes for 30 minutes. Because the native lung was effectively removed from the circulation by ligation of the right PA, these measurements represent function of the transplanted lung. Recipient death was identified by the cessation of cardiac mechanical activity observed through the thoracotomy.

Preparation of preservation solution:

Preservation solutions were freshly made and coded by a technician not otherwise involved in the experiments, according to a general plan which included both control and experimental groups. The base preservation solution consisted of either lactated Ringer's (LR) solution (sodium, 130 mEq, potassium, 4 mEq, calcium, 3 mEq, chloride, 109 mEq, lactate, 28 mEq; Baxter, Deerfield Ill.) or modified Euro-Collins (EC) solution ($Na^+$ 10 mEq/L; $K^+$ 115 mEq/L, $Cl^-$ 15 mEq/L, $HPO_4{--}$ –85 mEq/L, $H_2PO_4^-$ 15 mEq/L, $HCO_3{-}$ 10 mEq/L, (Baxter Healthcare, Deerfield Ill.)). Magnesium sulfate (10 ml of 10% solution) and glucose (50 ml of a 50% solution) were added to each liter prior to use. 8-bromoguanosine 3',5'cyclic monophosphate (8-Br-cGMP) was purchased from Sigma Chemical Co. (St. Louis, Mo.). Rp-8-pCPT-cGMPS was purchased from Biolog (La Jolla, Calif.), and M&B 22948 was a kind gift from Rhone Poulenc Rorer (Essex, UK).

Direct Measurement with NO Electrode

Ex vivo measurements:

Direct measurement of pulmonary NO production was made using a porphyrinic microsensor[30] and differential pulse voltammetry. Pieces of rat lung of equal weight (40±4 mg) were harvested following 6 hrs of hypothermic preservation in LR alone, or 6 hrs of preservation followed by orthotopic transplantation and 30 minutes of reperfusion as described above. These pieces were placed in a vial containing 2 mL of LR and equilibrated to 37° C. under ambient conditions. Differential pulse voltammograms (current [proportional to NO concentration] versus potential) with pulse amplitude of 40 mV were obtained with a sensor placed on the tissue surface. A saturated calomel reference electrode (SCE) and platinum wire (auxiliary electrode) were immersed in the LR solution. The sensor is a working electrode at which oxidation of NO occurs, resulting in an electric current (which flows between working and auxiliary electrodes). The reference electrode is used to monitor the potential of the working electrode. NO concentrations measured ex vivo have been normalized, and are reported as per 40 mg of tissue. An aqueous NO solution prepared as previously described[31] was used to calibrate the sensor.

In vivo measurements:

Measurements of nitric oxide concentrations in vivo were performed with a two electrode system using a porphyrinic sensor as a working electrode and a platinum wire as an auxiliary/reference electrode. The porphyrinic sensor with a flexible base was lowered onto the exposed surface of the lung using a micromanipulator. A small piezoelectric signal (mechanically generated current) was used to indicate that the sensor had made contact with the tissue surface. NO measurements were begun once the flexible sensor assumed an L-shaped configuration on the tissue surface and the platinum wire was connected to adjacent tissue. Continous amperometric (current-time) measurements were obtained at a constant potential of 0.68 V, during the period of warm ischemia (after the lung was sewn in place but not yet reperfused) and continously as the vascular cross-clamp was released and reperfusion initiated. Topical application of the calcium ionophore (A23187, 9.5 µM; Sigma) and superoxide dismutase (100 U/ml; Sigma) was applied as monitoring was continued.

Myeloperoxidase assay.

Thirty minutes following restoration of blood flow, transplanted lungs were excised, rinsed briskly in physiologic saline, and snap frozen in liquid nitrogen until the time of assay. These lungs were then homogenized in phosphate buffer (50 mM; pH 6.0, 5 ml/gm of tissue) containing hexadecyltrimethylammonium bromide (0.5%; HTAB, [Sigma]) and frozen at −80° C. The myeloperoxidase assay was performed, as described[32], by thawing the sample, centrifuging at 40,000 g for 15 minutes at 4° C., and decanting the supernatant, which was assayed for myeloperoxidase activity using standard chromogenic spectrophotometric technique: test sample (0.03 ml) was added to sample buffer (0.97 ml of 50 mM phosphate buffer, pH 6.0) containing O-dianisidine dihydrochloride (Sigma), hydrogen peroxide (0.006%), and change in absorbance at 460 nm was measured over 1 min (increase in OD was linear over this time interval).

NO synthase assay and radioimmunoassay for cGMP:

Lungs were preserved for 6 hours in Eurocollins (as described above), and then either snap frozen in liquid nitrogen, or reperfused for 30 minutes with oxygenated LR (37° C., 3 ml/min), after which the tissue was snap frozen in liquid nitrogen. Tissue was then assayed for cGMP by adding tris-buffered saline with 0.3 mM isobutylmethylxanthine (IBMX; Sigma) and then homogenizing for 60 seconds at 4° C., followed by the addition of ice-cold trichloroacetic acid (6%) to further lyse cells and precipitate proteins. The trichloroacetic acid-soluble supernatant was extracted five times with water-saturated ether, dried, and the pellet resuspended in sodium acetate buffer (pH 6.2). A radioimmunoassay was then performed for cGMP according to the manufacturer's instructions (New England Nuclear, Boston, Mass.), as has been reported previously for cAMP[33]. Protein content was determined by the method of Lowry[34] after solubilizing TCA precipitated protein with sodium dodecyl sulfate (2%). Results are reported as pmol cGMP/mg protein, and expressed as the means ±SEM of duplicate determinations. Alternatively, NO synthase was measured in the tissue samples as follows[35]; extracts were prepared from the snap frozen tissue samples by homogenizing tissue at 4° C. in the presence of protease inhibitors (aprotinin, epsilon amino caproic acid, PMSF, pepstatin A, and chymostatin), and centrifuging (20,000 rpm×20 min) to remove cellular debris. The extract (20 µg of protein) was incubated for 60 min. in the presence of $CaCl_2$ (10 µM), FAD (8 µM), dithiothreitol (60 µM) (Sigma), tetrahydrobiopterin (8 µM; B. Schirks, Switzerland), and $^3$H-L-arginine (0.072 µM, 5 µCi, Amersham, Arlington Heights, Ill.). Thin layer chromatography (TLC) was performed with 5 µl of the reaction mix, using methanol:chloroform:water:ammonium hydroxide (9:2:8:3) as the running solvent. Silica gel TLC plates (Sigma) were stained with ninhydrin (1 g/500 ml ethanol) and the spots corresponding to L-arginine, L-ornithine, and L-citrulline cut out and counted. The % conversion was defined as the number of counts in the L-citrulline spot divided by the total number of counts (L-arginine+L-ornithine+L-citrulline). Results are expressed as the mean ±SEM.

Statistics:

Data were analyzed by Students' t-tests when two treatments were being compared, or by analysis of variance for experiments in which three or more variables were being compared. In the latter case, post hoc comparisons of treatment groups were tested using Tukey's procedure. Recipient survival data was evaluated using contingency analysis with the Chi square statistic. Values are expressed as means ±SEM, with a $p<0.05$ considered statistically significant.

Results

Figure 1B:
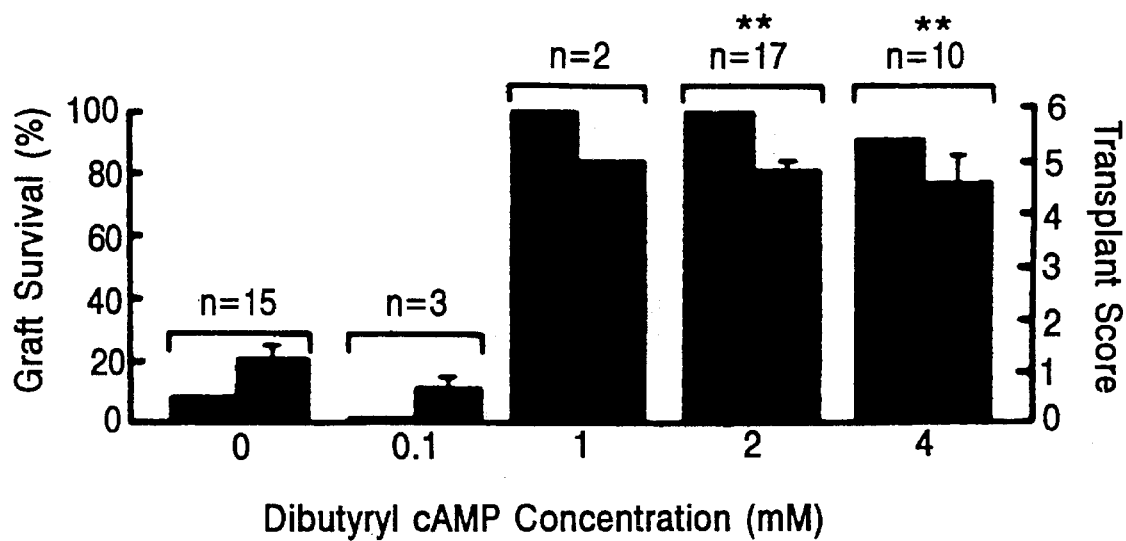

Differential pulse voltammograms employing a porphyrinic microsensor were used to directly measure NO production by same-sized biopsies of fresh lungs (FIG. 1A, line a), lungs which had been preserved for 6 hours at 4° C. in LR (FIG. 1A, line b), as well as lungs which had been similarly preserved but reimplanted into a recipient and reperfused for 10 min. (FIG. 1A, line c). Fresh lung tissue generated considerable NO (700±80 nM; FIG. 1B, bar 1), and lung tissue subjected to preservation alone (i.e., no reimplantation) also produced NO, though at reduced levels (200±70 nM; FIG. 1B, bar 2). In contrast, negligible NO was measured from tissue samples from lungs which were identically preserved and then reimplanted (10±8 nM, p<0.001; FIG. 1B, bar 4). In view of the association of reperfusion with the largest fall in detectable NO, it was logical to consider the likelihood that reactive oxygen intermediates generated following reestablishment of blood flow to the graft were having a significant role in NO inactivation. Consistent with this hypothesis, addition of superoxide dismutase to the solution in which preserved/reimplanted lungs were immersed during NO measurement resulted in a large rise in detectable NO levels (~25 fold increase; FIG. 1B, bar 5), whereas a much smaller increase (from 200 to 300 nM, a 50% increase) was observed with the addition of superoxide dismutase to lungs subjected to preservation alone without reimplantation. (FIG. 1B, bar 3).

Figure 12A:
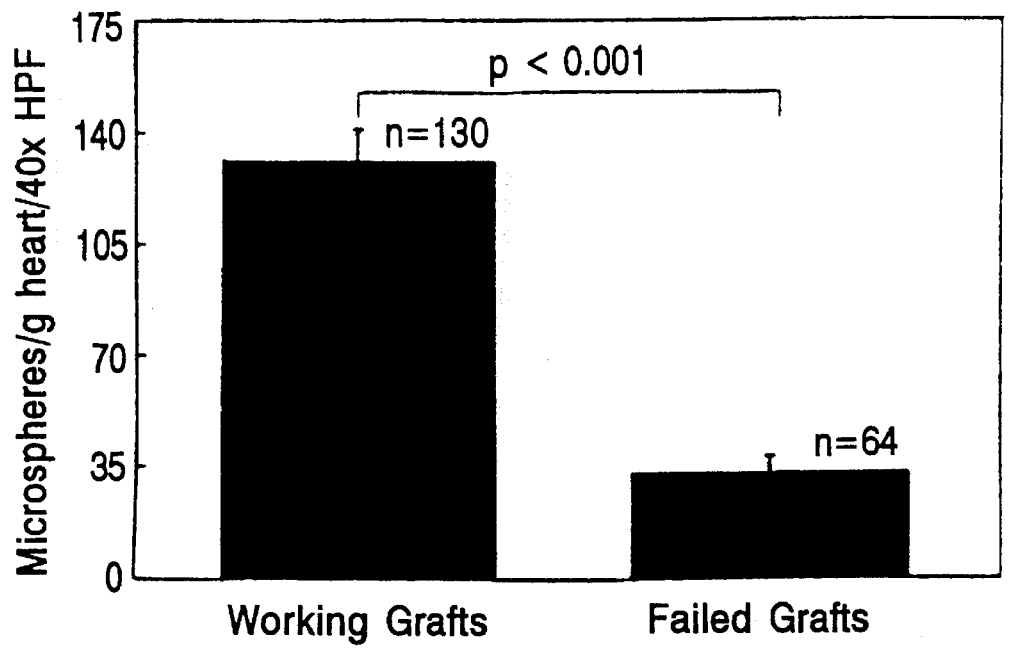
FIGS. 12A–D. Effect of the nitric oxide pathway on graft blood flow and leukostasis. Blood flow to transplanted hearts was evaluated by injecting 10 µm latex microspheres into the donor aortic root and quantifying as described in the methods section. (A) Hearts which failed after transplantation had fewer microspheres/g of ventricle than those which survived the preservation/transplantation process. (B) Preservation/transplantation as described in FIG. 5D above demonstrated that stimulation of the nitric oxide/cGMP pathway was associated with higher blood flows in cardiac grafts. In contrast, antagonism of this pathway was associated with lower blood flows. (C) Transplanted hearts preserved for 12 hours in LR alone demonstrated a prominent band of neutrophils adherent to the vasculature (FIG. 12C-1), whereas the addition of NTG (0.1 mg/ml) to the preservation solution under identical preservation/transplantation conditions was not associated with neutrophil accumulation (FIG. 12C-2). (D) Quantification of cardiac neutrophil deposition by assessing myeloperoxidase activity as descibed[10], normalized to ventricular weight. Hearts preserved for 12 hours in LR alone showed a ≈10-fold increased accumulation of leukocytes after transplantation compared with hearts preserved similarly in LR supplemented with NTG (0.1 mg/ml).
Figure 12B:
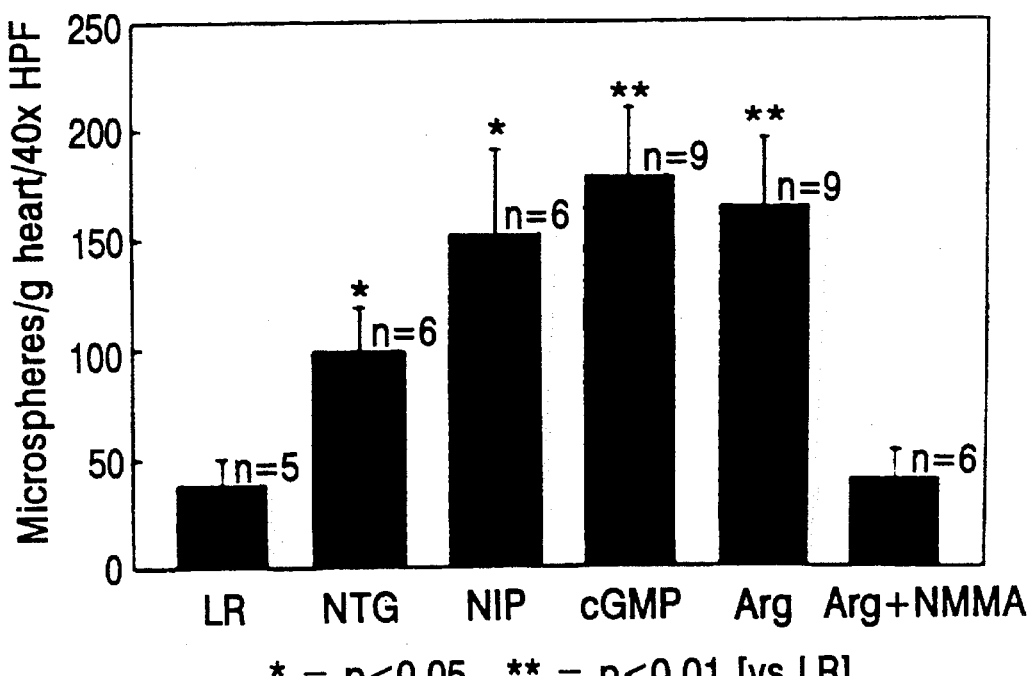
Figures 1, 2, 12C:
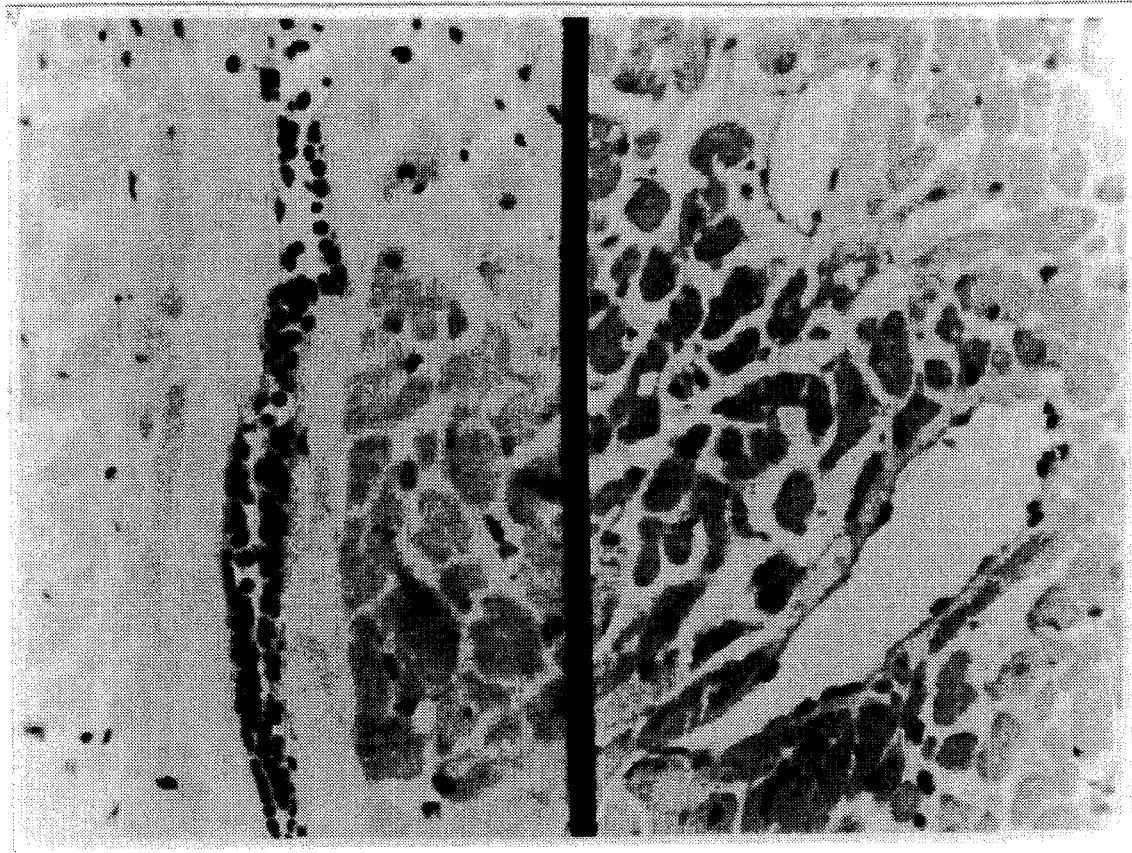
Figure 12D:
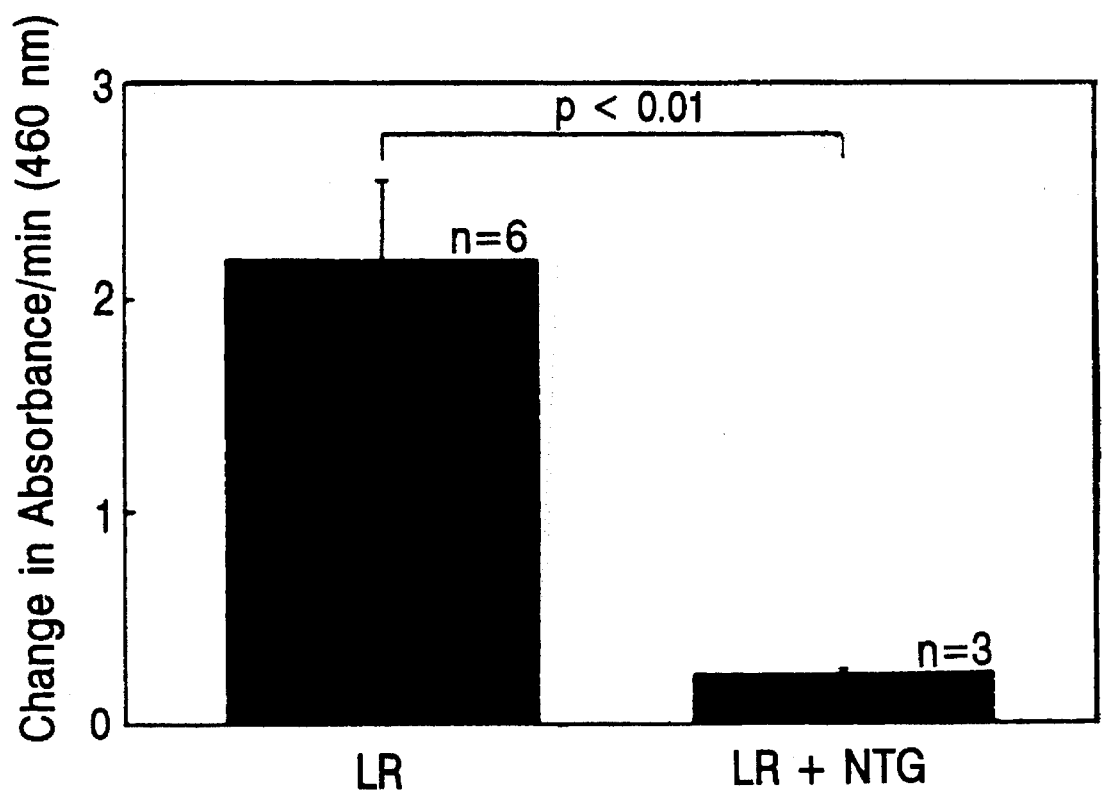
Figure 13A:
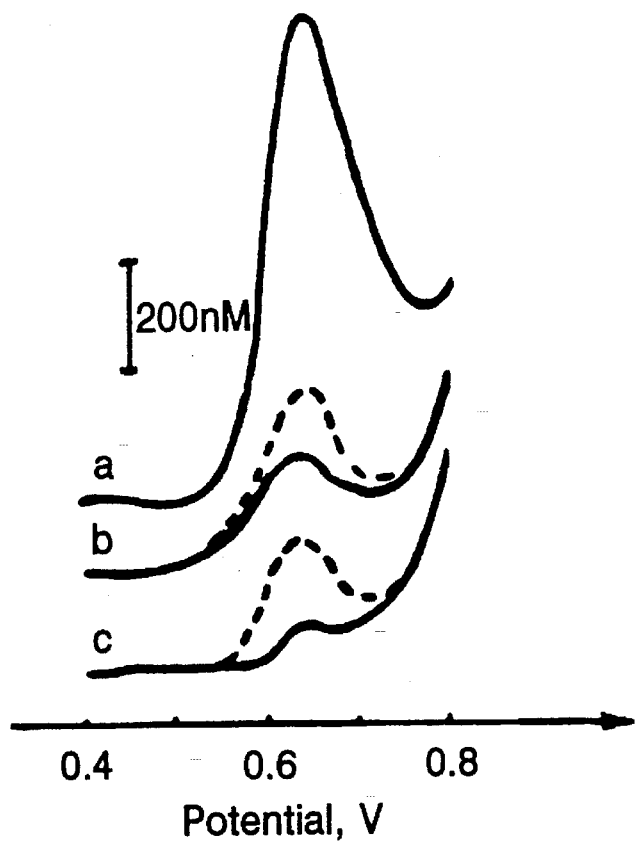
FIGS. 13A–E. Representative differential pulse voltammograms (current-concentration versus potential) of nitric oxide obtained with a porphyrinic microsensor; (a) fresh lung, (b) lung preserved for 6 hours in LR, (c) lung preserved for 6 hours in LR and then transplanted. Solid lines and dashed lines represent voltammograms obtained in the absence and presence of SOD (100 U/ml), respectively. B. Mean concentration of nitric oxide in (1) fresh lung (n=6), (2) lung preserved for 6 hrs in LR (n=7), (3) lung preserved for 6 hrs in LR, after which NO was measured in the presence of SOD (n=7), (4) lung preserved for 6 hrs in LR and then transplanted/reperfused (n=5, $p<0.001$), and (5) same as (4) but NO was measured in the presence of SOD (n=5). C. Amperogram (current-concentration versus time) recorded in vivo with a porphyrinic microsensor placed on the surface of a transplanted lung. D. cGMP levels measured by radioimmunoassay in lungs preserved for 6 hrs in EC (P) or preserved for 6 hrs in EC followed by reperfusion (P/R) (n=5 for each condition). E. Nitric oxide synthase activity as measured by the production of $^3H$-L-citrulline from $^3H$-L-arginine, with conditions as described in part D (n=5 for each condition). Values shown are means ± SEM, where * indicates $p<0.05$.
Figure 13B:
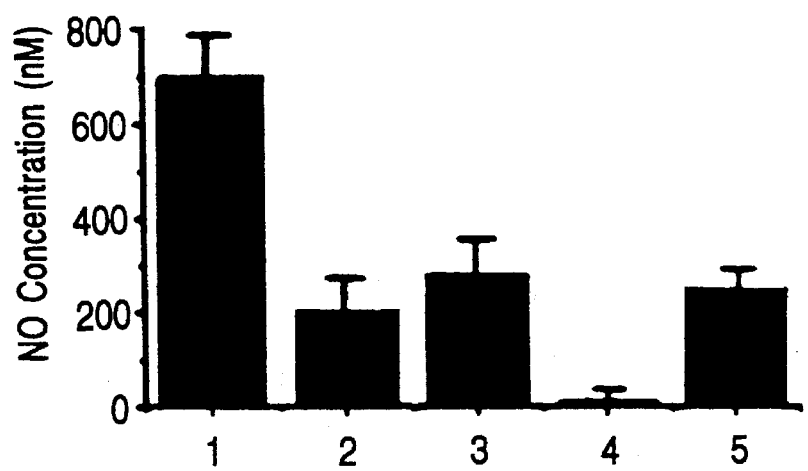
Figure 13C:
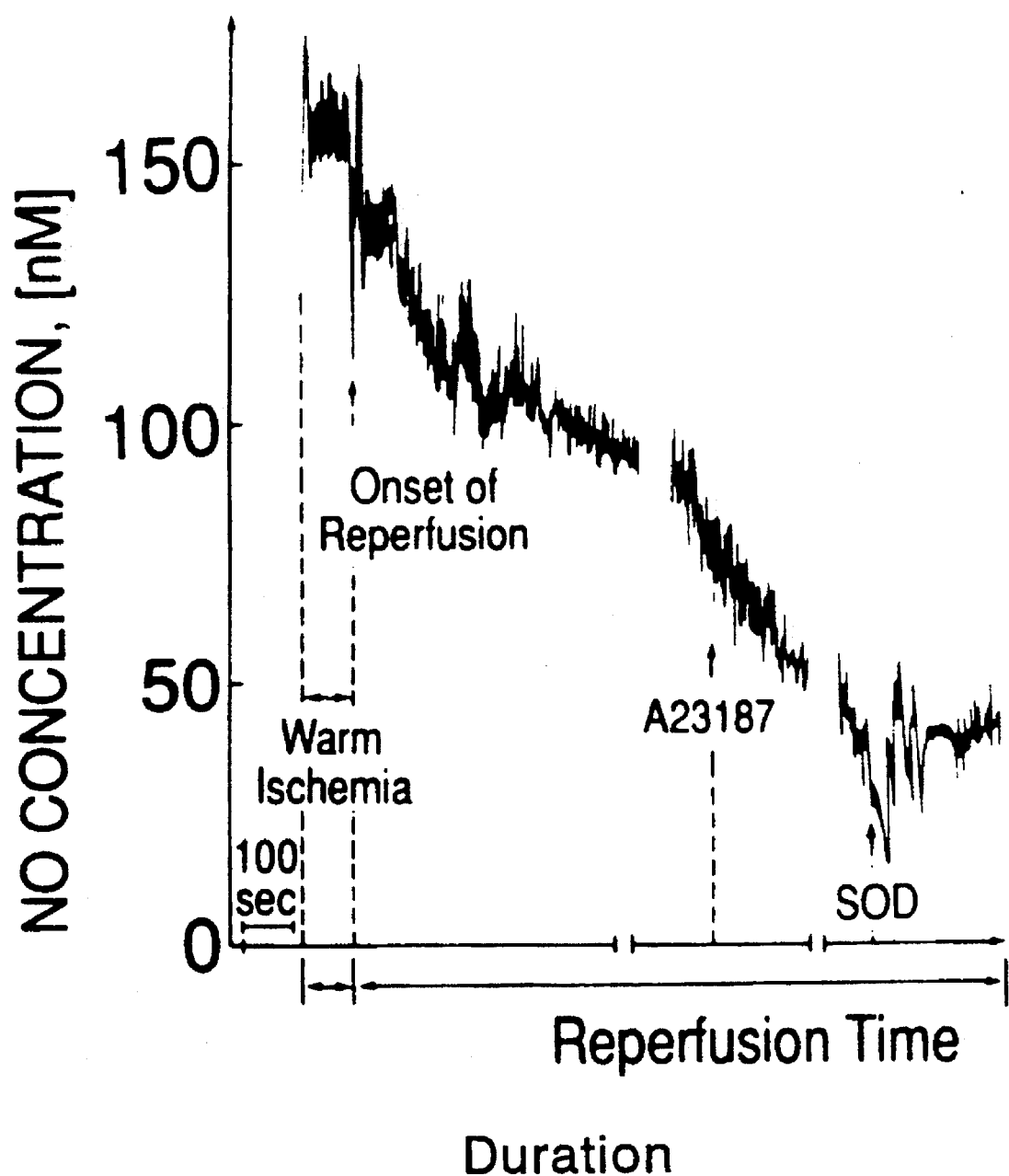
Figure 13D:
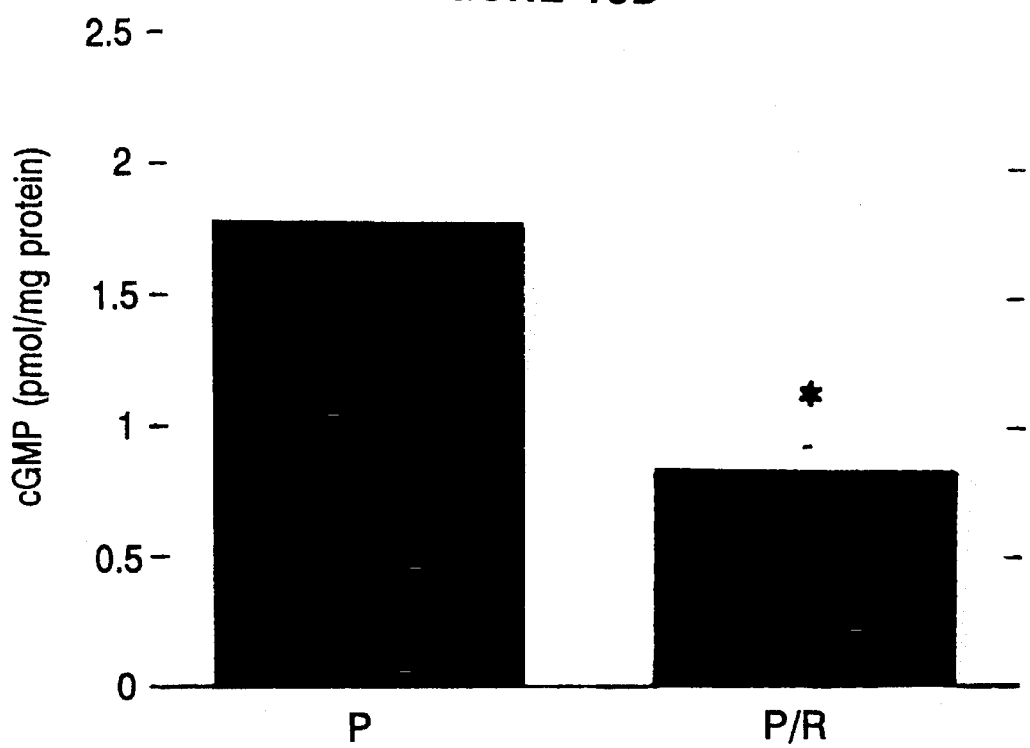
Figure 13E:
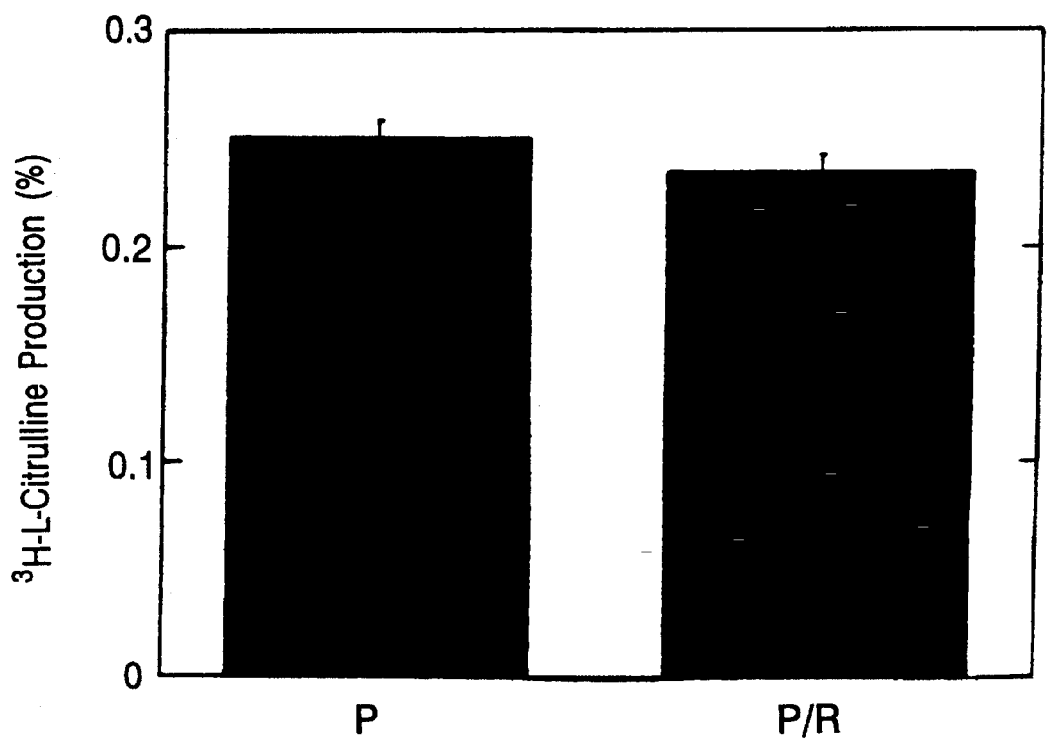
Figure 14A:
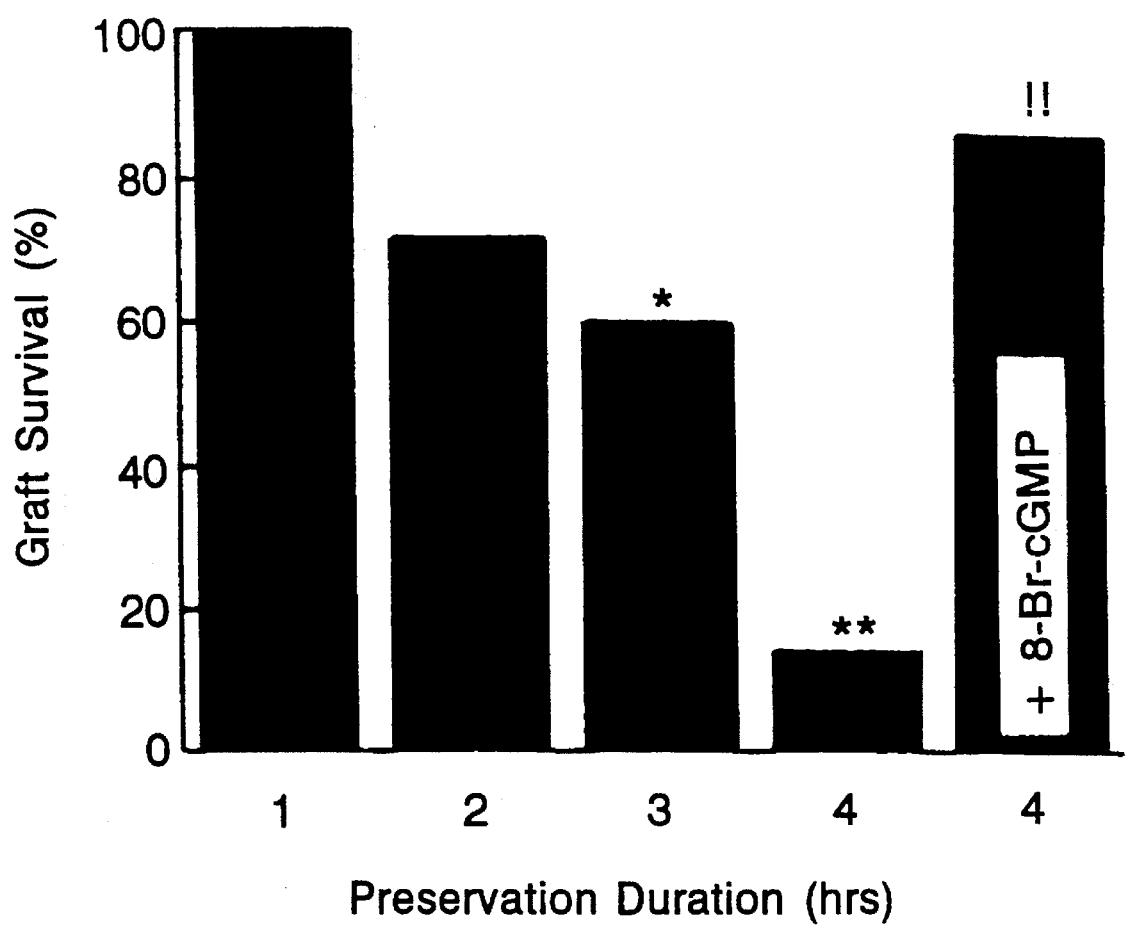
FIGS. 14A–B. A. Time-dependence of lung transplantation success following hypothermic preservation in LR, with effect of 8-Br-cGMP (0.5 mM) at 4 hours. Orthotopic rat lung transplants were performed and survival measured as described in the text. Mean percent survival is shown. (from left to right, n=5, 21, 5, 14, and 14 transplants, where * = $p<0.05$ and ** =p <0.01 vs 1 hr preservation, and ! ! = $p< 0.01$ vs 4 hr preservation). B. Representative hemodynamic tracing of a lung transplant following hypothermic preservation for 4 hrs in LR; or C. LR supplemented with 8-Br-cGMP (0.5 mM, right panel). PAP=mean pulmonary arterial pressure (mm Hg); PAF=pulmonary arterial flow (ml/min); PVR=pulmonary vascular resistance (Woods units/1000) and $pO_2$=arterial oxygenation (mm Hg). Time 0 corresponds with ligation of the native (right) pulmonary artery.
Figure 14B:
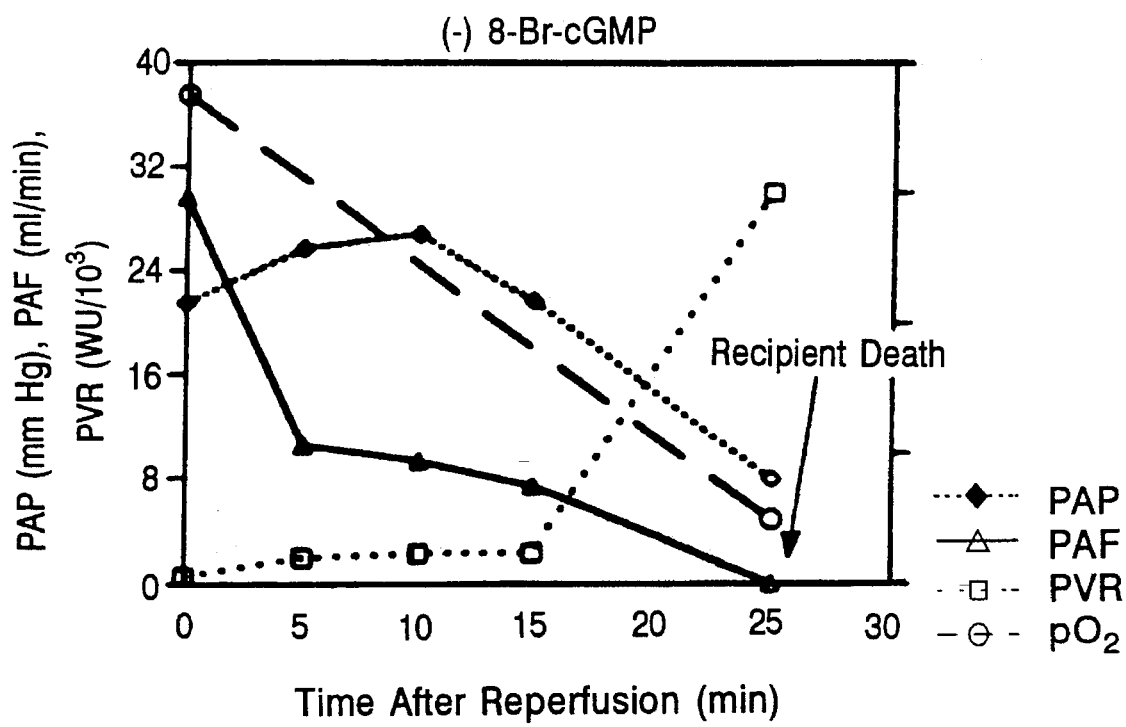
Figure 14C:
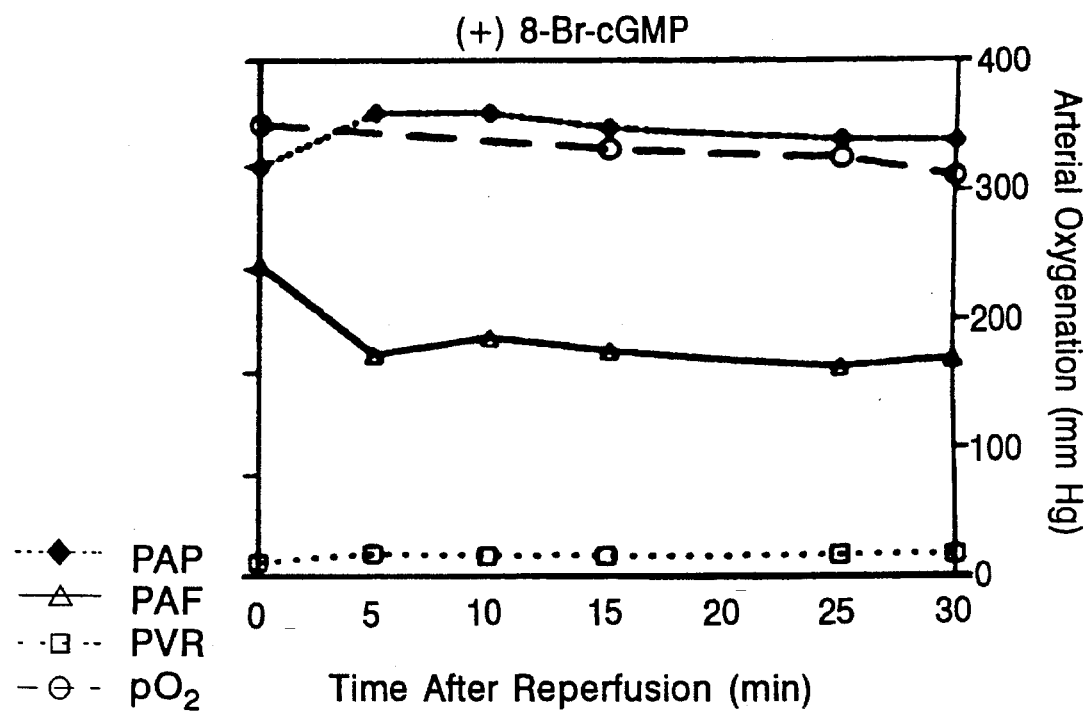
Figure 15A:
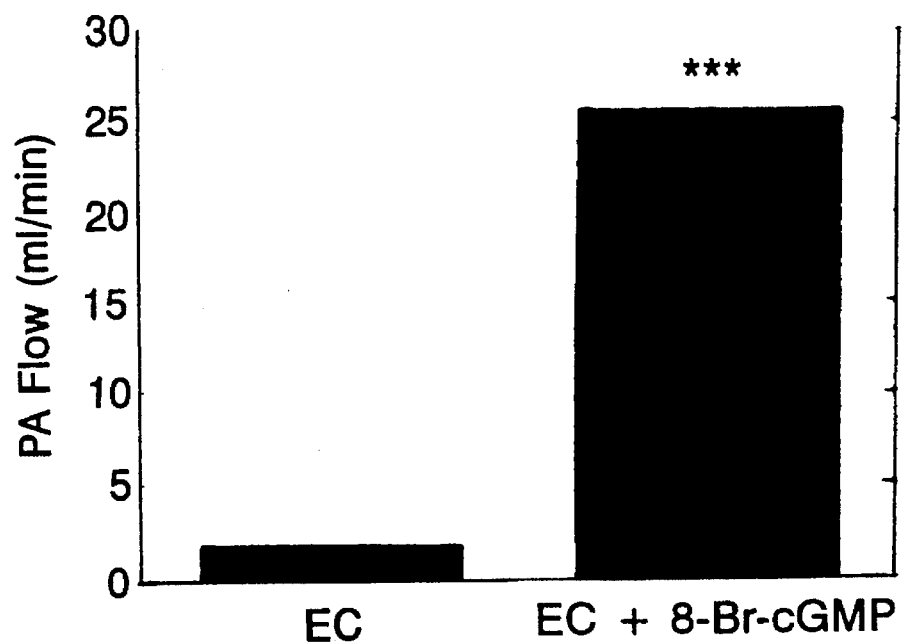
FIGS. 15A–E. Effect of 8-Br-cGMP on lung preservation in Eurocollins (EC) solution. All lung transplants were performed following 6 hours of hypothermic preservation, with measurements recorded 30 minutes following the onset of reperfusion. A. Pulmonary arterial flow, B. arterial oxygenation, and C. pulmonary vascular resistance are shown. Means ±SEM are shown. (n=6 for EC, n=5 for EC+8-Br-cGMP; *=p< 0.05, =p< 0.01, and *=p<0.001). 2. Dose response of 8-Br-cGMP, showing maximal ability to enhance lung preservation at (0.5 mM). E. Recipient survival at 30 minutes following reperfusion, demonstrating the importance of cGMP. Grafts were preserved in EC alone (leftmost bar, n=16), in the presence of the 8-Br-cGMP (0.5 mM, n=5), the cGMP-specific phosphodiesterase inhibitor M&B 22948 (2 mM, n=3), the combination of 8-Br-cGMP (0.5 mM) and the cGMP-dependent protein kinase inhibitor Rp-8-pCPT-cGMPS (5 mM, n=2), or with 8-bromo-guanosine5'monophosphate (noncyclic, 0.5 mM, n=2).
Figure 15B:
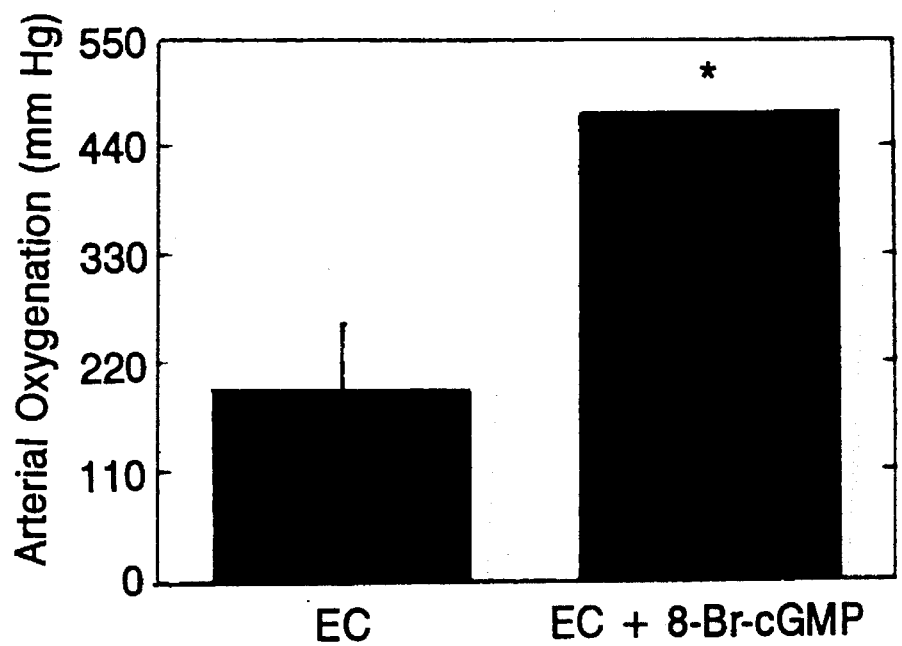
Figure 15C:
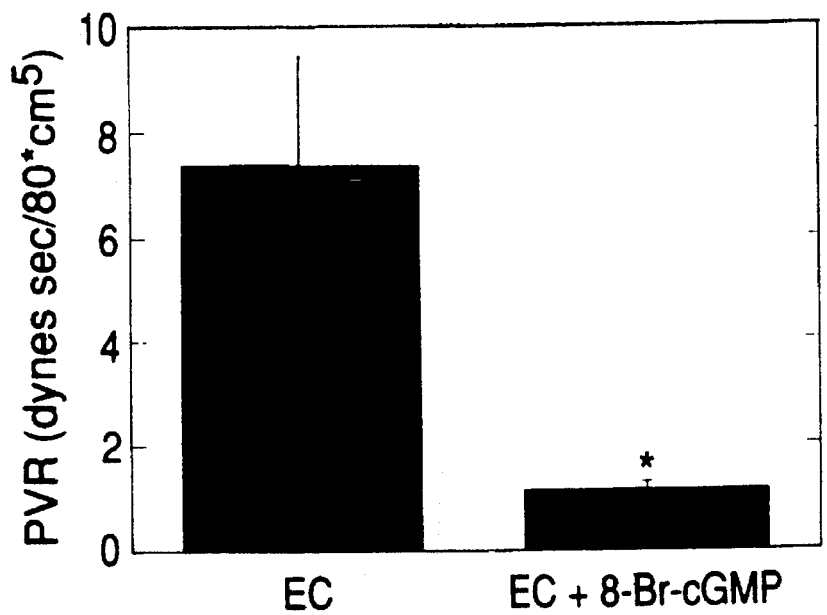
Figure 15D:
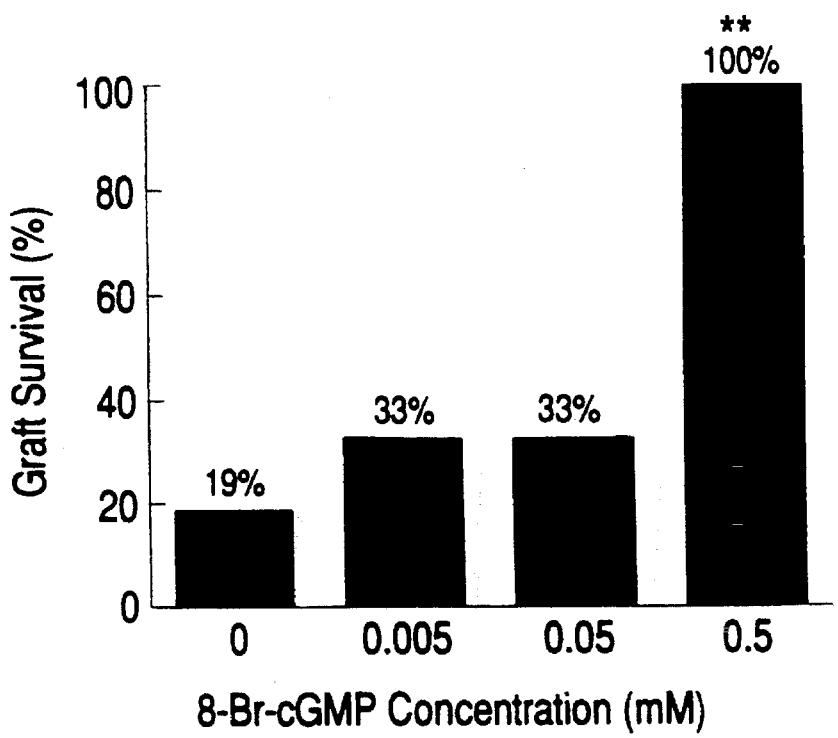
Figure 15E:
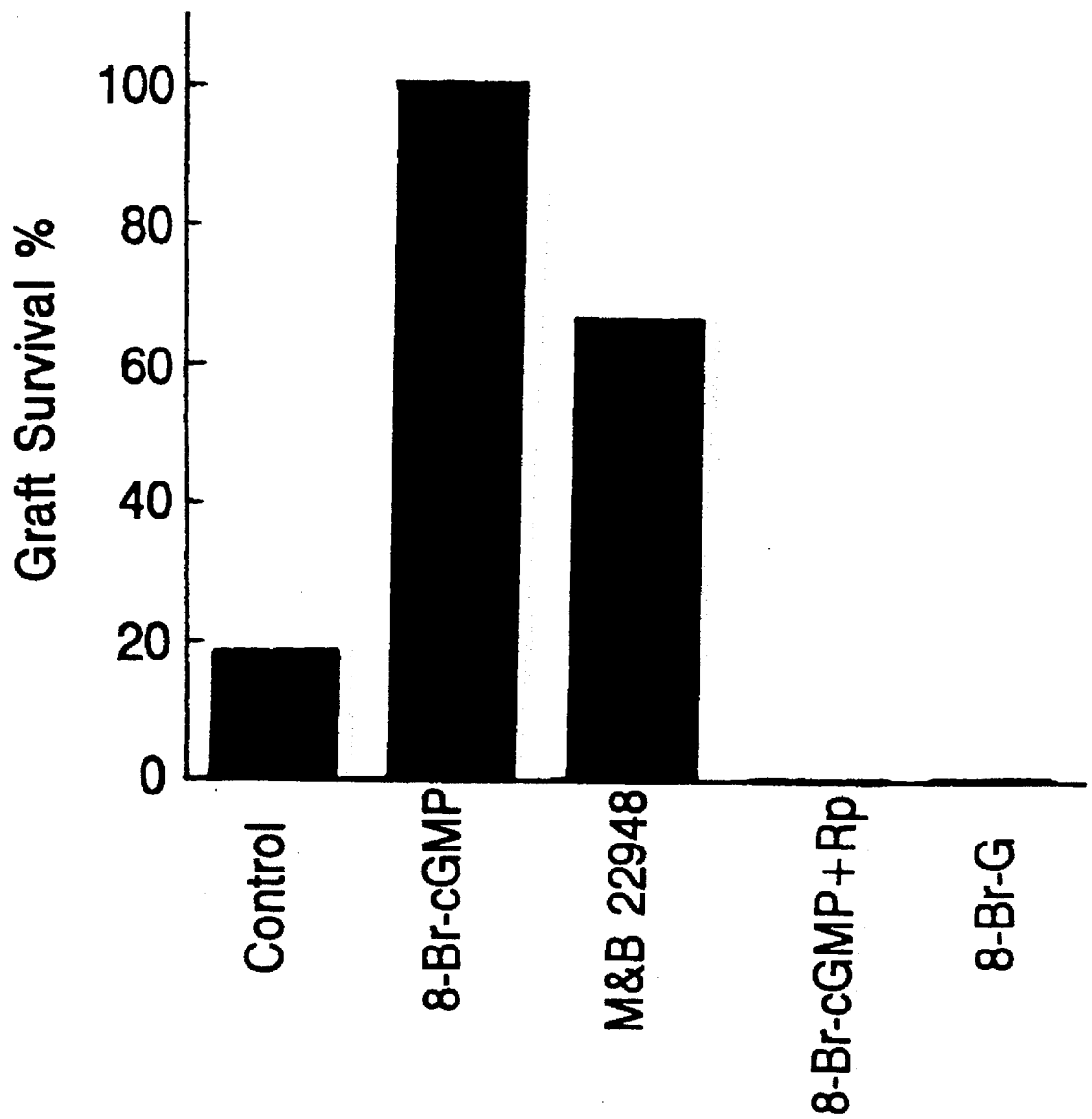
Figure 16A:
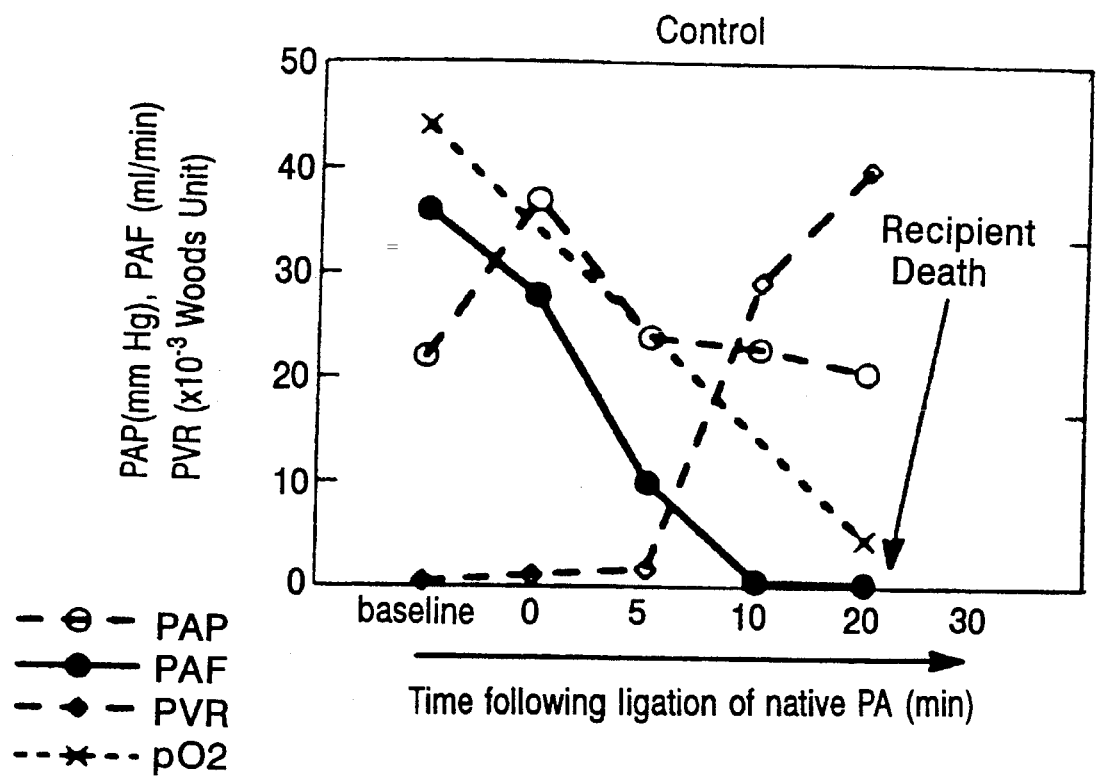
FIGS. 16A–B. Representative hemodynamic tracing of a lung transplant following hypothermic preservation for 6 hours in Euro-Collins solution (EC) alone (Control.
Figure 16B:
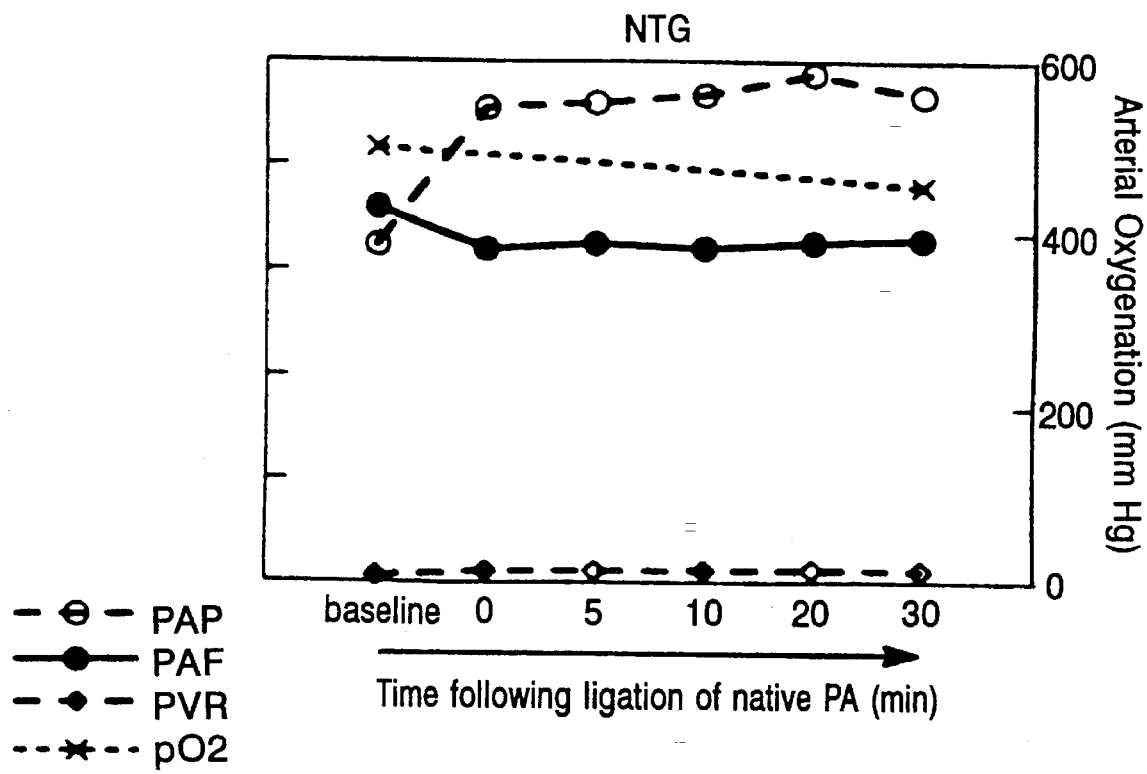
Figure 17A:
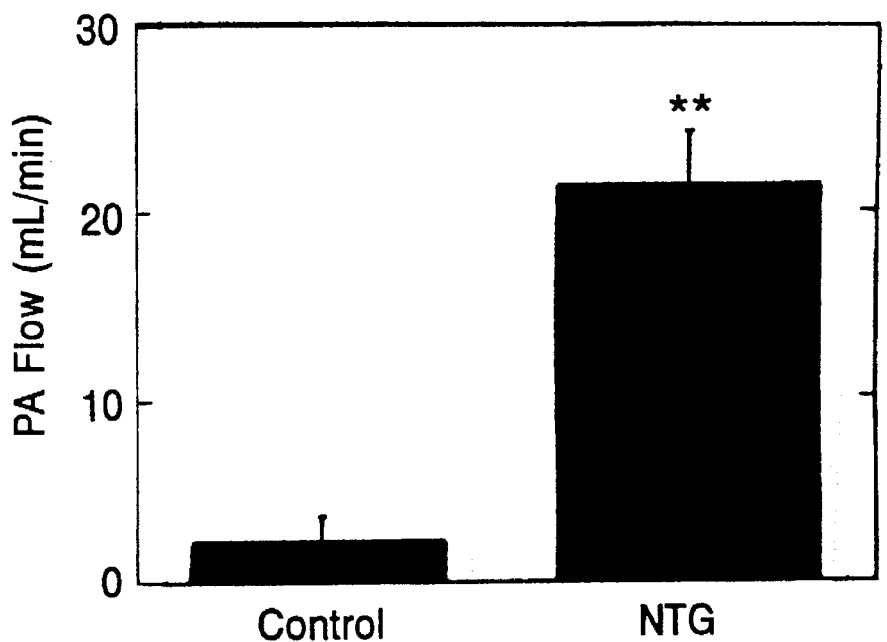
FIGS. 17A–C. Effects of NTG on lung preservation for transplantation. All lung transplants were performed following 6 hours of hypothermic preservation in Euro-Collins solution. Measurements were recorded at the final time at which recipient was alive or at 30 minutes following ligation of the native right pulmonary artery. A. Pulmonary arterial flow (mL/min) (n=6 for Control, n=5 for NTG), B. Pulmonary vascular resistance ($\times 10^{-3}$ Woods units) (n=6 for Control, n=5 for NTG), C. Arterial oxygenation (mm Hg) (n=10 for Control, n=5 for NTG) are shown. Means ± SEM are shown. *= p<0.05, and **=p<0.01.
Figure 17B:
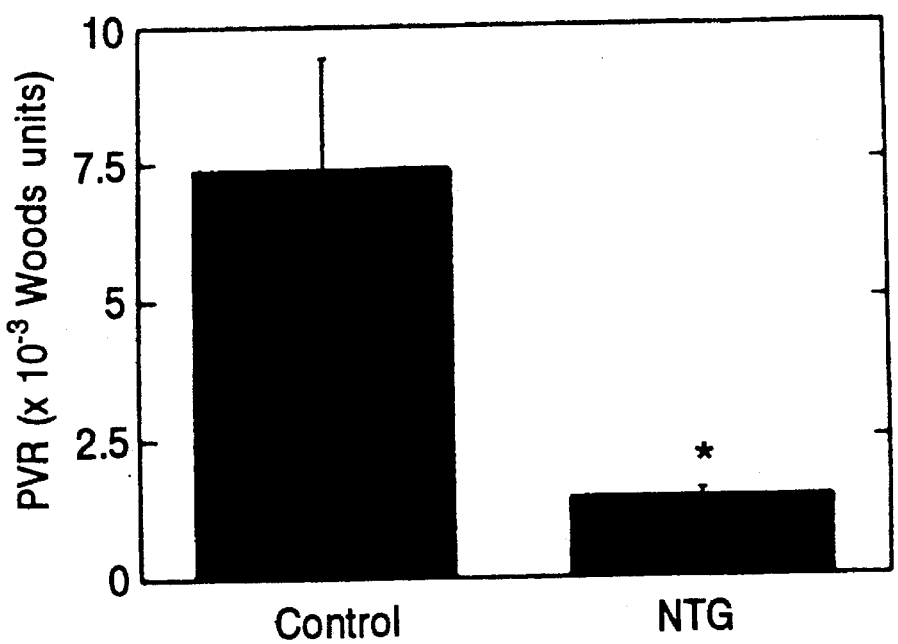
Figure 17C:
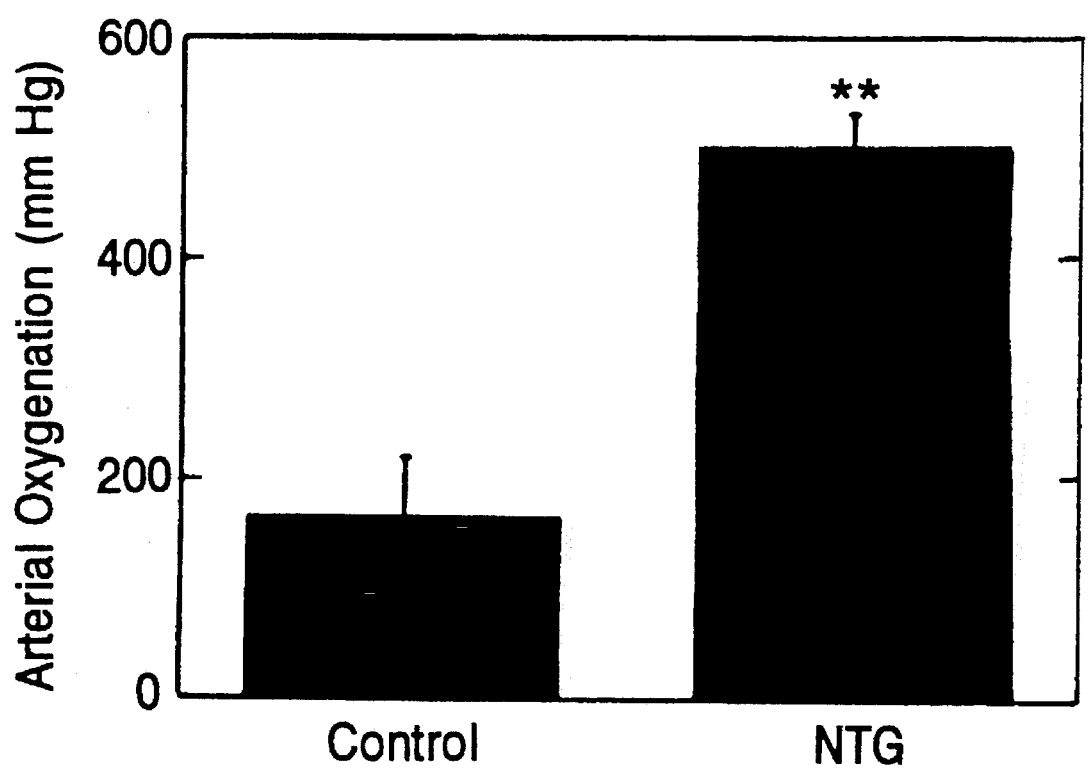
Figure 18:
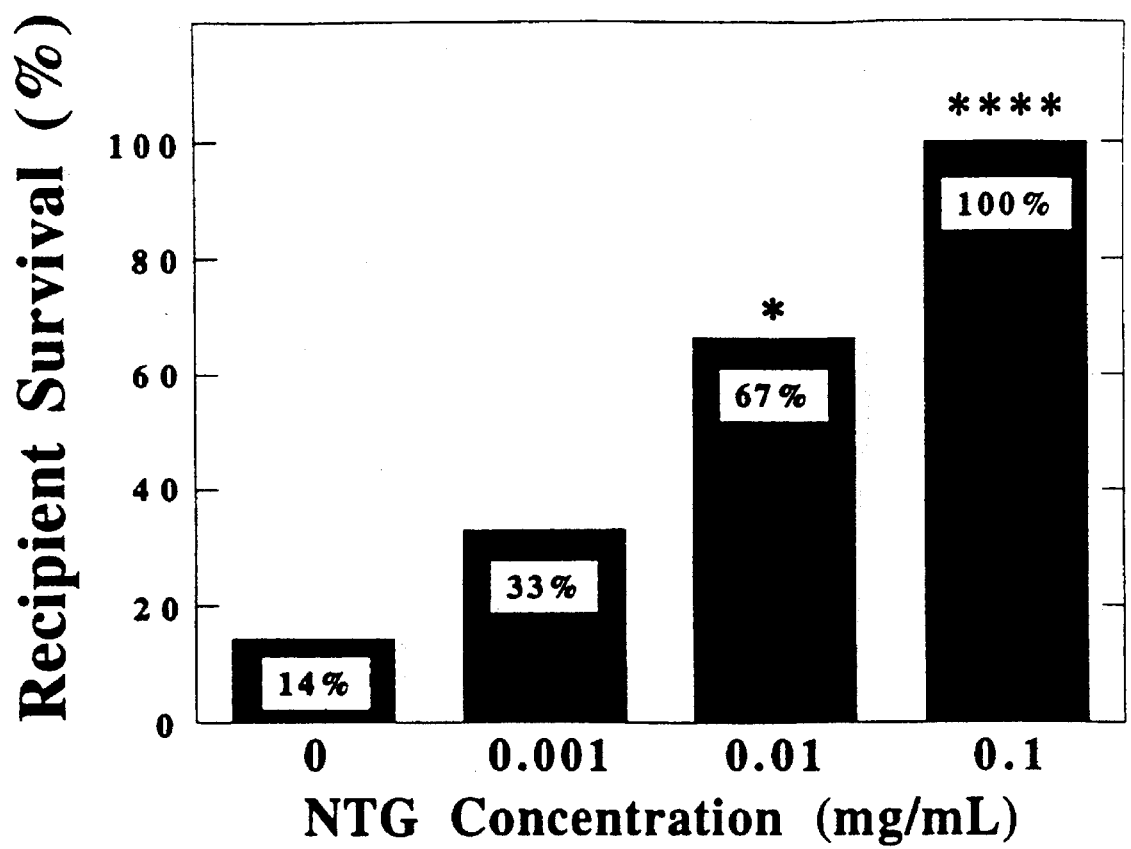
FIG. 18. Recipient survival at 30 minutes following ligation of the native right pulmonary artery. Dose response of NTG showed maximal ability to enhance lung preservation at 0.1 mg/mL. (n=21 0 mg/mL, n=3 for 0.001 mg/mL, n=3 for 0.01 mg/mL, n=7 for 0.1 mg/mL) *=p<0.05, and ****=p<0.001 vs 0 mg/mL.
Figure 19A:
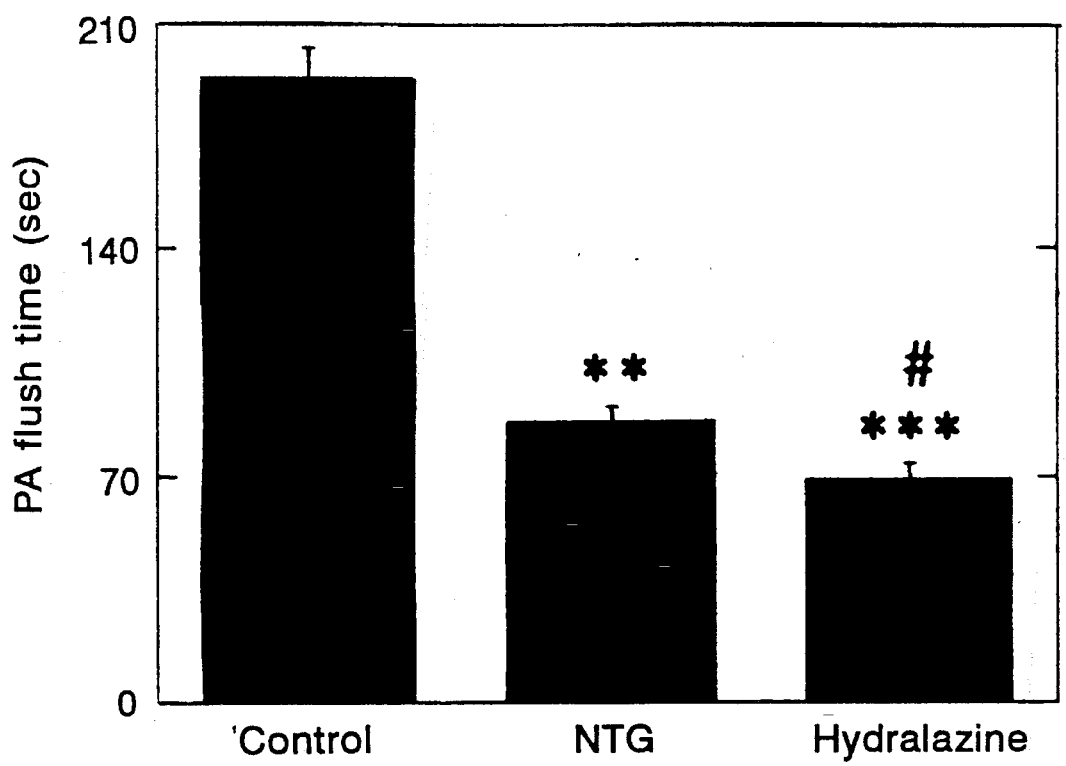
FIGS. 19A–B. Effects of vasodilators on pulmonary artery flushing time and recipient survival. A. Effect of preservation solution on pulmonary artery flushing time during harvest of the lung. (n=6 for Control [EC alone], n=5 for NTG [EC+NTG, 0.1 mg/mL], n=6 for Hydralazine [EC+Hydralazine, 0.02 μg/mL]) B. After flushing lungs with hypothermic preservation solutions as described, harvested lungs were preserved for 6 hours at 4° C. in preservation solution with the identical composition as that used during harvest. Recipient survival at 30 minutes following ligation of the native right PA. (n=21 for Control, n=7 for NTG, n=6 for Hydralazine) =p<0.01, *=p<0.005, ****=p<0.001 vs controls, #=p<0.05 vs NTG.
Figure 19B:
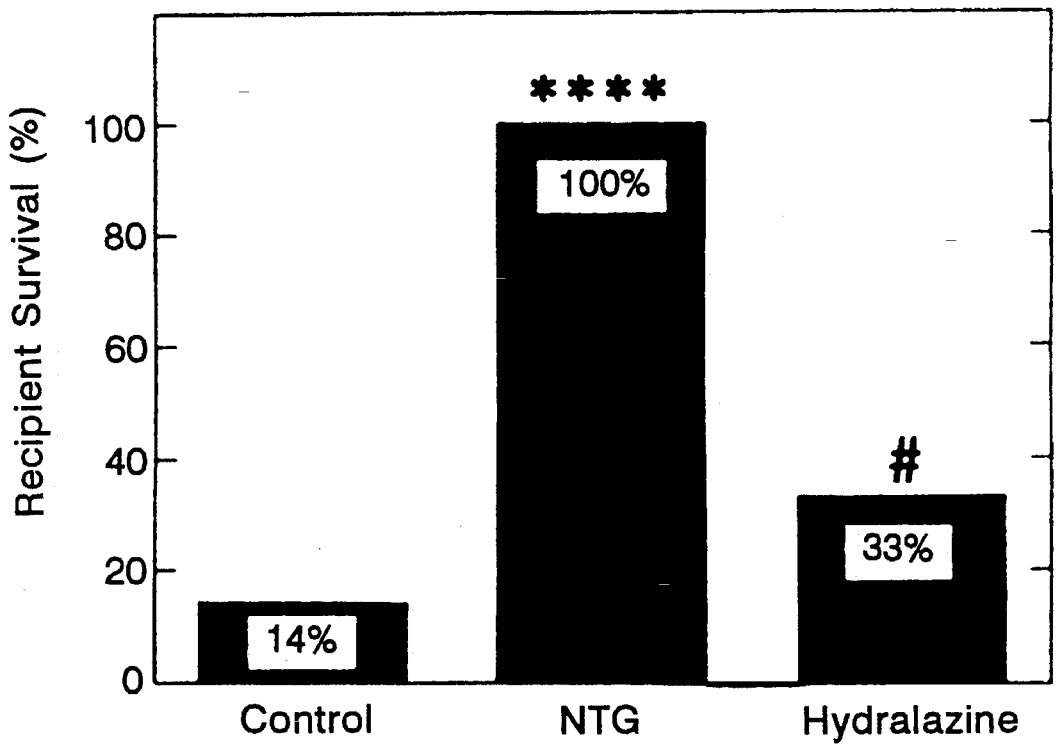
Figure 20A:
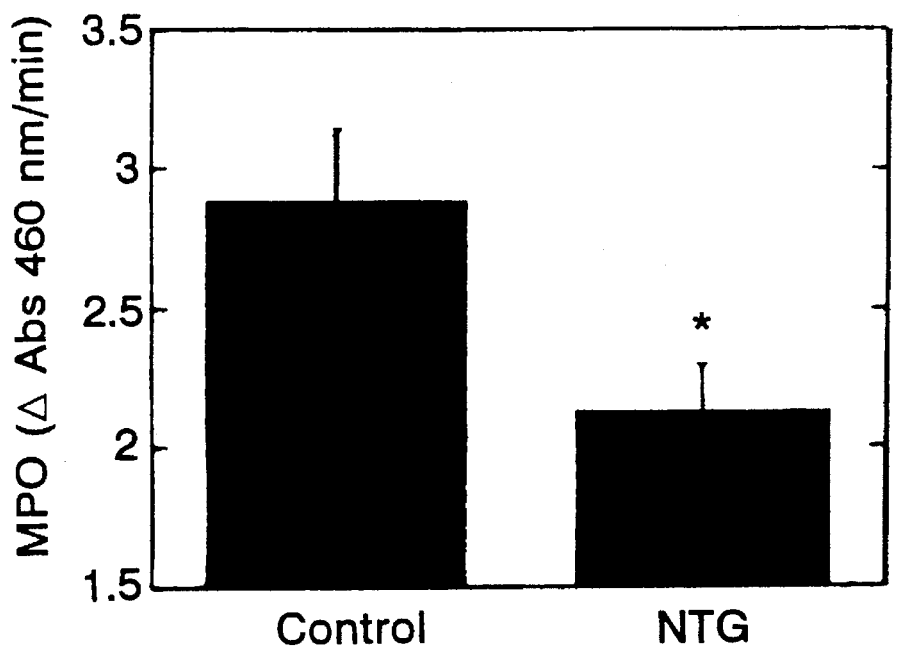
FIGS. 20A–C. Effects of NTG on graft neutrophil and platelet accumulation, and oxidant stress of graft tissue. A. Myeloperoxidase activity (MPO; ΔAbs 460 nm/min) (n=6 for Control, n=6 for NTG), B. $^{111}$Indium-labeled platelet accumulation, expressed as the ratio of graft radioactivity to blood radioactivity (n=6 for Control, n=6 for NTG), C. Content of thiobarbituric acid reactive substances (TBARs; nmol malondialdehyde/mg protein) (n=6 for Control, n=6 for NTG) are shown. Means±SEM are shown. *= p<0.05.
Figure 20B:
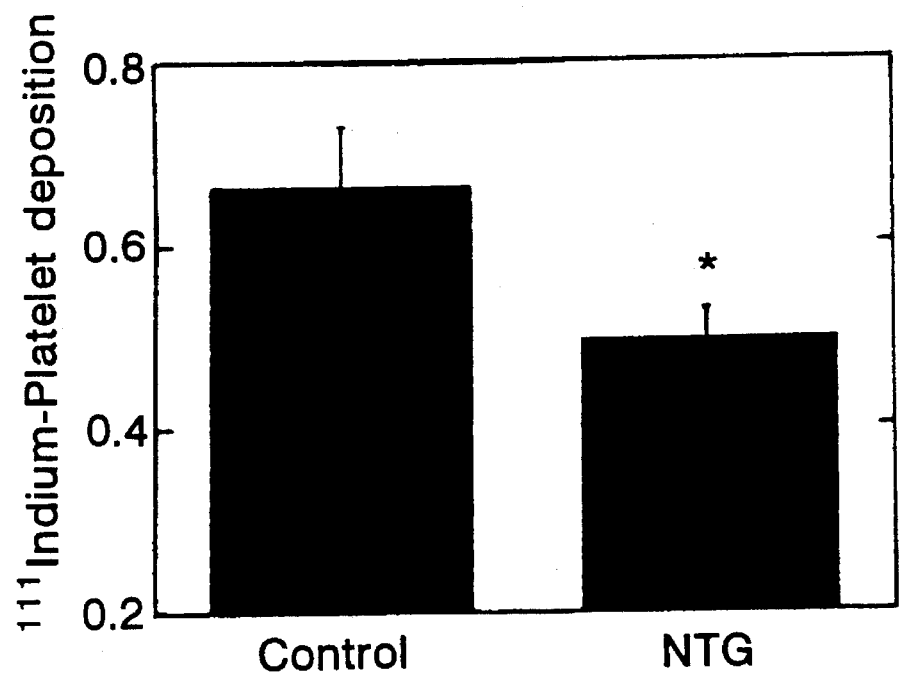
Figure 20C:
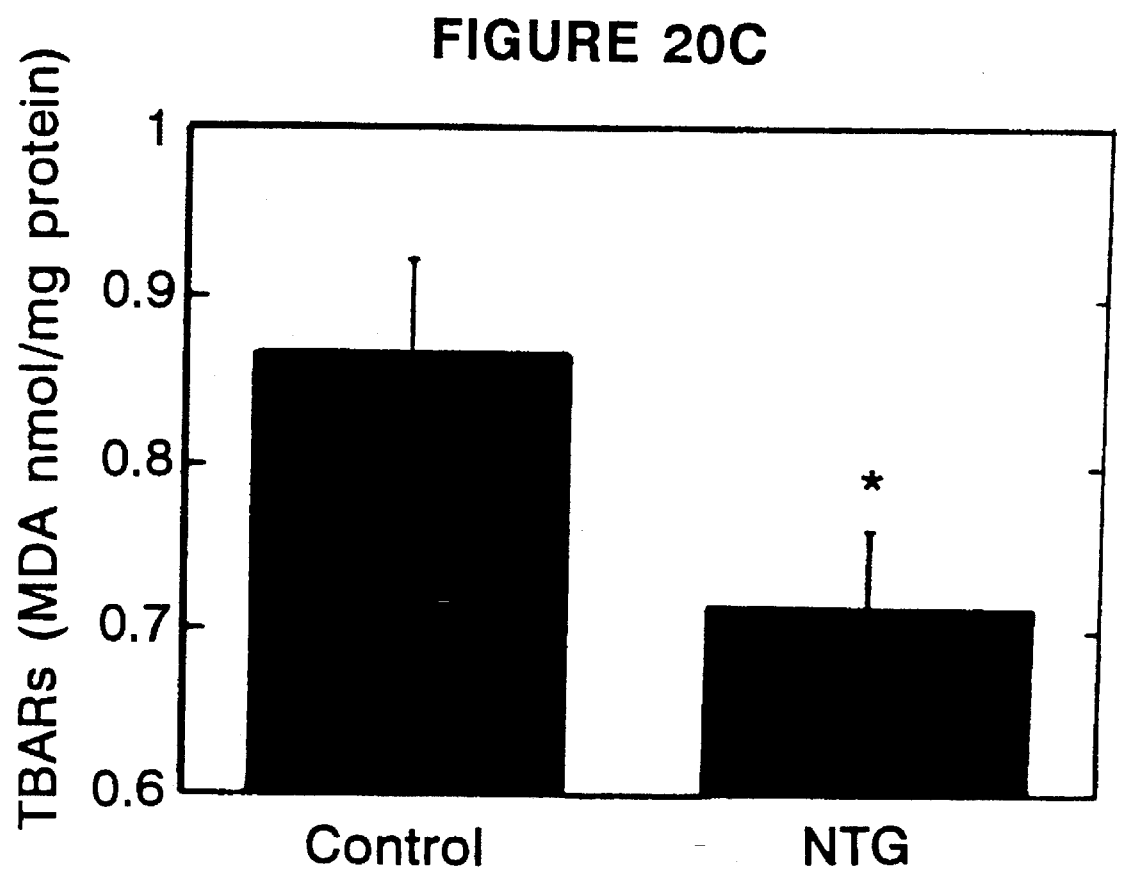

To further examine NO levels in preserved and transplanted lungs, continuous direct measurements of pulmonary NO were made before and after the onset of reperfusion using the porphyrinic microsensor in an amperometric mode and placed on the surface of the lung. (FIG. 1C) For these studies, lungs were preserved for 6 hours at 4° C. in LR and then transplanted. Continuous measurement of NO was made for several minutes prior to the reestablishment of blood flow, and recording was continued as the vascular cross-clamp was released to initiate reperfusion. NO levels were constant at 160±25 nM following preservation, but this level plummeted immediately after the onset of reperfusion, as predicted by the lung tissue studies described above (FIGS. 1 A–B). During continued reperfusion, addition of the calcium ionophore A23187 did not alter the decline in NO, whereas superoxide dismutase increased detectable NO levels (from ~25 to ~40 nM). Similar measurements performed in vivo on normal lung showed a local NO concentration of 660±100 nM, which increased 10% in the presence of SOD (to 720±110 nM). Taken together, these data indicate that during reperfusion, NO is present at reduced levels, suggesting that there might be reduced stimulation of guanylyl cyclase and lower cGMP levels in reperfused tissue. To determine if this was the case, cGMP levels were measured in lungs reperfused with oxygenated LR in order to measure pulmonary cGMP levels without the confounding influence of platelet-derived cGMP. These studies demonstrated lower cGMP content of preserved lung tissue following reperfusion (FIG. 1D), despite unaltered synthesis of NO (measured by the conversion of L-arginine to L-citrulline, FIG. 1E).

Because cGMP levels decline following reperfusion, it was investigated whether replenishing this intracellular second messenger would enhance graft vascular function and recipient survival following lung transplantation. Using an orthotopic rat lung transplant model in which the native lung is tied off, so that pulmonary hemodynamics and recipient survival depend entirely on the transplanted lung, the preservation solution (LR) was supplemented with a membrane-permeable cGMP analog (8-bromoguanosine 3',5' cyclic monophosphate, 8-Br-cGMP). In this model in which warm ischemic time was not varied, graft function was inversely related to the duration of hypothermic preservation, with 4 hours of hypothermic preservation representing the duration at which <15% of transplanted grafts survived [FIG. 2A]. Supplementation of LR with 8-Br-cGMP resulted in 86% survival following transplantation (p<0.01), even though the duration of preservation remained 4 hours. Following reperfusion, lungs which had been preserved for 4 hours in LR in the absence of cGMP supplementation demonstrated an immediate marked increase in pulmonary vascular resistance, and a decline in pulmonary artery flow and arterial oxygenation. These were invariably followed by a drop in PA pressure and rapid recipient death [FIG. 2B, left panel]. When 8-Br-cGMP was added to the preservation solution, all of these parameters were stabilized and the recipients survived [FIG. 2B, right panel].

To better understand the potential impact of these findings on clinical lung transplantation, experiments were performed using the standard solution for human lung preservation, modified Euro-Collins solution (EC)[3-6]. Lungs stored in EC, followed by reimplantation/reperfusion, showed hemodynamic responses similar to those stored in LR, except that the storage time after which grafts never regained function was displaced from 4 to 6 hours (data not shown). When EC was used as the base solution, supplemental 0.5 mM 8-Br-cGMP (1) increased pulmonary blood flow (from 2.2±1.4 to 26±2.3 ml/min, p=0.006; FIG. 3A); (2) increased arterial oxygenation (from 192±68 to 474±41 mm Hg, p=0.04; FIG. 3B); (3) decreased pulmonary vascular resistance (from 7.4±2.0 to 1.1±0.14 Woods units×$10^{-3}$, p=0.01; FIG. 3C); and (4) improved recipient survival (from 19% to 100%, p=0.006; FIG. 3D). These effects of 8-Br-cGMP were dose-dependent over a range of 0.005 to 0.5 mM, with maximal beneficial effects seen by 0.5 mM (FIG. 3D; improvement of oxygenation and graft blood flow were also dose dependent-data not shown). When the cGMP-specific (type V) phosphodiesterase inhibitor M&B 22948[36-38] was used, similar preservation enhancement was observed (FIG. 3E). To demonstrate that enhanced pulmonary preservation was the result of stimulation of the cGMP-dependent protein kinase rather than an effect mediated by purinergic receptors, the specific cGMP-dependent protein kinase antagonist Rp-8-pCPT-cGMPS[39] was shown to block the beneficial effects of 8-Br-cGMP, and 8-bromoguanosine 5'monophosphate was without effect (FIG. 3E).

Leukostasis is an important contributor to tissue damage in a range of ischemic states[40,41], leading us to assess the effect of 8-Br-cGMP on the presence of leukocytes in the lung grafts following 6 hours of preservation in EC followed by transplantation. In these experiments, neutrophil infiltration into reperfused grafts was quantified by measuring myeloperoxidase activity in tissue homogenates. Myeloperoxidase activity was significantly diminished in lung grafts stored in the presence (n=5) versus the absence (n=6) of 8-Br-cGMP (dAbs 460 nm/min was 1.75±0.13 vs 2.88±0.27, respectively, p=0.006).

Discussion

These studies demonstrate that NO availability is sharply diminished following preservation and reperfusion of a richly vascularized organ such as the lung, resulting in a fall in tissue cGMP levels and accompanying changes in vascular function. The fall in detectable NO occurs in the face of continued NO synthesis, indicating that accelerated destruction is likely to be the major mechanism accounting for the observed decline in NO. This possibility is supported by the increase in NO levels measured in preserved/reperfused lungs following the addition of superoxide dismutase, and is consistent with the observations of others that reactive oxygen intermediates are formed in abundance in the reperfused lungs[7-12]. However, superoxide dismutase did not completely restore NO to pre-reperfusion levels, which is not surprising for several reasons. There is likely to be a spectrum of reactive oxygen intermediates formed in the lungs by multiple oxidant generating systems within endothelial cells, resident alveolar macrophages, and recruited neutrophils. In addition, the reaction of NO with superoxide is rapid and thus may effectively compete with the dismutation of superoxide[42], and the large size of superoxide dismutase may restrict its accessibility to sites of superoxide formation. Because the porphyrinic microsensor (with a response time of about 1 millisecond) is capable of detecting only the unreacted portion of NO[30], this may explain why net NO levels do not fully return to pre-reperfusion levels following the addition of superoxide dismutase.

While the absolute values of NO measured both in vivo and ex vivo are considerably higher than the minimal NO concentrations which relax vascular smooth muscle (less than 15 nM)[31], NO concentrations in the present study were measured directly on the tissue surface. Because under normal physiologic conditions, NO produced at the endothelial surface is rapidly diluted and dissipated in blood and tissue, the highest concentrations exist directly at sites of NO production, such as endothelial cells, with lower concentrations in nearby effector cells (such as smooth muscle)[43]. As the surface concentration of NO is not affected by the volume of the static solution around the sensor, surrounding edema fluid in the current experiments should not affect these measurements. The observed decline in NO levels in vivo following reperfusion cannot be explained based on an increase in temperature of the microsensor, for several reasons; First, during the period of warm ischemia during which the preserved lung is sewn into place, the donor lung resides within the recipient thorax and achieves a temperature nearly equal to that of the recipient prior to the onset of reperfusion (data not shown). Secondly, the diffusion controlled electrochemical process on which the porphyrinic sensor is based[44] has a predicted temperature coefficient (1.78% increase in current per 1° C. increment in temperature) which is similar that of the porphyrinic microsensor (1.82%). Therefore, an increase in temperature of the microsensor would be expected to result in an increase in NO levels, whereas a decrease in NO levels was observed following reperfusion. Finally, NO levels were augmented during the addition of SOD at a time well beyond initial reperfusion.

The effect of organ preservation and reimplantation on NO availability observed in these studies closely parallels the picture which emerges from other models of ischemia and reperfusion, in which endothelium-derived relaxation factor (EDRF) bioactivity declines early during the reperfusion period, due to the production of reactive oxygen intermediates[28,45,46]. Because ischemic/reperfused lungs rapidly generate oxygen free-radicals, which can quench NO and form toxic intermediates such as peroxynitrite[42,47,48], it was decided to supplement the NO/cGMP pathway distal to NO, at the level of cGMP. While there are multiple mechanisms whereby cGMP levels may be elevated[49], such as by stimulation of membrane-associated guanylyl cyclase by atrial natriuretic peptide[50], enterotoxin[50], or by calcium/ recoverin in retinal rods[52], stimulation of soluble guanylate cyclase by NO appears to be the major stimulator of cGMP production in the lungs, based on experiments in which an NO synthesis inhibitor completely abrogated the pulmonary vasorelaxant effects of selective cGMP phosphodiesterase inhibition[38].

Supplementing cGMP levels by administering 8-Br-cGMP has significant beneficial effects on graft vascular function, gas exchange, and recipient survival when added to the storage solution in the orthotopic lung transplant model. These beneficial effects appear to be mediated by the cGMP moiety, as; (1) they are mimicked by the cGMP phosphodiesterase inhibitor M&B 22948, which raises endogenous levels of cGMP by preventing its degradations[36]; (2) 8-bromoguanosine 5'monophosphate was without effect, and; (3) the cGMP-dependent protein kinase inhibitor Rp- 8-pCPCT-cGMPS[39] abrogated the beneficial effects of 8-Br-cGMP. This also suggests that a physiologically important target of 8-Br-cGMP in this setting is protein kinase G. These data underscore the role of NO/cGMP in maintaining normal pulmonary vascular homeostasis, and also suggest that peroxynitrite formed during reperfusion by the combination of NO with superoxide[42,47] is not clinically significant, as this reaction would not be altered by 8-Br-cGMP supplementation.

It is important to note that the actions of 8-Br-cGMP in the setting of lung preservation/transplantation are not limited to vasodilation. Direct-acting vasodilators such as hydralazine[53] have not proven beneficial in lung preservation[54], suggesting that vasodilation alone is insufficient to enhance preservation. While other agents which augment local adenosine release from ischemic myocardium also vasodilate and reduce neutrophil infiltration[55], the actions of 8-Br-cGMP on lung preservation cannot be ascribed to similar activation of purinergic receptors, as 8-Br-guanosine was without effect, and a specific cGMP phosphodiesterase inhibitor which increases intracellular cGMP levels did mimic the beneficial effects 8-Br-cGMP. In addition to its ability to decrease pulmonary vascular resistance and enhance graft blood flow, 8-Br-cGMP diminished leukostasis and improved gas exchange as well. This is consistent with previous studies indicating that NO can block leukocyte/endothelial interactions[19] and promote maintenance of vascular barrier functions[21], and emphasizes the pluripotent benefits of augmenting an endogenous second messenger pathway that appears to be suppressed following ischemia and reperfusion. The initial inhibition of neutrophil recruitment into the reperfused graft may not only improve parenchymal function of a reperfused tissue, but may result in greater local concentrations of NO. Increased local NO concentrations may further reduce leukocyte adhesion via NO's interactions with superoxide[56], thereby magnifying the initial beneficial effects of cGMP supplementation. These observations are likely to be relevant to the pathophysiology of ischemic tissue injury, since neutrophil plugging has been implicated as an important cause of the no-reflow phenomenon following ischemia and reperfusion[57,58], and mechanical depletion of neutrophils from the perfusate improves the function of isolated/reperfused lungs[59,60].

Like cGMP, cAMP is a vasodilator[61] which can interfere with neutrophil adhesion to endothelium[62]. Because of the intricate interrelationships between cAMP and cGMP metabolism (such as cGMP-stimulatable and cGMP-inhibitable phosphodiesterase activities)[63], it is impossible to completely exclude a role for elevation of intracellular cAMP in the enhancement of pulmonary preservation observed in these studies. The importance of endogenous cGMP in this setting, however, comes from several lines of evidence. In these studies, cGMP levels were reduced in reperfused lungs. The analog of cGMP that was used in this study (8-Br-cGMP) is 500 times more potent at stimulating the cGMP dependent protein kinase compared with the cAMP-dependent protein kinase[64,65]. In addition, 8-Br-cGMP does not interact with the allosteric binding sites on the cGMP-regulated phosphodiesterases[66], and hence does not effect cAMP hydrolysis in intact cell studies. Because the cGMP-specific (type V) phosphodiesterase inhibitor M&B 22948 augments the pulmonary vasodilating effects of NO(cGMP)-dependent vasodilators, but not those of a cAMP-dependent vasodilator such as isoproterenol[38], this suggests that its beneficial vascular effects in this study are likely to have been cGMP-mediated. Finally, the Rp-8-pCPT-cGMPS compound that blocked preservation enhancement in this study is relatively specific for the cGMP-dependent protein kinase ($K_i$ 0.5 µM, vs $K_i$ 8.3 µM for the cAMP-dependent protein kinase, Dr. H-G Ginesier, personal communication)[39], suggesting that its ability to block the effects of 8-Br-cGMP on lung preservation was not due to blocking cAMP-dependent protein kinase. Our results with 8-Br-cGMP are consistent with previous studies demonstrating that acidified sodium nitrite, nitroglycerin, and other agents which elevate intracellular cGMP blunt myocardial injury and neutrophil accumulation during reperfusion[67-69]. The potential applicability of these findings to clinical transplantation is suggested by the ability of 8-Br-cGMP to enhance lung preservation even in the currently accepted clinical standard lung preservation solution, modified Eurocollins. These studies suggest that augmentation of the NO pathway at the level of cGMP will provide a novel pharmacological approach to normalize vascular function in the critical early stages following reperfusion.

REFERENCES FOR FOURTH SERIES OF EXPERIMENTS

1. Belzer, F., and Southard, J. (1988) *Transplantation* 45, 673–676.
2. Wang, L-S., Yoshikawa, K., Miyoshi, S., Nakamoto, K., Hsieh, C-M., Yamazaki, F., Cordoso, P., Schaefers, H-J., Brito, J., Keshavjee, S., Patterson, A., and Cooper, J. (1989) *J. Thorac. Cardiovasc. Surg.* 98, 333–342.
3. Egan, T., Kaiser, L., and Cooper, J. (1984) *Curr. Probl. Surg.* 88, 993–999.
4. Trulock, E. (1992) *Annu. Rev. Med.* 43, 1–8.
5. Egan, T. (1992) *Seminars in Thor. and Cardiovasc. Surg.* 4, 83–89.
6. Novick, R., Menkis, A., and McKenzie, F. (1992) *J. Heart Lung Transplant.* 11, 377–392.
7. Hajjar, G., Toledo-Pereyra, and MacKenzie, G. (1987) *Transpl. Proc.* XIX, 1342–1344.
8. Lambert, C., Egan, T., Detterbeck, F., Keagy, B. and Wilcox, B. (1991) *Ann. Thorac. Surg.* 51, 924–930.
9. Paull, D., Keagy, B., Entwistle, T., and Willcox, B. (1988) *Curr. Surg.* 45, 292–294.
10. Lambert, C. and Egan, T. (1992) *Transplantation* 54, 205–209.
11. Conte, J,., Katz, N., Foegh, M., Wallace, R., and Ramwell, P. (1991) *J. Thorac. Cardiovasc. Surg.* 202, 1024–1029.
12. Kirk, A. J. B., Colquhoun, I. W., and Dark., J. H. (1993) *Ann. Thorac. Surg.* 56:990–1000.
13. Furchgott, R. F. and Zawadzki, J. V. (1980) *Nature* (London) 288, 373–376.
14. Palmer, R., Ferrige, A., and Moncada, S. (1987) *Nature (London)* 327, 524 –536.
15. Ignarro, L., Buga, G., Wood K., Byrns, R., Chaudhuri, G. (1987) *Proc. Natl. Acad. Sci* USA 84, 9265–9269.
16. Lowenstein, C., and Snyder, S. (1992) *Cell* 70, 705–707.
17. Nathan, C. (1990) *FASEB J.* 6, 3051–3064. 18. Ignarro, L., Ross, G. and Tillisch, J. (1991) *West J. Med.* 154, 51–62.
19. Kubes, P., Suzuki M. and Granger, D. (1991) *Proc. Natl. Acad. Sci.* USA 88, 4651–4655.
20. Radomski, M., Palmer, R., and Moncada, S. (1987) *Lancet* ii, 1057–1058.
21. Kubes, P. and Granger, D. (1992) *Am. J. Physiol.* 262, H611–615.
22. Meyer, J., Lentz, C. W., Herndon, D. N., Nelson, S., Traber, L. D., and Traber, D. L. (1993) *Anesth. Analg.* 77(6):1215-21.
23. Alving, K., Fornhem, C., and Lundberg, J. M. (1993) *Br. J. Pharmacol.* 110(2) 739–746.
24. Shaul, P. W., Farrar, M. A., Magness, R. R. (1993) *Am. J. Physiol.* 265 (4 pt 2): H1056–1063.
25. McMahon, T. J., Ignarro, L. J., and Kadowitz, P. J. (1993) *J. Appl. Physiol.* 74(4):1704–1711.
26. Sprague, R. S., Thiemermann, C., and Vane, J. R. (1992) *Proc. Natl. Acad. Sci.* USA 89(18):8711–8715.
27. Barer G., Emery, C., Stewart, A., Bee, D., and Howard, P. (1993) *J. Physiol.* (Lond) 463:1–16.
28. Lefer, A. M., Tsao, P. S., Lefer, D. J., & Ma, X-L. (1991) *FASEB J.* 5, 2029–2034.
29. Mizuta, T., Kawaguchi, A., Nakahara, K., and Kawashima, Y. (1989) *J. Thorac. Cardiovasc. Surg.* 97(4), 578–581.
30. Malinski, T. and Taha, Z. (1992) *Nature* (London) 358, 676–678.
31. Furchgott, R. F. and Jia, L. (1993) *J. Pharmacol. and Exp. Therap.* 267(1):371–378.
32. Goldblum, S., Wu, K. and Jay, M. (1985) *J. Appl. Physiol.* 59, 1978–1985.
33. Ogawa, S., Koga, S., Kuwabara, K., Morrow, B., Morris, S., Bilezikian, J., Silverstein, S., and Stern, D. (1992) *Am. J. Physiol.* 262:C546-554.
34. Lowry, O., Rosebrough, N., Farr, A. and Randall, R. (1951) *J. Biol. Chem.* 193, 265–275.
35. Stuehr, D., Cho, H., Kwon, N., Weise, M. and Nathan, C. (1991) *Proc. Natl. Acad. Sci.* USA 88, 7773–7777.
36. Harris, A. L., Lemp, B. M., Bentley, R. G., Perrone, M. H., Hamel, L. T., and Silver, P. J. (1989) *J. Pharmacol. and Exp. Therapeutics* 249, 394–400.
37. Merkel, L. A., Rivera, L. M., Perrone, M. H., and Lappe, R. W. (1992) *Eur. J. Pharmacol.* 216, 29–35.
38. Braner, D. A. V., Fineman, J. R., Chang, R., and Soifer, S. J. (1993) *Am. J. Physiol.* 264 (Heart Circ. Physiol. 33): H252–H258.
39. Butt, E., Van Bemmelen, M., Fischer, L., and Walter, U. (1990). *FEBS Lett* 263, 47–50.
40. Adkins, W. and Taylor, A. (1990) *J. Appl. Physiol.* 69, 2012–2018.
41. Granger, D. (1988) *Am. J. Physiol.* 255, H1269–H1275.
42. Hogg, N., Darley-Usmar, V. M., Wilson, M. T., and Moncada, S. (1992) *Biochem. J.* 281, 419–424.
43. Malinski, T., Taha, Z., Patton, S., Kapturczak, M., and Tomboulina, P. (1993) *Biochem. Biophys. Res. Comm.* 193(3):1076–1082.
44. Kissinger, P. T. and Heinman, W. R. (1984) in *Laboratory Techniques in Electroanalytical Chemistry*, Marcel-Deker, NY, pp. 10–49.
45. Zweier, J., Kuppusamy, P. and Lutty. G. (1988) *Proc. Natl. Acad. Sci.* USA 85, 4046–4050.
46. Babbs, C., Cregor, M., Turek, J. and Badylak, S. (1991) *Am. J. Path.* 139, 1069–1080.
47. Beckman, J. S., Beckman, T. W., Chen, J., Marshall, P. A., and Freeman, B. A. (1990) *Proc. Natl. Acad. Sci.* USA 87, 1620–1624.
48. Matheis, G., Sherman, M., Buckberg, G., Haybron, D., Young, H. and Ignarro, L. (1992) *Am. J. Physiol.* 262, H616–H620.
49. Bentley, J. K. and J. A. Beavo (1992), *Curr. Opin. Cell Bio.* 4:233–240.
50. Chinkers, M., Garbers, D. L., Chang, M. S., Lowe, D. G., Chin, H. M., Goeddel, D. V., and Schulz, S. (1989) *Nature* 338:78–83.
51. Schulz, S., Green, C. K., Yuen, P. S., and Garbers, D. L. (1990) *Cell* 63:941–948.
52. Dizhoor, A. M., Ray S., Kumar, S., Nilemi, G., Spencer, M., Brolley, D., Walsh, K. A., Philipov, P. P., Hurley, J. B., and Stryer, L. (1991) *Science* 251:915–918.
53. Ebeigbe, A. B. and Aloamaka, C. P. (1985) *Cardiovasc. Res.* 19:400–405.
54. Hachida, M. and Morton, D. L. (1988) *J. Thorac. Cardiovasc. Surg.* 95:178–183.
55. Gruber, H. E., Hoffer, M. E., McAllister, D. R., Laikind, P. K., Lane, T. A., Schmid-Schoenbein, G. W., and Engler, R. L. (1989) *Circulation* 80:1400–1411.
56. Gaboury, J., Woodman, R. C., Granger, D. N., Reinhardt P., and Kubes, P. (1993) *Am. J. Physiol.* 265 (Heart Circ. Physiol. 34) H862 –H867.

57. Kloner, R. (1989) *J. Am. Coll. Cardiol.* 14, 1814–1815.
58. Jerome, S. N., Smith, C. W., and Korthuis, R. J. (1993) *Am. J. Physiol.* 264, H479–H483.
59. Hall, T., Breda, M., Baumgartner, W., Borkon, M., Brawn, J., Hutchins, G. and Reitz, B. (1987) *Current Surg.* 44, 137–139.
60. Pillai, R., Bando, K., Schueler, S., Zebly, M., Reitz, B., and Baumgartner, W. (1990) *Ann. Thorac. Surg.* 50, 211–214.
61. Haynes, J., Robinson, J., Saunders, L., Taylor, A., and Strada, S. (1992) *Am. J. Physiol.* 262:H511–516.
62. Boxer, L., Allen, J., Baehner, R., and Amick, V. (1980) *J. Clin. Invest.* 66: 268–274.
63. Thompson, W. (1991) *Pharmacol. Ther.* 51: 13–33.
64. Francis, S. H., Noblett, B. D., Todd, B. W., Wells, J. N., and Corbin, J. D. (1988) *Mol. Pharmacol.* 34:505–517.
65. Corbin, J., Ogreid, D., Miller, J., Suva, R., Jastorff, B., and Doskeland, S. (1986) *J. Biol. Chem.* 261:1208–1214, 1986.
66. Thomas, M. K., Francis, S. H., Beebe, S. J., Gettys, T. W., and Corbin, J. D. (1992) in *Adv. in Second Messenger and Phosphoprot. Res.* (Strada, S. J. and Hidaka, H., eds) 25:45–53, Raven Press, New York.
67. Nakanishi, K., Vinten-Johansen, J., Lefer, D., Zhao, Z., Fowler, W., McGee, D. S., and Johnston, W. (1992). *Am. J. Physiol.* 263, H1650–1658.
68. Johnson, G., Tsao, P., Mulloy, D., and Lefer, A. (1990) *J. Pharm. and Exp. Therapeutics* 252 (1), 35–41.
69. Lefer, D. J., Nakanishi, K., Johnston, W. E., and Vinten-Johansen, J. (1993) *Circulation* 88(1), 2337–2350.

FIFTH SERIES OF EXPERIMENTS: VASCULAR HOMEOSTASIS IS ENHANCED IN ORTHOTOPICALLY TRANSPLANTED RAT LUNG GRAFTS BY SUPPLEMENTING EURO-COLLINS PRESERVATION SOLUTION WITH NITROGLYCERIN

Summary

Nitric oxide (NO) produced within the lungs maintains pulmonary vascular homeostatic properties, modulating leukocyte traffic, platelet aggregation, and vasomotor tone. Because reactive oxygen intermediates generated during reperfusion rapidly quench available NO, it was hypothesized that the NO donor nitroglycerin would enhance lung preservation for transplantation by improving graft vascular homeostasis. Using an orthotopic rat left lung transplant model, with ligation of the native right pulmonary artery to ensure that recipient survival and physiologic measurements depend entirely upon the transplanted lung, transplants were performed in 59 male Lewis rats following 6 hour 4° C. preservation in Euro-Collins solution (EC) alone or EC with supplemental nitroglycerin (NTG). Compared with EC, NTG significantly increased pulmonary arterial flow (2.2±1.4 to 21.4±2.9 ml/min, $p<0.01$), decreased pulmonary vascular resistance (7.4±2.0 to 1.4±0.1×10$^3$ Woods units, $p<0.05$), improved arterial oxygenation (163±57 to 501±31 mm Hg, $p<0.01$), and enhanced recipient survival (14% to 100%, $p<0.001$). These beneficial effects of nitroglycerin were dose-dependent over a range of 0.001 to 0.1 mg/ml. Although nitroglycerin caused significant pulmonary vasodilation during the harvest/flushing period, the direct-acting vasodilator hydralazine caused greater vasodilation than nitroglycerin but failed to improve recipient survival (33% vs 100%, $p<0.05$). Nonvasodilator protective mechanisms of nitroglycerin were also identified. Supplemental nitroglycerin significantly decreased neutrophil accumulation, platelet deposition, and tissue oxidant stress in the reperfused graft. These findings suggest that nitroglycerin added to the pulmonary preservation solution is a simple and effective strategy to improve lung preservation for transplantation.

Introduction

There has been a recent burgeoning of clinical lung transplantation[1], prompted in part by the development of improved pulmonary preservation solutions, but the lungs remain among the most vulnerable organs to ischemia and reperfusion injury during the transplantation process. The inability to preserve lungs beyond 4–6 hours is a major impediment for immunologic cross-matching and hampers efforts at multiple or distant organ procurement. Even with optimal preservation techniques, the perioperative morbidity and mortality remain high, with early graft failure characterized by elevated pulmonary vascular resistance, poor gas exchange, and neutrophil infiltration[2–5]. Recent studies have demonstrated that maintaining endothelial function within cardiac grafts is critical to successful cardiac preservation[6–8], but the current gold-standard clinical lung preservation solution, modified Euro-Collins, consists of a simple electrolyte solution without additives to specifically address maintenance of endothelial function[5,9]. Because the lungs are among the most richly vascularized of organs, it was hypothesized that maintaining normal endothelial properties during preservation and transplantation of the lungs would be critical to the ultimate success of lung transplantation, especially after periods of prolonged preservation.

Of the numerous factors which influence vascular function, endothelium-derived relaxation factor (EDRF, whose identity appears to be nitric oxide; NO[10–13]) has emerged as a key modulator of normal pulmonary vascular physiology. In addition to its effects to prevent neutrophil adherence to the endothelium[14–16], maintain endothelial barrier properties[17], and inhibit platelet aggregation[8,18], NO has an important role in modulating pulmonary vascular tone[19]. The importance of endogenous pulmonary nitric oxide production in normal pulmonary vascular physiology has been shown in numerous experimental models in which nitric oxide synthase inhibition profoundly influences pulmonary vascular tone[20–25]. This view is supported by the recent identification of nitric oxide in exhaled air in humans[26]. Models of cardiac ischemia and reperfusion have demonstrated that both EDRF bioactivity[27] and NO levels[8] fall within minutes of reperfusion, due to the quenching of nitric oxide by superoxide generated during reperfusion (this reaction is rapid, with a rate constant of $10^8$ M$^{-1}$×sec$^{-1}$)[28]. Because reactive oxygen intermediates are formed in especial abundance in the pulmonary reperfusion microenvironment[29–31], it was hypothesized that endothelium-dependent vascular homeostatic properties might be perturbed by the lack of available NO, and that pulmonary preservation might be enhanced by NTG, an NO donor. Using a recently developed model of rat orthotopic lung transplantation in which the native right lung supports the animal during surgery, but is effectively removed from the circulation following transplantation so that physiologic measurements and recipient survival represent function of the transplanted lung[32], the hypothesis that NTG supplementation would enhance NO-related mechanisms of vascular homeostasis following lung transplantation was tested.

Methods

Orthotopic left lung transplantation:

Using inbred male Lewis rats (250–300 gms), hemodynamic and oxygenation measurements were made in an orthotopic left lung transplant model, using a modification[32]

of a previously described technique[33,34]. In brief, the donor rat was heparinized (500 units intravenously) and the superior vena cavae were ligated. Thirty mL of 4° C. preservation solution was infused into the inferior vena cava at a constant pressure (20 mm Hg) and vented out the left atrium. The time required to deliver the 30 mL volume of preservation solution at constant infusion pressure was recorded as an index of pulmonary vascular resistance during harvest. The left pulmonary artery (PA) and pulmonary vein (PV) were then divided, the bronchus was ligated and divided with the lung partially inflated, and the lung was removed. A 14 gauge (G) cuff was placed on each vascular stump, a 16 G grooved cylinder was inserted into the bronchus, and the lung was submerged in 4° C. preservation solution for 6 hours. The recipient rat was anesthetized and intubated (ventilated with 100% oxygen), a left thoracotomy was performed, and the left bronchus, PA, and PV were isolated, cross-clamped, divided, and the native lung was removed. The cylinder (bronchus) and cuffs (PA and PV) were connected to the appropriate recipient structures, maintaining warm ischemic times below 10 minutes. The hilar cross-clamp was released, re-establishing blood flow, and enabling gas exchange. A snare was then passed around the right PA, and Millar catheters (2F; Millar Instruments, Houston, Tex.) were introduced into the main PA and the left atrium (LA). A flow probe (Transonic, Ithaca, N.Y.) was then placed around the main PA.

Preservation solutions consisted of modified Euro-Collins solution (EC), EC with supplemental NTG (Du pont Merck Pharmaceuticals, Manati, Puerto Rico), or EC with supplemental hydralazine (Ciba-Geigy Limited, Basel, Switzerland). EC solution was purchased from Baxter Healthcare (Deerfield, Ill.) and consisted of $Na^+$ 10 mEq/L; $K^+$ 115 mEq/L, $Cl^-$ 15 mEq/L, $HPO_4^-$ —85 mEq/L, $H_2PO_4^-$ 15 mEq/L, $HCO_3^-$ 10 mEq/L, modified by adding magnesium sulfate (10 mL of 10% solution) and glucose (50 mL of 50% solution) to each liter prior to use. After flushing lungs with hypothermic preservation solutions as described, harvested lungs were preserved for 6 hours at 4° C. in 50 mL of preservation solution with the identical composition as that used during harvest.

Measurement of lung graft function

Online hemodynamic monitoring was accomplished using MacLab and a Macintosh IIci computer. The hemodynamic parameters that were measured included LA pressure (mm Hg), PA pressure (mm Hg), and PA blood flow (mL/min). Arterial oxygen tension (mm Hg) was measured during inspiration of 100% oxygen; $pO_2$ was analyzed with a model ABL-2 gas analyzer (Radiometer, Copenhagen, Denmark). Pulmonary vascular resistances (PVRs) were calculated as (mean PA pressure–LA pressure)/PA flow and expressed as Woods units$\times 10^{-3}$. After baseline measurements were taken, the native (right) PA was ligated and serial measurements taken every five minutes for 30 minutes or until recipient death. Recipient death was identified by cessation of cardiac mechanical activity as viewed through the open thorax.

Myeloperoxidase and thiobarbituric acid reactive substances (TBARs) assay:

Thirty minutes following ligation of the native right pulmonary artery, or at the time of recipient death, transplanted lungs were removed, rinsed briskly in physiologic saline, and snap frozen in liquid nitrogen until the time of myeloperoxidase or TBARs assay.

Myeloperoxidase:

Tissue was homogenized in phosphate buffer (50 mM, pH 5.5, 5 ml/gm of tissue) containing hexadecyltrimethyl ammonium bromide (0.5%, Sigma). The assay was performed, as previously described[35], by thawing the sample, centrifuging at 40,000 g for 15 minutes, and decanting the supernatant, which was assayed for myeloperoxidase activity using a standard chromogenic spectrophotometric technique in which test sample (0.03 mL) was added to phosphate buffer (0.97 mL) containing O-dianisidine dihydrochloride (Sigma) and hydrogen peroxide (0.0005%), and change in absorbance at 460 nm was measured over 1 minute (increase in OD was linear over this time interval).

TBARs[36,37]:

The assay was performed by homogenizing tissue in 1.15% KCl (10 ml/gm of tissue). To 0.2 ml of 10% (w/v) tissue homogenate, the following was added; 0.2 mL of 8.1% sodium dodecyl sulfate (SDS; Sigma), 1.5 mL of 20% acetic acid solution (pH 3.5), 1.5 mL of 0.8% aqueous solution of thiobarbituric acid (Sigma), and 0.6 mL of double distilled water. This mixture was heated to 95° C. for 60 minutes followed by rapid cooling to room temperature. An organic extraction was performed by adding 1.0 mL of double distilled water and 5.0 mL of n-butanol:pyridine (15:1, v/v), vortexing, and then centrifuging at 4000 rpm for 10 minutes. The water-immiscible (organic) layer was recovered for measurement of absorbance at 532 nm. Experiments were performed using 1,1,3,3,-tetramethoxypropane as a standard, with the level of lipid peroxides expressed as nmol of malondialdehyde (MDA)/mg protein. Protein content was determined by the method of Lowry et. al[38].

Measurement of graft platelet accumulation

Graft platelet accumulation was determined using $^{111}$Indium-labelled platelets, prepared as described[39]. Blood (5.0 mL) was taken from a gender/strain matched donor rat and heparinized (2500 units). Platelets were isolated by differential centrifugation, first at 300 g for 5 minutes to obtain platelet-rich plasma, which was then washed 3 times at 2,000 g for 15 minutes in 10 ml of acid-citrate-dextrose-anticoagulant (ACD-A; citric acid 38 mM, sodium citrate 75 mM, glucose 135 mM). The pellet was suspended in 5 mL of ACD-A, centrifuged at 100 g for 5 minutes to remove contaminating red blood cells, and the supernatant collected. $^{111}$Indium oxyquinoline (70 μL of 1 mCi/mL, Amersham Mediphysics, Arlington Heights, Ill.) was added with gentle shaking for 30 minutes at room temperature. The radiolabelled platelets were washed 3 times in ACD-A, resuspended in phosphate buffered saline (PBS), and platelet number was adjusted to $5\times 10^7$/mL. After completion of the vascular and bronchial anastomoses, 0.5 mL of $^{111}$Indium-labelled platelet suspension was injected intravenously into the recipient. One minute following platelet infusion (immediately prior to reperfusion), 0.5 mL of blood was taken from the left atrium to determine blood radioactivity, to ascertain blood platelet concentrations to normalize for variations in blood loss during surgery. Five minutes following reperfusion, the native right pulmonary artery was ligated, the graft was removed 10 minutes thereafter, and $^{111}$Indium-platelet deposition quantified by gamma counting. Platelet accumulation was expressed as the ratio of graft radioactivity to blood radioactivity normalized to dry weight.

Statistics

Data were evaluated using the Mann-Whitney U test for two groups, or the Kruskal-Wallis test with Sheff's correction for three groups. Recipient survival data was evaluated using Fisher's exact test. Values are expressed as mean ±SEM, with differences considered statistically significant if $p<0.05$.

Results

To determine whether supplementation of the clinical standard pulmonary preservation solution with NTG would enhance pulmonary vascular function and improve recipient survival following lung transplantation, experiments were performed using Euro-Collins solution as the base solution. The preservation duration of 6 hours was chosen for these experiments based on pilot studies demonstrating significant graft failure with EC alone at this preservation duration[32], as well as the clinical relevance of 4 hrs as the upper limit of acceptable pulmonary preservation in humans. At 6 hours of preservation in EC alone, graft failure occurred rapidly following pulmonary reperfusion, with marked increases in PVR accompanied by declines in pulmonary arterial flow and arterial oxygenation [FIG. 1A]. Although PA pressure rose initially upon ligation of the native (right) pulmonary artery, this was followed by a rapid decline in PA pressure, followed by recipient death. In sharp contrast, when NTG was added to the preservation solution, hemodynamic and functional (arterial oxygenation) parameters were stabilized and the recipient survived the thirty minute observation period [FIG. 1B]. Compared with controls, NTG (0.1 mg/mL) added to the preservation solution increased PA flow ($2.2\pm1.4$ vs $21.4\pm2.9$ mL/min, $p<0.01$) [FIG. 2A], decreased PVR ($7.4\pm2.0$ vs $1.4\pm0.1\times10^3$ Woods units, $p<0.05$) [FIG. 2B], and improved arterial oxygenation ($163\pm57$ vs $501\pm31$ mm Hg, $p<0.01$) [FIG. 2C]. Recipient survival was also improved significantly by supplementation of the preservation solution with NTG compared with controls (14% vs 100%, respectively, $p<0.001$). The beneficial effects of NTG were dose-dependent over a range of 0.001 to 0.1 mg/mL, with maximal beneficial effect obtained by 0.1 mg/ml [FIG. 3].

Because it has been suggested that vasodilators enhance pulmonary preservation by lowering pulmonary vascular resistance during harvest[5,40], resulting in more rapid and effective distribution of hypothermic preservation solution, a determination was made of the flushing time required to deliver identical volumes of preservation solution at identical flushing pressure as a reflection of pulmonary vascular resistance during harvest. These experiments demonstrated that NTG did indeed lower pulmonary vascular resistance during flushing, resulting in more rapid preservation than in its absence ($86.4\pm4.9$ sec vs $192.7\pm9.6$ sec, $p<0.01$ respectively; FIG. 4A). However, harvest vasodilation alone was insufficient to enhance pulmonary preservation, as hydralazine (a direct-acting vasodilator[41]) was even more effective at harvest pulmonary vasodilation than nitroglycerin (flush time $69.3\pm4.5$ sec, $p<0.05$ vs NTG, $p<0.005$ vs EC alone), but relatively ineffective at enhancing pulmonary preservation for transplantation [FIG. 4B].

These data suggested that the beneficial effects of NTG were not exclusively due to its actions as a vasodilator. Because NTG has important effects to inhibit platelet aggregation[42,43] and neutrophil adherence to the reperfused coronary endothelium[8], and neutrophil aggregation and platelet plugging have been implicated in the no reflow-phenomenon[44-46], the effects of NTG added to the preservation solution on graft neutrophil and platelet accumulation following reperfusion were evaluated. NTG (0.1 mg/mL) added to the preservation solution was associated with a significant decline in both neutrophil and platelet accumulation in the reperfused grafts [FIG. 5A and 5B], as quantified by graft myeloperoxidase activity and [111]Indium-labelled platelet deposition, respectively. Neutrophils have been identified as a major cause of tissue damage in both cardiac[47] and pulmonary[29,48-50] ischemia and reperfusion, and may also contribute to the abundant reactive oxygen intermediates formed during pulmonary reperfusion[29]. Because oxygen free radicals rapidly quench available NO, it is possible that the presence of reactive oxygen intermediates contributes to NO unavailability and further neutrophil adherence to the vascular endothelium in the reperfused pulmonary graft. To measure NTG's effects on tissue oxidant stress, thiobarbituric acid reactive substances (TBARs) were measured as MDA equivalents/mg protein in reperfused grafts preserved with or without supplemental NTG. These experiments demonstrated that NTG added to the pulmonary preservation solution reduced graft oxidant stress [FIG. 5C].

Discussion

Vascular endothelium plays a cardinal role in maintaining a homeostatic milieu both within blood vessels and the tissue they supply. Endothelium-derived relaxation factor, whose identity appears to be NO[10-13], serves as an important signalling molecule to reduce vasomotor tone of subjacent vascular smooth muscle[10], maintain endothelial barrier properties[17], reduce platelet aggregation[8,18], and inhibit neutrophil adherence to the endothelial surface[14-16]. Following a period of ischemia, these physiologic endothelial properties are perturbed, favoring vasoconstriction, thrombosis, and neutrophil adhesion, as the inflammatory response is activated. Nitric oxide levels plummet following endothelial cell exposure to hypoxia and reoxygenation, due to the rapid production of superoxide during reoxygenation[8]. Models of cardiac ischemia have demonstrated a rapid reduction in EDRF bioactivity[27] as well as NO levels[8] by direct measurement within minutes of reperfusion. Enhancing nitric oxide-related mechanisms of vascular homeostasis either by providing the NO precursor L-arginine[51,52] or nitric oxide donors such as acidified sodium nitrite[53] and SIN-1[54] can improve vascular function and outcome in these models. Because the loss of available NO may contribute to endothelial dysfunction and pulmonary graft failure during the immediate post-transplant period, the experiments presented here confirmed the hypothesis that an NO donor such as nitroglycerin would enhance NO-related mechanisms of vascular homeostasis within the pulmonary graft.

NO produced within the lungs has important physiologic functions[19], mediated by increases in intracellular cGMP within target cells[55]. Experiments in which nitric oxide synthase antagonists have been given to sheep[20], pigs[21], lambs[22], cats[23], rabbits[24], and rats[25] have shown that endogenously produced NO is important in stimulating basal cGMP production in the lungs and in regulating pulmonary vascular tone. Exhaled NO has been measured in humans[26], confirming the relevance of these observations to man. Nitroglycerin is thought to act by way of intracellular S-nitrosothiol intermediates to directly stimulate guanylate cyclase or to release NO locally in effector cells[55-58], and has recently been shown to increase nitric oxide in expired air[59]. These data confirm that NTG may contribute to local levels of NO within the lungs. Other experiments demonstrate that supplementing NTG in the preservation solution augments tissue cGMP levels (unpublished radioimmunoassay data, 1994), suggesting that incorporating NTG into the pulmonary preservation solution is an effective means of delivery. The current set of experiments were designed to test whether NTG added to a pulmonary preservation solution might augment vascular homeostasis within the reperfused graft, thereby improving graft function and recipient survival. These experiments demonstrate that NTG is unequivocally effective in this regard, resulting in a marked stabilization of pulmonary hemodynamics and improved arterial oxygenation following transplantation.

The preservation of solid organs for transplantation has improved considerably over recent years, due largely to improvements in preservation techniques which enhance parenchymal function of the transplanted organs[9]. The lungs, however, remain among the most problematic organs for transplantation, for reasons that are not fully understood. In these studies, the beneficial effects of NTG in the setting of lung transplantation were not limited to vasodilation, but included reduced neutrophil and platelet accumulation, reduced tissue oxidant stress, and improved gas exchange. These data suggest that vasodilation alone is insufficient to enhance preservation, consistent with the observation of others that inhibiting platelet[60] and neutrophil[29,47-50] accumulation are also important after ischemia and reperfusion. Of the many different preservation strategies described in the experimental literature, only donor prostaglandin administration has been used in clinical lung transplant centers. The use of prostaglandins to improve donor preservation has remained sporadic, however, as their effectiveness is controversial[61-63]. Although prostaglandins per se were not tested in the current series of experiments, harvest vasodilation alone is insufficient to adequately preserve lungs, as demonstrated by experiments in which an effective harvest vasodilating dose of hydralazine failed to protect the lungs during reperfusion. The data discussed herein indicating that the vasodilator hydralazine is an ineffective pulmonary preservative is concordant with previously published data[64]. In contrast with hydralazine, prostaglandins have the theoretical advantage that they improve vascular homeostasis by enhancing levels of the intracellular second messenger cAMP[65,66], not only promoting vasodilation, but inhibiting neutrophil adhesion and platelet aggregation as well[67-69].

The experiments presented here contribute to the growing body of evidence characterizing the detrimental role of neutrophils in pulmonary ischemia/reperfusion. Depletion of neutrophils from the perfusate[29,48-50] has been shown to improve the function of reperfused lungs. Here it is shown that attenuation of neutrophil accumulation within the pulmonary graft by NTG supplementation paralleled improved graft function and recipient survival following orthotopic transplantation. It is not surprising that NTG may interfere with neutrophil accumulation during reperfusion, as NO has been shown to interfere with neutrophil/endothelial adhesion[14-16], and local NO donors/analogs blunt myocardial injury and neutrophil accumulation during cardiac reperfusion[53,54,70]. This attenuated neutrophil infiltration might contribute to the beneficial effects of NTG, because recruited neutrophils release numerous toxic compounds, including superoxide anion, chloramine, hypochlorous acid, hydroxyl radical, and hydrogen peroxide, as well as lysosomal contents such as elastase, the metalloproteases collagenase and gelatinase, neutral proteases, and heparinase[46,47]. The initial source of superoxide following reperfusion in the lungs is not clear, although endothelial cells themselves have been shown in vitro to rapidly generate superoxide following hypoxia and reoxygenation[8,71]. These initially formed oxygen radicals in the reperfusion milieu are potent neutrophil chemoattractants and activators[72,73], which may compound subsequent neutrophil accumulation/activation, resulting in rapid graft failure. The initial inhibition of neutrophil recruitment into the reperfused graft by NTG may not only improve pulmonary parenchymal function, but by decreasing the reactive oxygen intermediate milieu, may result in greater local concentration of NO. As reactive oxygen intermediates induce prolonged expression of the neutrophil adherence molecule P-selectin on the endothelial surface, which mediates rapid neutrophil adhesion to the endothelium[74,75], initial reductions in neutrophil accumulation may be magnified by attenuating the production of reactive oxygen intermediates and further neutrophil adhesion and activation. In this manner, NTG's beneficial vascular effects may be magnified by its ability to attenuate the early phases of neutrophil adhesion. The data showing that NTG reduced graft oxidant stress, measured as a reduction in TBARs (consistent with the reaction of oxygen free radicals with cell membranes[37]), lends credence to these concepts.

Reactive oxygen intermediates formed within lungs subjected to ischemia and reperfusion may rapidly quench NO, forming highly toxic intermediates such as peroxynitrite in the process[28,76]. This has caused reservations about the use of inhaled NO in the setting of pulmonary reperfusion. NTG may avoid this theoretical problem by directly activating guanylate cyclase via S-nitrosothiol intermediates[55-58]. Although agents designed to limit the formation of reactive oxygen intermediates[77-81] have been studied in pulmonary preservation, none are used routinely for clinical lung transplantation. Nitroglycerin may therefore provide an attractive alternative, as it has a long record of safety in myocardial ischemia and reperfusion. These studies emphasize the multipotent benefits of augmenting an endogenous second messenger pathway that appears to be suppressed following ischemia and reperfusion. In this model, supplementation of a pulmonary preservation solution with NTG enhances graft vascular homeostasis at multiple levels, with the end result being improved gas exchange and recipient survival. Supplementation of the pulmonary preservation solution with NTG appears to be a simple pharmacological approach to normalize pulmonary function in the critical early stages following lung transplantation.

REFERENCES FOR THE FIFTH SERIES OF EXPERIMENTS

1. Kaye M P: The registry of the international society for heart and lung transplantation: Tenth official report-1993. *J Heart Lung Transplant* 1993; 12: 541–548.
2. Trulock E P: Lung Transplantation. *Annu Rev Med* 1992;43:1–8
3. Egan T M: Lung preservation. *Seminars in Thor and Cardiovasc Surg* 1992;4:83–89
4. Novick R J, Menkis A H, McKenzie F N: New trends in lung preservation: A collective review. *J Heart Lung Transplant* 1992;11:377–392
5. Kirk A J B, Colguhoun I W, Dark J H: Lung preservation: A review of current practice and future directions. *Ann Thorac Surg* 1993;56:990–1000
6. Pinsky D J, Oz M C, Liao H, Morris S, Brett J, Morales A, Karakurum M, Van Lookeren Campane M, Nowygrod R, Stern D M: Restoration of the cyclic AMP second messenger pathway enhances cardiac preservation for transplantation in a heterotopic rat model. *J Clin Invest* 1993;92:2994–3002
7. Oz M C, Pinsky D J, Koga S, Liao H, Morboe C C, Han D, Kline R, Jeevanandam V, Williams M, Morales A, Popilskis S, Nowygrod R, Stern D M, Rose E A, Michler R E: Novel preservation solution permits 24-hour preservation in rat and baboon cardiac transplant models. *Circulation* 1993;88:II-291–297
8. Pinsky D J, Oz M C, Koga S, Taha Z, Broekman M J, Marcus A J, Liao H, Naka Y, Brett J, Cannon P J, Nowygrod R, Malinski T, Stern D M: Cardiac preservation is enhanced in a heterotopic rat transplant model by supplementing the nitric oxide pathway. *J Clin Invest* 1994;93:2291–2297

9. Belzer F O, Southard J H: Principles of solid-organ preservation by cold storage. *Transplantation* 1988;45:673–676

10. Furchgott R F, Zawadzki J V: The obligatory role of endothelial cells in the relaxation of arterial smooth muscle by acetylcholine. *Nature* 1980;288:373–376

11. Feelisch M, te Poel M, Zamora R, Deussen A, Moncada S: Understanding the controversy over the identity of EDRF. *Nature* 1994;368:62–65

12. Palmer R M J, Ferrige A G, Moncada S: Nitric oxide release accounts for the biologic activity of endothelium-derived relaxing factor. *Nature* 1987;327:524–536

13. Ignarro L J, Buga G M, Wood K S, Byrns R E, Chaudhuri G: Endothelium-derived relaxing factor produced and released from artery and vein is nitric oxide. *Proc Natl Acad Sci* (USA) 1987;84:9265–9269

14. Kubes P, Suzuki M, Granger D N: Nitric oxide: an endogenous modulator of leukocyte adhesion. *Proc Natl Acad Sci* (USA) 1991;88:4651–4655

15. Gaboury J, Woodman R C, Granger D N, Reinhardt P, Kubes P: Nitric oxide prevents leukocyte adherence: role of superoxide. *Am J Physiol* 1993;265:H862–H867

16. Kubes P, Kanwar S, Niu X, Gaboury J P: Nitric oxide synthesis inhibition induces leukocyte adhesion via superoxide and mast cells. *FASEB J* 1993;7:1293–1299

17. Kubes P, Granger D N: Nitric oxide modulates microvascular permeability. *Am J Physiol* 1992;262:H611–615

18. Radomski M W, Palmer R M, Moncada S: Endogenous nitric oxide inhibits human platelet adhesion to vascular endothelium. *Lancet* 1987;II:1057–1058

19. Wiklund N P, Persson M G, Gustafsson L E, Moncada S, Hedqvist P: Modulatory role of endogenous nitric oxide in pulmonary circulation in vivo. *Eur J Pharmacol* 1990;185:123–124

20. Meyer J, Lentz C W, Herndon D N, Nelson S, Traber L D, Traber D L: Effects of halothane anesthesia on vasoconstrictor response to N-G-nitro-L-arginine methyl ester, an inhibitor of nitric oxide synthesis, in sheep. *Anesth Analg* 1993;77:1215–1221

21. Alvine K, Fornhem C, Lundberg J M: Pulmonary effects of endogenous and exogenous nitric oxide in the pig: relation to cigarette smoke inhalation. *Br J Pharmacol* 1993;110:739–746

22. Shaul P W, Farrar M A, Magness R R: Pulmonary endothelial nitric oxide production is developmentally regulated in the fetus and newborn. *Am J Physiol* 1993;265:H1056–H1063

23. McMahon T J, Ignarro L J, Kadowitz P J: Influence of Zaprinast on vascular tone and vasodilator responses in the car pulmonary vascular bed. *J Appl Physiol* 1993;74:1704–1711

24. Sprague R S, Thiemermann C, Vane J R: Endogenous endothelium-derived relaxation factor opposes hypoxic pulmonary vasoconstriction and supports blood flow to hypoxic alveoli in anesthetized rabbits. *Proc Natl Acad Sci* (USA) 1992;89:8711–8715

25. Barer G, Emery C, Stewart A, Bee D, Howard P: Endothelial control of the pulmonary circulation in normal and chronically hypoxic rats. *Journal of Physiology* (London) 1993;463:1–16

26. Gustafsson L E, Leone A M, Person M G, Wiklung N P, Moncada S: Endogenous nitric oxide is present in the exhaled air of rabbits, guinea pigs, and humans. *Biochem Biophys Res Commun* 1991;181:852–857

27. Ma X L, Weyrich A S, Lefer D J, Lefer A M: Diminished basal nitric oxide release after myocardial ischemia and reperfusion promotes neutrophil adherence to coronary endothelium. *Circ Res* 1993;72:403–412

28. Hogg N, Darley-Usmar V M, Wilson M T, Moncada S: Production of hydroxyl radicals from the simultaneous generation of superoxide and nitric oxide. *Biochem J* 1992;281:419–424

29. Adkins W K, Taylor A E: Role of xanthine oxidase and neutrophils in ischemia-reperfusion injury in rabbit lung. *J Appl Physiol* 1990;69:2012–2018

30. Repine J E, Cheronis J C, Rodell T C, Linas S L, Part A: Pulmonary oxygen toxicity and ischemia-reperfusion injury. A mechanism in common involving xanthine oxidase and neutrophils. *Am Rev Respir Dis* 1987;136:483–485

31. Grisham M B, Granger D N: Metabolic sources of reactive oxygen metabolites during oxidant stress and ischemia with reperfusion. *Clin Chest Med* 1989;10:71–81

32. Chowdhury N C, Naka Y, Pinsky D J, Yano O J, Smith C R, Rose E A, Stern D M, Michler R E, Oz M C: Novel technique of orthotopic lung transplantation in rats in which survival and hemodynamic assessment can be measured independent of the native lung. *Surgical Forum Journal;* 1994, in press 33. Mizuta T, Kawaguchi A, Nakahara K, Kawashima Y: Simplified rat lung transplantation using a cuff technique. *J Thorac Cardiovasc Surg* 1989;97:578–581

34. Mizuta T, Nakahara K, Shirakura R, Fujii Y, Kawaguchi A, Minami M, Kawashima Y: Total nonmicrosuture technique for rat lung transplantation. *J Thorac Cardiovasc Surg* 1991;102:159–160

35. Goldblum S E, Wu K M, Jay M: Lung myeloperoxidase as a measure of pulmonary leukostasis in rabbits. *J Appl Physiol* 1985;59:1978–1985

36. Ohkawa H, Ohishi N, Yagi K: Assay for lipid peroxides in animal tissues by thiobarbituric acid reaction. *Analytical Biochemistry* 1979;95:351–358

37. Gutteridge J M C: Aspects to consider when detecting and measuring lipid peroxidation. *Free Radic Res Commun* 1986;1:173–184

38. Lowry O H, Rosebrough N J, Farr A L, Randal R J: Protein measurement with the Folin phenol reagent. *J Biol Chem* 1951;193:265–275

39. Mizutani H, Furubayashi T, Kuriu A, Take H, Tomiyama Y, Yoshida H, Nakamura Y, Inaba M, Yonezawa T, Tarui S, Ikehara S: Analyses of thrombocytopenia in idiopathic thrombocytopenic purpura-prone mice by platelet transfer experiments between (NZW x BXSB)F1 and normal mice. *Blood* 1990;75:1809–1812

40. Baldwin J C, Frist W H, Starkey T D, Harjula A, Starnes V A, Stinson E B, Oyer P E, Shumway N E: Distant graft procurement for combined heart and lung transplantation using a pulmonary artery flush and simple topical hypothermia for graft preservation. *Ann Thorac Surg* 1987;43:670–673

41. Ebeigbe A B, Aloamaka C P: Mechanism of hydralazine-induced relaxation of arterial smooth muscle. *Cardiovasc Res* 1985;19:400–405

42. Chirkov Y Y, Naujalis J I, Sage R E, Horowitz J D: Antiplatelet effects of nitroglycerin in healthy subjects and in patients with stable angina pectoris. *J Cardiovasc Pharmacol* 1993;21:384–389

43. Folts J D, Stamler J, Loscalzo J: Intravenous nitroglycerin infusion inhibits cyclic blood flow responses caused by periodic platelet thrombus formation in stenosed canine coronary arteries. *Circulation* 1991;83:2122–2127

44. Jerome S N, Smith C W, Korthuis R J: CD18-dependent adherence reactions play an important role in the development of the no-reflow phenomenon. *Am J Physiol* 1993;264:H479–H483

45. Kloner R A: No reflow revisited. *J Am Coll Cardiol* 1989;14:1814–1815
46. Kilgore K S, Lucchesi B R: Reperfusion injury after myocardial infarction: the role of free radicals and the inflammatory response. *Clin Biochem* 1993;26:359–370
47. Lucchesi B R, Werns S W, Fantone J C: The role of the neutrophil and free radicals in ischemic myocardial injury. *J Mol Cell Cardiol* 1989;21:1241–1251
48. Hall T S, Breda M A, Baumgartner W A, Borkon M, Brawn J, Hutchins G M, Reitz B A: The role of leukocyte depletion in reducing injury to the lung after hypothermic ischemia. *Curr Surg* 1987;44:137–139
49. Pillai R, Bando K, Schueler S, Zebly M, Reitz B A, Baumgartner W A: Leukocyte depletion results in excellent heart-lung function after 12 hours of storage. *Ann Thorac Surg* 1990;50:211–214
b 50.Shasby D M, Fox R B, Harada R N, Repine J E: Reduction of the edema of acute hyperoxic lung injury by granulocyte depletion. *J Appl Physiol* 1982;52:1237–1244
51. Weyrich A S, Ma X L, Lefer A M: The role of L-arginine in ameliorating reperfusion injury after myocardial ischemia in the cat. *Circulation* 1992;86:279–288
52. Nakanishi K, Vinten-Johansen J, Lefer D J, Zhao Z, Fowler III W C, McGee D S, Johnston W E: Intracoronary L-arginine during reperfusion improves endothelial function and reduces infarct size. *Am J Physiol* 1992;263:H1650–H1658
b 53.Johnson III G, Tsao P S, Mulloy D, Lefer A M: Cardioprotective effects of acidified sodium nitrite in myocardial ischemia with reperfusion. *J Pharm Exp Therapeutics* 1990;252:35–41
54. Siegfried M R, Erhardt J, Rider T, Ma X L, Lefer A M: Cardioprotection and attenuation of endothelial dysfunction by organic nitric oxide donors in myocardial ischemia-reperfusion. *J Pharm Exp Therapeutics* 1992;260:668–675
55. Ignarro L J, Ross G, Tillisch J: Pharmacology of endothelium-derived nitric oxide and nitrovasodilators. *West J Med* 1991;154:51–62
56. Kukovetz W R, Holzmann S, Schmidt K: Cellular mechanisms of action of therapeutic nitric oxide donors. *Eur Heart J* 1991;12 Suppl E:16–24
57. Ignarro L J, Gruetter C A: Requirement of thiols for activation of coronary arterial guanylate cyclase by glycerol trinitrate and sodium nitrite: possible involvement of S-nitrosothiols. *Biochem Biophys Acta* 1994;631:221–231
58. Needleman P, Johnson E M: The pharmacological and biochemical interaction of organic nitrates with sulfhydryls: possible correlations with the mechanism for tolerance development, vasodilation and mitochondrial and enzyme reactions., in Needleman P (ed): *Organic Nitrates: Handbook of Experimental Pharmacology.* New York, Springer-Verlag, 1975, pp 97–114
59. Husain M, Adrie C, Ichinose F, Kavosi M, Zapol W M: Exhaled nitric oxide as a marker for organic nitrate tolerance. *Circulation* 1994;89:2498–2502
60. Cywes R, Packham M A, Tietze L, Sanabria J R, Harvey R C, Phillips M J, Strasberg S M: Role of platelets in hepatic allograft preservation injury in the rat. *Hepatology* 1993;18:635–647
61. Novick R J, Reid K R, Denning L, Duplan J, Menkis A H, McKenzie F N: Prolonged preservation of canine lung allografts: the role of prostaglandins. *Ann Thorac Surg* 1991;51:853–859
62. Hooper T L, Fetherston G J, Flecknell P A, Dark J H, McGregor C G A: The use of prostacyclin analog, iloprost, as an adjunct to pulmonary preservation with Euro-Collins solution. *Transplantation* 1990;49:495–499
63. Bonser R S, Fragomeni L S, Jamieson S W, et a: Effects of prostacyclin E1 in twelve-hour lung preservation.*J Heart Lung Transplant* 1991;10:310–316
64. Hachida M, Morton D L: The protection of ischemic lung with verapamil and hydralazine. *J Thorac Cardiovasc Surg* 1988;95:178–183
65. Heuze-Joubert I, Mennecier P, Simonet S, Laubie M, Verbeuren T J: Effect of vasodilators, including nitric oxide, on the release of cGMP and cAMP in the isolated perfused rat kidney. *Eur J Pharmacol* 1992;220:161–171
66. Nolte C, Eigenthaler M, Schanzenbacher P, Walter U: Comparison of vasodilatory prostaglandins with respect to cAMP-mediated phosphorylation of a target substrate in intact human platelets. *Biochem Pharmacol* 1991;42:253–262
67. Boxer L A, Allen J M, Baehner R L: Diminished polymorphonuclear adherence. Function dependent on release of cAMP by endothelial cells after stimulation of beta-receptors with epinephrine. *J. Clin. Invest.* 1980; 66: 268–274
68. Moncada S, Flower R J, Vane J R: Prostaglandins, prostacyclin, thromboxane $A_2$, and leukotrienes. In: Gilman A G, Goodman L S, Rall T W, Murad F, eds. The pharmacologic basis of therapeutics. New York:Macmillan, 1985; 660–673
69. Jones G, Hurley J V: The effect of prostacyclin on the adhesion of leucocytes to injured vascular endothelium. *J. Pathol.* 1984;142:51–59
70. Lefer D J, Nakanishi K, Johnston W E, Vinten-Johansen J: Antineutrophil and myocardial protecting action of a novel nitric oxide donor after acute myocardial ischemia and reperfusion in dogs. *Circulation* 1993;88:2337–2350
71. Zweier J L, Kuppusamy P, Lutty G A: Measurements of endothelial cell free radical generation: evidence for a central mechanism of free radical injury in postischemic tissues. *Proc Natl Acad Sci* (USA) 1988;85:4046–4050
72. Del Maestro R F, Planker M, Arfors K E: Evidence for the participation of superoxide anion radical in altering adhesive interaction between granulocytes and endothelium, in vivo. *Int J Microcirc Clin Exp* 1982;1:105–120
73. Suzuki M, Inauen W, Kvietys P, Grisham M, Meininger C, Schelling M, Granger H, Granger D: Superoxide mediates reperfusion-induced endothelial cell interactions. *Am J Physiol* 1989;257:H1740–H1745
74. Patel K D, Zimmerman G A, Prescott S M, McEver R P, McIntyre TM: Oxygen radicals induce human endothelial cells to express GMP-140 and bind neutrophils. *J Cell Biol* 1991;112:749–759
75. Mulligan M S, Polley M J, Bayer R J, Nunn M F, Paulson J C, Ward P A: Neutrophil-dependent acute lung injury. Requirement for P-selectin (GMP-140). *J Clin Invest* 1992;90:1600–1607
76. Beckman J S, Beckman T W, Chen J, Marshall P A, Freeman B A: Apparent hydroxyl radical production by peroxynitrite: Implications for endothelial injury from nitric oxide and superoxide. *Proc Natl Acad Sci* (USA) 1994;87:1620–1624
77. Hajjar G B, Toledo-Pereyra L H, MacKenzie G H: Twenty-four hour heart-lung preservation and oxygen free radical scavengers. *Transplant Proc* 1987;XIX:1342–1344
78. Lambert C J , Egan T M, Detterbeck F C, Keagy B A, Wilcox B R: Enhanced pulmonary function with dimethylthiourea for twelve-hour lung preservation. *Ann Thorac Surg* 1991;51:924–930
79. Paull D E, Keagy B A, Entwistle T, Willcox B R: Effect of SOD/catalase infusion at reflow on cardiopulmonary function following lung ischemia in dogs breathing room air. *Curr Surg* 1988;45:292–294

80. Lambert C J, Egan T M: Optimal timing of administration of a free radical scavenger in lung preservation. *Transplantation* 1992;54:205–209

81. Conte J V, Katz N M, Foegh M L, Wallace R B, Ramwell P W: Iron chelation therapy and lung transplantation: effects of deferoxamine. *J Thorac Cardiovasc Surg* 1991;102:1024–1029

What is claimed is:

1. An aqueous solution for organ preservation or maintenance, comprising:
   a) a phosphodiesterase inhibitor in an amount sufficient to maintain vascular homeostasis;
   b) D-glucose in an amount sufficient to support intracellular function and maintenance of cellular bioenergetics;
   c) magnesium ions in an amount sufficient to support intracellular function and maintenance of cellular bioenergetics;
   d) macromolecules of molecular weight greater than 20,000 daltons in an amount sufficient to maintain endothelial integrity and cellular viability;
   e) potassium ions in a concentration greater than about 110 mM; and
   f) a buffer in an amount sufficient to maintain the average pH of the organ preservation or maintenance solution during the period of organ preservation at about physiologic pH or above.

2. The solution of claim 1, wherein the phosphodiesterase inhibitor is selected from the group consisting of isobutylmethylxanthine, indolidan, rolipram, 2-o-propoxyphenyl-8-azapurin-6-one, trequensin, amrinone, milrinone, aminophylline, and dipyridamole.

3. The solution of claim 2, wherein the phosphodiesterase inhibitor is indolidan.

4. The solution of claim 2, wherein the phosphodiesterase inhibitor is rolipram.

5. The solution of claim 2, wherein the phosphodiesterase inhibitor is 2-o-propoxyphenyl-8-azapurin-6-one.

6. The solution of claim 1, wherein the concentration of D-glucose ranges from about 50 mM to about 80 mM.

7. The solution of claim 1, wherein the concentration of magnesium ions ranges from about 2 mM to about 10 mM.

8. The solution of claim 1, wherein the magnesium ions are derived from compounds selected from the group consisting of magnesium sulfate, magnesium gluconate, and magnesium phosphate.

9. The solution of claim 1, wherein the macromolecules are selected from the group consisting of macromolecules having a molecular weight greater than about 100,000 daltons, a polysaccharide, and a polyethylene glycol.

10. The solution of claim 9, wherein the polysaccharide is a dextran.

11. The solution of claim 10, wherein the dextran is a dextran molecule having a molecular weight of 308,000 daltons.

12. The solution of claim 1, wherein the potassium ions are derived from compounds selected from the group consisting of potassium sulfate, potassium gluconate, and monopotassium phosphate ($KH_2PO_4$).

13. The solution of claim 1, wherein the concentration of potassium ions ranges from about 110 mM to about 140 mM.

14. The solution of claim 1, wherein the buffer is monopotassium phosphate ($KH_2PO_4$).

15. The solution of claim 1, further comprising a vasodilator selected from the group consisting of:

adenosine 3',5'-cyclic monophosphate analogues;

guanosine 3',5'-cyclic monophosphate analogues;

adenosine;

nitroglycerin; and pertussis toxin.

16. The solution of claim 15, wherein the vasodilator is dibutyryl adenosine 3',5'-cyclic monophosphate.

17. The solution of claim 16, wherein the concentration of dibutyryl adenosine 3',5'-cyclic monophosphate ranges from about 1 mM to about 4 mM.

18. The solution of claim 15, wherein the concentration of adenosine ranges from about 3 mM to about 20 mM.

19. The solution of claim 15, wherein the concentration of nitroglycerin ranges from about 0.05 grams per liter to about 0.2 grams per liter.

20. The solution of claim 1, further comprising impermeant anions in an amount sufficient to maintain endothelial integrity and cellular viability.

21. The solution of claim 20, wherein the impermeant anions are selected from the group consisting of gluconate anions and lactobionate anions.

22. The solution of claim 21, wherein the impermeant anions are gluconate anions having a concentration that ranges from about 85 mM to about 105 mM.

23. The solution of claim 21, wherein the impermeant anions are gluconate anions selected from the group consisting of potassium gluconate and magnesium gluconate compounds.

24. The solution of claim 1, further comprising an anticoagulant in an amount sufficient to prevent clotting of blood within the capillary bed of the organ.

25. The solution of claim 24, wherein the anticoagulant is selected from the group consisting of heparin and hirudin.

26. The solution of claim 25, wherein the anticoagulant is heparin having a concentration that ranges from about 1000 units/l to about 100,000 units/l.

27. The solution of claim 1, further comprising an antioxidant in an amount sufficient to decrease reperfusion injury secondary to oxygen free radicals.

28. The solution of claim 27, wherein the antioxidant is selected from the group consisting of butylated hydroxyanisole (BHA), butylated hydroxytoluene (BHT), Vitamin C, and Vitamin E.

29. The solution of claim 28, wherein the antioxidant is butylated hydroxyanisole (BHA) at a concentration range from about 25 microM to about 100 microM.

30. The solution of claim 29, further comprising butylated hydroxytoluene (BHT) at a concentration range from about 25 microM to about 100 microM.

31. The solution of claim 1, further comprising a reducing agent in an amount sufficient to decrease reperfusion injury secondary to oxygen free radicals.

32. The solution of claim 1, further comprising N-acetylcysteine in an amount sufficient for cells to produce glutathione.

33. The solution of claim 32, wherein the concentration of N-acetylcysteine ranges from about 0.1 mM to about 5 mM.

34. The solution of claim 1, further comprising an agent that prevents calcium entry into cells in an amount sufficient to prevent calcium entry into cells.

35. The solution of claim 34, wherein the agent that prevents calcium entry into cells is verapamil.

36. The solution of claim 35, wherein the concentration of verapamil ranges from about 2 microM to about 25 microM.

37. The solution of claim 1, further comprising a bacteriostat in an amount sufficient to inhibit bacterial growth.

38. The solution of claim 37, wherein the bacteriostat is selected from the group consisting of cefazolin and penicillin.

39. The solution of claim 38, wherein the bacteriostat is cefazolin having a concentration that ranges from about 0.25 g/l to about 1 g/l.

40. The solution of claim 1, wherein the osmolarity ranges from about 315 mOSm/l to about 340 mOSm/l.

41. A method of preserving or maintaining an organ, comprising contacting the organ with the solution of claim 1.

42. The method of claim 41, wherein the contacting comprises immersion, infusion, flushing, or perfusion.

43. The method of claim 41, wherein the organ is an organ intended for transplantation.

44. The method of claim 41, wherein the organ is a heart.

45. The method of claim 44, wherein the heart is involved in cardiac surgery.

46. The method of claim 41, wherein the organ is a lung.

47. The solution of claim 1, wherein the buffer is sufficient to maintain the average pH of the solution at about physiologic pH during the period of organ preservation.

* * * * *